(12) United States Patent
Akashi et al.

(10) Patent No.: US 7,273,702 B2
(45) Date of Patent: Sep. 25, 2007

(54) APPARATUS FOR PURIFYING NUCLEIC ACID AND METHOD OF PURIFYING NUCLEIC ACID

(75) Inventors: Teruhisa Akashi, Tsuchiura (JP); Yukiko Ikeda, Tsuchiura (JP); Yoshihiro Nagaoka, Tsuchiura (JP); Naruo Watanabe, Tsuchiura (JP); Yuji Miyahara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 278 days.

(21) Appl. No.: 10/478,096

(22) PCT Filed: May 24, 2002

(86) PCT No.: PCT/JP02/05079

§ 371 (c)(1),
(2), (4) Date: Nov. 19, 2003

(87) PCT Pub. No.: WO02/097084

PCT Pub. Date: Dec. 5, 2002

(65) Prior Publication Data

US 2004/0116686 A1    Jun. 17, 2004

(51) Int. Cl.
*C12Q 1/68* (2006.01)
*C12M 1/00* (2006.01)
*C12M 3/00* (2006.01)
*C07H 21/02* (2006.01)

(52) U.S. Cl. .................. 435/6; 435/283.1; 435/287.2; 536/23.1

(58) Field of Classification Search ...................... None
See application file for complete search history.

(56) References Cited

U.S. PATENT DOCUMENTS

| | | | |
|---|---|---|---|
| 3,395,093 A | 7/1968 | Liberti | |
| 5,639,428 A | 6/1997 | Cottingham | 422/112 |
| 6,074,827 A * | 6/2000 | Nelson et al. | 435/6 |
| 6,255,478 B1 | 7/2001 | Komai et al. | 536/25.4 |
| 6,719,896 B1 * | 4/2004 | Clark | 210/91 |
| 2002/0007054 A1 | 1/2002 | Akashi et al. | 536/25.41 |

FOREIGN PATENT DOCUMENTS

| | | |
|---|---|---|
| WO | 96/15450 | 5/1996 |
| WO | WO9721090 A1 * | 6/1997 |
| WO | 97/32645 | 9/1997 |
| WO | 99/13976 | 3/1999 |
| WO | WO 02097084 A1 * | 12/2002 |

* cited by examiner

*Primary Examiner*—Jeffrey Fredman
*Assistant Examiner*—Samuel Woolwine
(74) *Attorney, Agent, or Firm*—Antonelli, Terry, Stout & Kraus, LLP.

(57) ABSTRACT

A nucleic acid refining apparatus, being ease in automation thereof, keeping high in contacting frequency between nucleic acid within a sample and a solid phase during nucleic acid capture processing, thereby proving high capturing rate, comprises: means for separating a liquid containing the nucleic acid therein from said sample through centrifugal force; means for transferring a reagent through the centrifugal force; means for producing a mixture liquid of said reagent transferred through the centrifugal force and a solution containing said nucleic acid therein; a carrier for capturing said nucleic acid; means for transferring said mixture liquid to said carrier through the centrifugal force; heating means for heating said carrier; and a holding means for separating and holding the reagent containing said nucleic acid eluting from said carrier, separating from other reagent, through different centrifugal.

8 Claims, 39 Drawing Sheets a-a' CROSS-SECTION a-a' CROSS-SECTION a-a' CROSS-SECTION a-a' CROSS-SECTION a-a' CROSS-SECTION a-a' CROSS-SECTION a-a' CROSS-SECTION a-a' CROSS-SECTION

FIG.16

STEP 1
SERUM SEPARATION/QUANTIFICATION
- INJECT BLOOD FROM BLOOD INSERTION PORT 6
- CENTRIFUGE BLOOD
- HOLD NECESSARY AMOUNT OF SERUM 56 IN GUTTER 17
    CORRESPONDING FIGS. : FIGS. 8, 9 AND 10

STEP 2
NUCLEAR ACID BONDING
- SERUM 54 IN GUTTER 17 MOVES TO FLOW PASSAGE 36 FOR MIXTURE
- MIXTURE LIQUID MOVES TO FLOW PASSAGE 36 FOR MIXTURE
- MIX AND STIR SERUM 54 AND MIXTURE LIQUID
- MIXTURE LIQUID 55 PASS THROUGH CARRIER 37
- NUCLEAR ACID BONDS ON CARRIER 37
- MIXTURE LIQUID 55 MOVES TO WASTE LIQUID STOPPER 39
    CORRESPONDING FIGS. : FIGS. 11, 12 AND 13

STEP 3
CARRIER RINSING
- RINSING LIQUID A PASSES THROUGH CARRIER 37
- RINSING LIQUID A MOVES TO WASTE LIQUID STOPPER 39
- RINSING LIQUID B PASSES THROUGH CARRIER 37
- RINSING LIQUID B MOVES TO WASTE LIQUID STOPPER 39

STEP 4
NUCLEAR ACID ELUTION/COLLECTION
- ELUTING SOLUTION 56 MOVES TO FLOW PASSAGE 36 FOR MIXING
- HOLD ELUTING SOLUTION 56 ON CARRIER 37
- HEAT ELUTING SOLUTION 56
- ELUTING SOLUTION 56 MOVES TO COLLECTED ELUTING SOLUTION ACCUMULATOR 42
- COLLECT ELUTING SOLUTION 56 FROM ELUTING SOLUTION COLLECTION PORT
    CORRESPONDING FIGS. : FIGS. 14 AND 15 a-a' CROSS-SECTION a-a' CROSS-SECTION

APPARATUS FOR PURIFYING NUCLEIC ACID AND METHOD OF PURIFYING NUCLEIC ACID

RELATED APPLICATION

This is a U.S. national stage filed under 35 U.S.C. §371 of international application PCT/JP02/05079 filed May 24, 2002, which claims priority of Japanese application 2001-156512 filed May 25, 2001.

TECHNICAL FIELD

The present invention relates to an apparatus and a method for purifying or refining nucleic acids therewith.

BACKGROUND ART

With advance of the molecular biology, various technologies are developed in relation with genes, and with those technologies, it is possible to separate and identify diseased genes, in much more numbers thereof. As a result, in the field of medical treatment, the molecular biological technologies are introduced into diagnoses or checking methods, thereby enabling the diagnosis, which was impossible in the conventional art, and also achieving great reduction in the number of days necessary for the checks.

Such the advance is mainly owned to an amplification method of a nucleic acid sequence, in particular, practicing of PCR (Polymerase Chain Reaction) technology or method. With this PCR method, it is possible to amplify the nucleic acid in a solution, specifically upon a sequence thereof. For this reason, it is possible to prove the existence of a virus living in blood serum of an extremely small quantity or amount, indirectly, by amplifying the nucleic acid sequences as the genes of the virus through the PCR method, for detection thereof. However, in a case where this PCR method is applied in daily clinical diagnoses in a clinical field, there still remain several problems to be dissolved. Among of them, a pre-treatment is very important, in particular, for estimation by using the PCR method, i.e., the capacity of refining of the nucleic acid sequence, and for this reason, there are proposed several technologies or methods in relation to the refining of the nucleic acid sequence.

For a first technology relating to the conventional art, a method is already disclosed, as described in Japanese Patent Laying-Open No. Hei 2-289596 (1990), for example, wherein silica particles, which can combine with the nucleic acid sequence under existence of chaotropic materials, are used as a solid-phase for use of combining or coupling with nucleic acid, for separating the solid-phase coupling with the nucleic acid sequence from a liquid, and thereafter complex of the solid-phase and the nucleic acid sequence (solid-phase/nucleic acid) is rinsed, thereby eluting the nucleic acid sequence from the complex, depending upon necessity thereof.

Also, for a second technology relating to the conventional art, a method is already disclosed, for example, in Japanese Patent Laying-Open No. Hei 8-320274 (1996), wherein a single nucleic acid sequence is extracted, collected, and/or separated, with using a large number of containers for a single sample, a large number of detachable tips for separate injection, filters, and particles of magnetic substance or material.

Further, for a third technology relating to the conventional art, a method is already disclosed, for example, in Japanese Patent Laying-Open No. 2000-514928 (2000) of PCT application, wherein blood plasma is separated from blood (i.e., whole blood) and further is mixed with an extremely small quantity of liquid, as well as detection of antibiotics, by using a microscopic channel, a chamber, a capillary, a deposable valve, etc.

However, the following problems can be listed, in the case where the methods or technologies disclosed in the conventional arts mentioned above are applied, actually.

First of all, with the method described in the Japanese Patent Laying-Open No. Hei 2-289596 (1990), mentioned as the first technology relating to the conventional art in the above, since the nucleic acid sequence can not be collected within the same device, it is difficult in automation thereof. Further, it is also difficult to increase the frequency of contact between the nucleic acid and the silica particles in a short time. In particular, in the case where the nucleic acid is low in the concentration, such as $10^2$ copy/ml, for example, as a target contained within a sample, it is very difficult to increase the contact frequency in a short time.

Also, with the method described in the Japanese Patent Laying-Open No. Hei 8-320274 (1996), mentioned as the second technology relating to the conventional art in the above, processes are complex for extracting, collecting, and/or separating of the nucleic acid sequences, therefore the automation is difficult. Further, with this conventional art, since those processes cannot be treated within the same device, the problem of contamination thereof may be worried about.

On the other hand, in the second conventional art, it is disclosed that a pipette, to which the tip is connected, is linked with a cylinder (i.e., a syringe pump), so as to control the suction/discharge amount by means of a servomotor or a pulse-motor, severely. For this reason, for maintaining sufficient suction/discharge of the sample, it is impossible to increase the density of the silica-membrane filter. On the other hand, if applying a low density silica-membrane filter having a superior penetration of liquid, as a matter of course, the probability of collecting the nucleic acid becomes small. In particular, if the nucleic acid is low in the concentration, such as around $10^2$ copy/ml, for example, as mentioned above, being the target contained within the sample, the contact frequency between the silica-membrane filter and the nucleic acids is reduced further, when the sample passes through that silica-membrane filter.

Also, in the Japanese Patent Laying-Open No. 2000-514928 (2000) of PCT application, as the third conventional art, there is disclosed the method for separating blood plasma from a very small amount of blood, such as about 150 μL, for example. However, in this publication, nothing is disclosed therein, about a technology nor a method for refining the nucleic acid.

Therefore, an object according to the present invention is to provide an automatic refining apparatus and a method thereof, which can be easily automated, wherein the contact frequency between the nucleic acids as the target within a sample and the solid-phase, thereby increasing trapping rate or ratio of the nucleic acids, even under the condition of the low concentration, such as around $10^2$ copy/ml, for example, and further to provide a structure for refining nucleic acids for building up thereof, and to provide a gene analyzing apparatus and/or a refining apparatus for chemical materials with use thereof.

DISCLOSURE OF THE INVENTION

According to the present invention, for achieving the object mentioned above, there is provided a nucleic acid refining apparatus for refining nucleic acid from a sample containing the nucleic acid therein, comprising: means for separating a liquid containing the nucleic acid therein from said sample through centrifugal force; means for transferring a reagent through the centrifugal force; means for producing a mixture liquid of said reagent transferred through the centrifugal force and a solution containing said nucleic acid therein; a carrier for capturing said nucleic acid; means for transferring said mixture liquid to said carrier through the centrifugal force; heating means for heating said carrier; and a holding means for separating and holding the reagent containing said nucleic acid eluting from said carrier, separating from other reagent, through different centrifugal.

Also, according to the present invention, there is provided a nucleic acid refining apparatus for refining nucleic acid from a sample containing the nucleic acid therein, comprising: means for separating a liquid containing the nucleic acid therein from said sample through centrifugal force; reagent holding means for holding a reagent therein; means for transferring said reagent from said reagent holding means through the centrifugal force; means for producing a mixture liquid of said reagent transferred through the centrifugal force and a solution containing said nucleic acid therein; a carrier for capturing said nucleic acid; means for transferring said mixture liquid to said carrier through the centrifugal force; heating means for heating said carrier; and a holding means for separating and holding the reagent containing said nucleic acid eluting from said carrier, separating from other reagent, through different centrifugal.

Also, according to the present invention, there is provided a nucleic acid refining apparatus for refining nucleic acid from a sample containing the nucleic acid therein, comprising: a device having: means for separating a liquid containing the nucleic acid therein from said sample through centrifugal force; means for transferring a reagent through the centrifugal force; means for producing a mixture liquid of said reagent transferred through the centrifugal force and a solution containing said nucleic acid therein; a carrier for capturing said nucleic acid; means for transferring said mixture liquid to said carrier through the centrifugal force; heating means for heating said carrier; and a holding means for separating and holding the reagent containing said nucleic acid eluting from said carrier, separating from other reagent, through different centrifugal; and a supply means for supplying said reagent from an outside of said device.

Also, according to the present invention, there is provided a nucleic acid refining apparatus for refining nucleic acid from a sample containing the nucleic acid therein, comprising: a round front surface cover having a hole, which is sealed by a rubber at one end thereof; a gap defined between said front surface cover; a first round disc and having a separation gel, which lies in said gap, for separating a solution including nucleic acid therein from said sample and a groove, which lies in said gap, for quantification of said solution; a second round disc having: a reagent reservoir containing a reagent therein; a flow passage; a carrier for combining the nucleic acid thereon; an elution reservoir for accumulating an eluting solution, being obtained from said reagent after eluting the nucleic acid therein; and a waste liquid reservoir, being provided following said eluting solution reservoir, for accumulating the reagent other than said eluting solution, and having a flow passage being opened into an outside; and a round reverse surface cover having a heating body, wherein a device is built up with said reverse surface cover, said second disc, said first disc and said front surface cover, being piled up sequentially, and has a punching portion, through which said solution and said reagent can move in a direction of thickness of said device, by punching a hole at a predetermined position within said device.

Further, according to the present invention, in the structure of the nucleic acid refining apparatus as described in the above, wherein a "U" shaped flow passage is provided between said elution solution reservoir and said waste liquid reservoir on said second disc, or wherein a branch passage, being divided in the direction of thickness of said device, is provided between said elution solution reservoir and said waste liquid reservoir on said second disc, or wherein a filter, having lower penetrability than that of said carrier, is provided between said elution solution reservoir and said waste liquid reservoir on said second disc.

And, according to the present invention, also for achieving the object mentioned above, there is provided a method for refining nucleic acid from a sample containing the nucleic acid therein, comprising the following steps of: a step for separating a solution containing nucleic acid therein from said sample through centrifugal force, with using a separation gel, within a first gap provided within an inside of a device, being formed with laminating a plural number of round discs; a step for quantification of said solution with provision of a first hole within said device; a step for transferring said quantified solution into a flow passage, as a second gap formed within said device, with provision of a second hole within said second device; a step for transferring a combining liquid of a first reagent into said flow passage through centrifugal force, with provision of a third hole within said device; a step for producing a mixture liquid of said solution quantified within said flow passage and said combining liquid; a step for passing said combining liquid through said carrier for capturing said nucleic acid thereon through centrifugal force, thereby transferring it into a waste liquid reservoir as a third gap formed within said device; a step for transferring a rinsing liquid of a second reagent into said flow passage through the centrifugal force, with provision of a fourth hole within said device; a step for making said rinsing liquid pass through said carrier through the centrifugal force, thereby transferring it into said waste liquid reservoir; a step for transferring an eluting solution of a third reagent into said flow passage through the centrifugal force, with provision of a fifth hole formed within said device; a step for letting said carrier hold said eluting solution therein, and heating said carrier; a step for transferring said eluting solution containing said nucleic acid separated from said carrier therein into an eluting solution reservoir formed within a flow passage following said carrier, through the centrifugal force, thereby holding the eluting solution therein separating from other reagents; and a step for collecting said eluting solution from said eluting solution reservoir, from an outside of said device.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; and an eluting solution holder portion for holding the eluting solution including the nucleic acid therein, being captured on said nucleic acid capture portion once and separated therefrom, after flowing through said nucleic acid capture portion, wherein said eluting solution hold portion is formed within a flow passage communicating between said nucleic acid capture portion and said waste portion.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; and an eluting solution holder portion for holding the eluting solution including the nucleic acid therein, being captured on said nucleic acid capture portion once and separated therefrom, after flowing through said nucleic acid capture portion, wherein said eluting solution holder portion is formed in a downstream of said nucleic acid capture portion, while said waste portion in a downstream of said eluting solution holder portion.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; and an eluting solution holder portion for holding the eluting solution including the nucleic acid therein, being captured on said nucleic acid capture portion once and separated therefrom, after flowing through said nucleic acid capture portion, wherein said eluting solution holder portion is formed on an outer periphery side of said nucleic acid capture portion, while said waste portion on an outer periphery side of said nucleic acid holder portion.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; an eluting solution holder portion for holding the eluting solution including the nucleic acid therein, being captured on said nucleic acid capture portion once and separated therefrom, after flowing through said nucleic acid capture portion; and a waste liquid flow passage communicating between said eluting solution holder portion and said waste portion, wherein said waste liquid flow passage comprises a holder portion communication portion being communicated with an area, being located on an outer periphery side rather than an area on a most-inner periphery side of said eluting solution holder portion, an inner periphery side area portion, being located in a downstream of said communication portion and in an inner periphery side rather than said communication portion, and a waste portion communication portion, being located in a downstream of said inner periphery side area portion and being communicated with said waste portion, being located in an outer periphery side rather than said inner periphery side area portion.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; an eluting solution holder portion for holding the eluting solution including the nucleic acid therein, being captured on said nucleic acid capture portion once and separated therefrom, after flowing through said nucleic acid capture portion; and a waste liquid flow passage communicating between said eluting solution holder portion and said waste portion, wherein a connection portion between said eluting solution holder portion and said waste liquid flow passage is formed in an outer periphery side rather than a most-inner periphery portion of said waste liquid flow passage, and in an inner periphery side rather than a most-outer periphery portion of said waste liquid flow passage.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a first reagent supply portion, through which a first reagent is supplied to said nucleic acid capture portion; a waste portion, into which is wasted said first reagent flowing through said nucleic acid capture portion; a second reagent supply portion, through which a second reagent is supplied to said nucleic acid capture portion, having a function of releasing said nucleic acid captured on said nucleic acid capture portion therefrom, being larger than that of said first reagent; a second reagent holder portion for separating the nucleic acid captured on said nucleic acid capture portion therefrom, thereby to hold said second reagent contained within an inside thereof; and a waste liquid flow passage communicating between said second reagent holder portion and said waste portion, wherein an area located on said waste flow passage between a most-inner periphery portion and a connection portion with said second reagent holder portion, and an area located on an outer periphery side than said most-inner periphery portion of said second reagent holder portion are formed, so that a total volume of them is smaller than that of said first reagent to be supplied, while being larger than that of said second reagent to be supplied.

Also, according to the present invention, there is provided a nucleic acid refining structure, being formed to be rotatable, comprising: a supply portion, through which is supplied a liquid including nucleic acid therein; a nucleic acid capture portion, onto which is captured the nucleic acid within said supplied liquid; a washing liquid supply portion, through which a washing liquid is supplied to said nucleic acid capture portion; a waste portion, into which is wasted said washing liquid flowing through said nucleic acid capture portion; an eluting solution supply portion, through which an eluting solution is supplied into said nucleic acid capture portion; an eluting solution holder portion for holding the eluting solution including the nucleic acid therein, being captured on said nucleic acid capture portion once and separated therefrom, after flowing through said nucleic acid capture portion; and a waste liquid flow passage communicating between said eluting solution holder portion and said waste portion, wherein an area located on said waste flow passage between a most-inner periphery portion and a connection portion with said eluting solution holder portion and an area located on an outer periphery side than said most-inner periphery portion of said eluting solution holder portion are formed, so that a total volume of them is smaller than that of said washing liquid to be supplied, while being larger than that of said eluting solution to be supplied.

Also, according to the present invention, there is provided a nucleic acid refining apparatus comprising: a receiver portion for receiving said nucleic acid refining structure described in the above; and a rotary driving mechanism for rotating said nucleic acid refining structure.

Also, according to the present invention, there is provided the nucleic acid refining apparatus as described in the above, further comprising an analysis mechanism for analyzing genes of said nucleic acid, with using said nucleic acid introduced into said eluting solution holder portion of said nucleic acid refining structure.

Also, according to the present invention, there is provided the nucleic acid refining apparatus as described in the above, further comprising a heating device for heating said nucleic acid introduced into said eluting solution holder portion of said nucleic acid refining structure.

Also, according to the present invention, in the nucleic acid refining apparatus as described in the above, wherein said washing liquid is controlled, so as to be held within said waste portion, being supplied from said nucleic acid capture portion through said eluting solution holder portion, in an amount larger than that a total volume of an area located on said waste flow passage between a most-inner periphery portion and a connection portion with said eluting solution holder portion and an area located on an outer periphery side than said most-inner periphery portion of said eluting solution holder portion, while said eluting solution is controlled, so as to be held within said eluting solution holder portion, being supplied through said nucleic acid capture portion, in an amount smaller than that the total volume of the area up to the connection portion between the most-inner periphery portion of said waste flow passage and said eluting solution holder portion and the area located on the outer periphery side than said most-inner periphery portion of said eluting solution holder portion.

And, according to the present invention, there is further provided a chemical material refining structure comprising: a supply portion, through which is supplied a liquid including a first chemical material therein; a first chemical material capture portion, onto which is captured said chemical material within said supplied liquid; a first reagent supply portion, through which a first reagent is supplied to said first chemical material capture portion; a waste portion, into which is wasted said first reagent flowing through said first chemical material capture portion; a second reagent supply portion, through which a second reagent is supplied to said first chemical material capture portion, having a function of releasing said chemical material from said first chemical material capture portion, being larger than that of said first reagent; and a second reagent holder portion for holding said second reagent including said first chemical material therein, being captured on said first chemical material capture portion once and then separated therefrom after flowing through said first chemical material capture portion, wherein said second reagent holder portion is formed within a flow passage communicating between said first chemical martial holder portion and said waste portion.

Furthermore, in the present invention, though the rinsing liquid is described to be a fluid having a function of removing impurities other than the nucleic acid included within said nucleic acid holder portion, while the eluting solution to be a liquid having a function of separating the nucleic acid from said capture portion, thereby containing the nucleic acid in itself, however it is not used to be limited only to that having such the function of eluting, and it has a large function of separating the nucleic acid from said capture portion, rather than that of the rising liquid.

BRIEF DESCRIPTION OF THE DRAWINGS

FIG. 16 is a flowchart for showing a method for refining nucleic acids according to the present invention;

Figure 1:
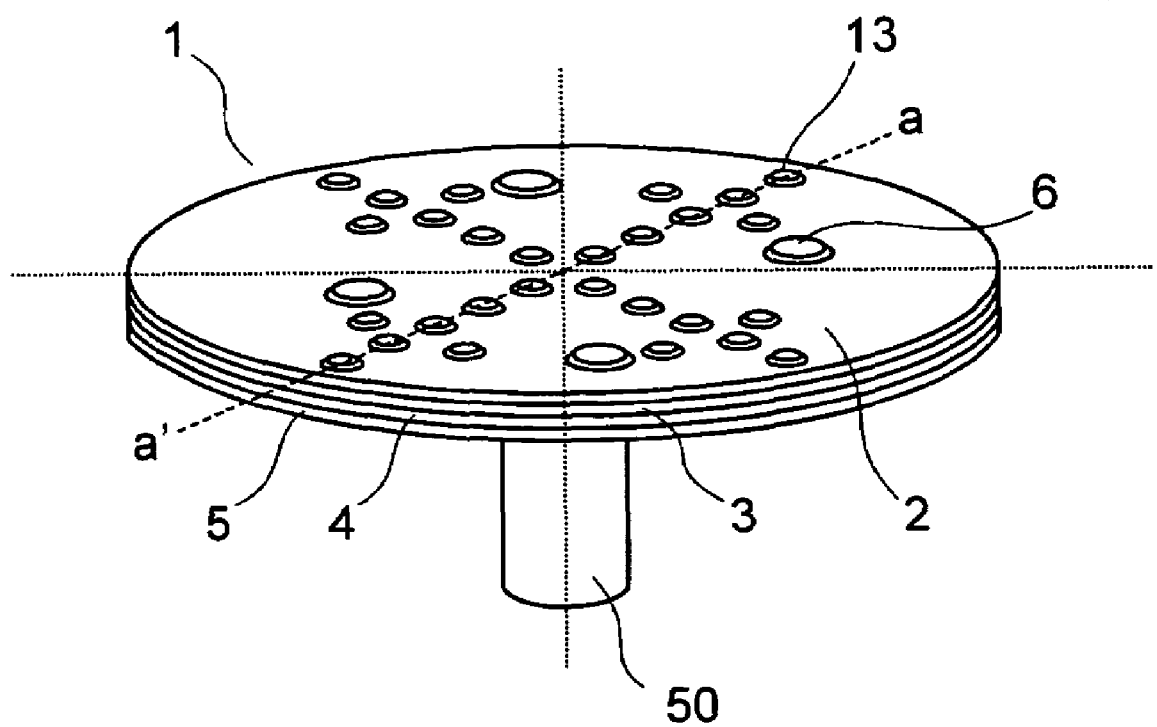
FIG. 1 is a perspective view of a disc device, being an embodiment according to the present invention.
Figure 18:
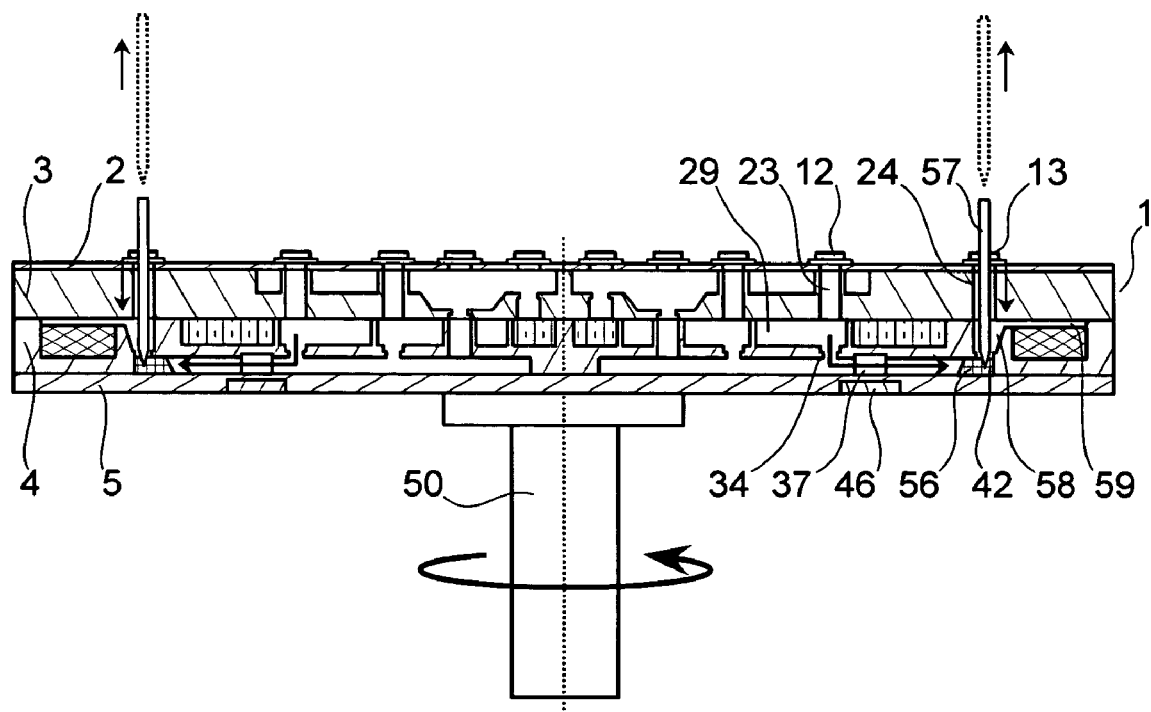
Figure 19:
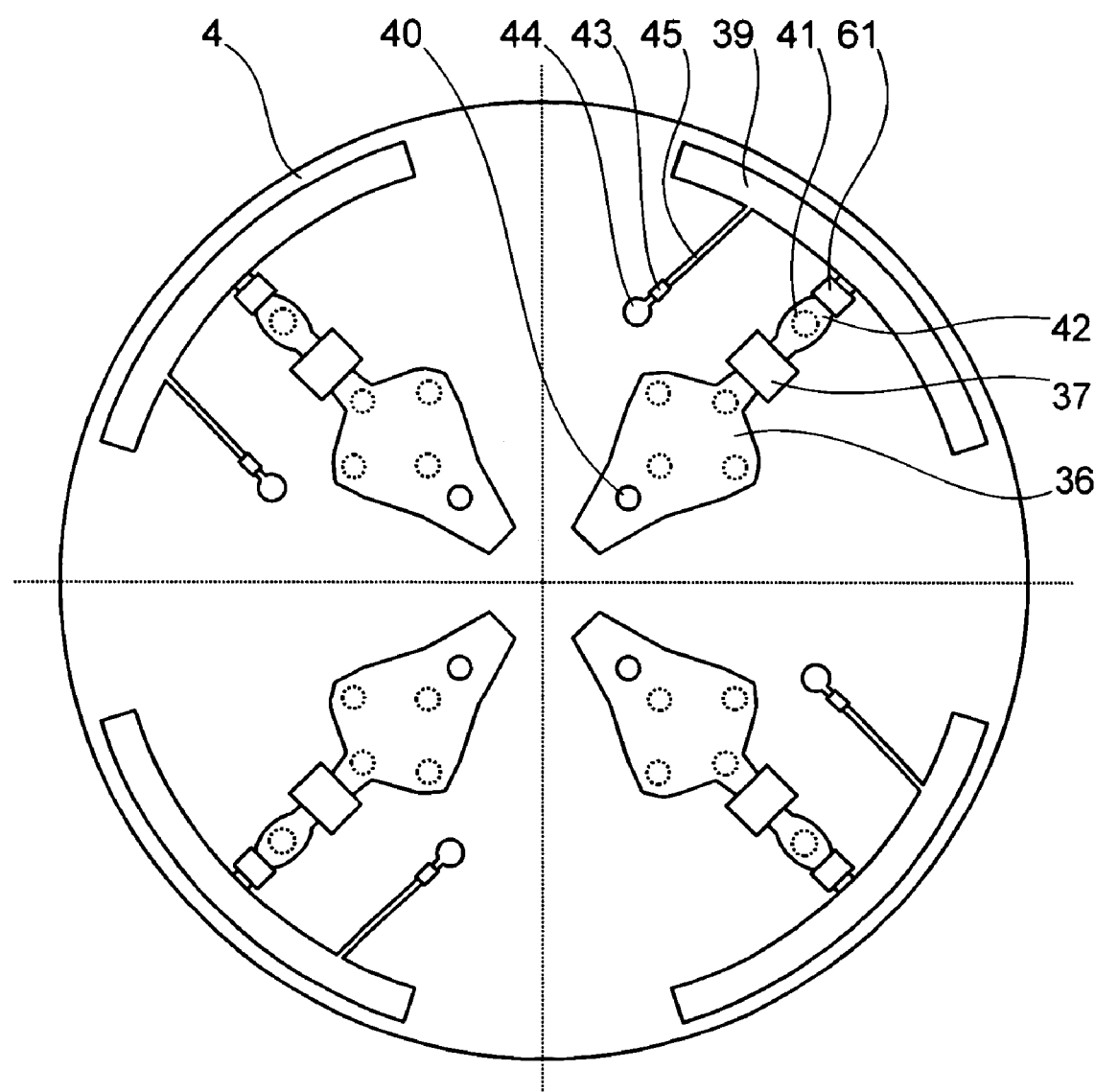
Figure 20:
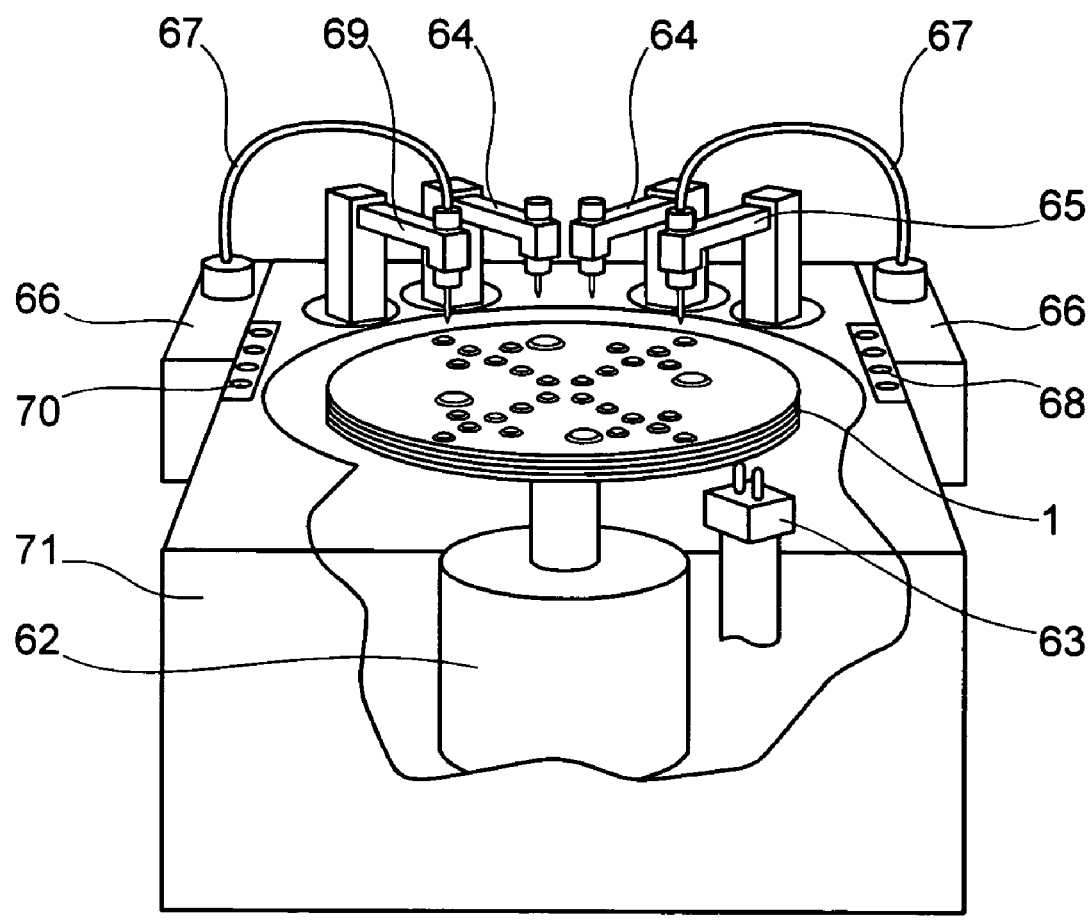
Figure 21:
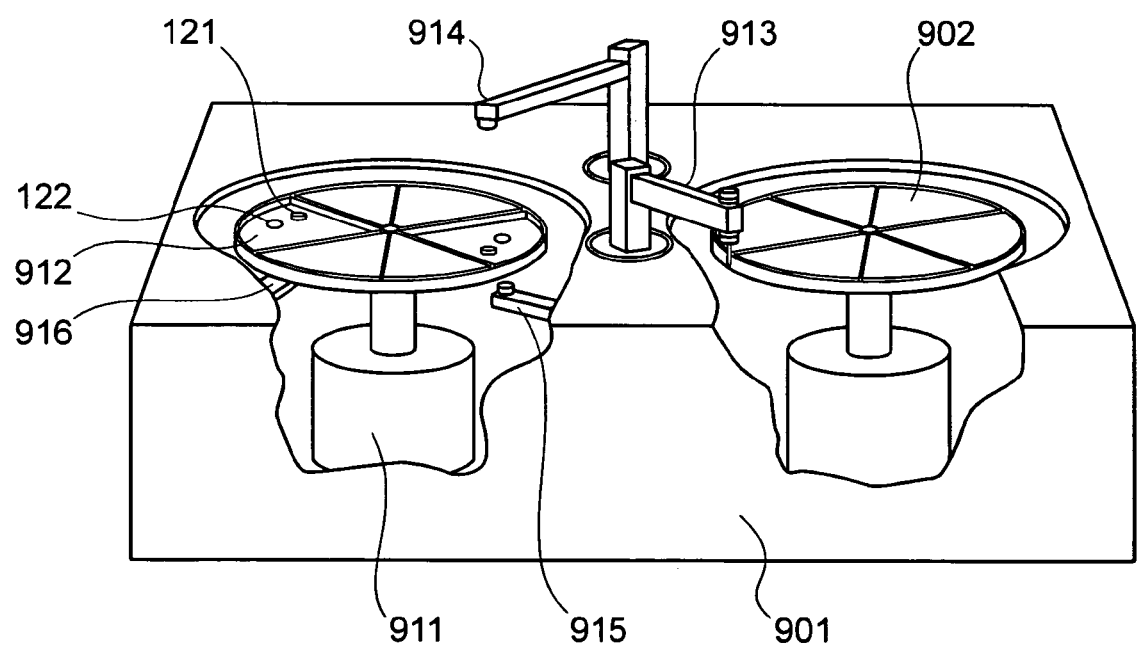
Figure 22:
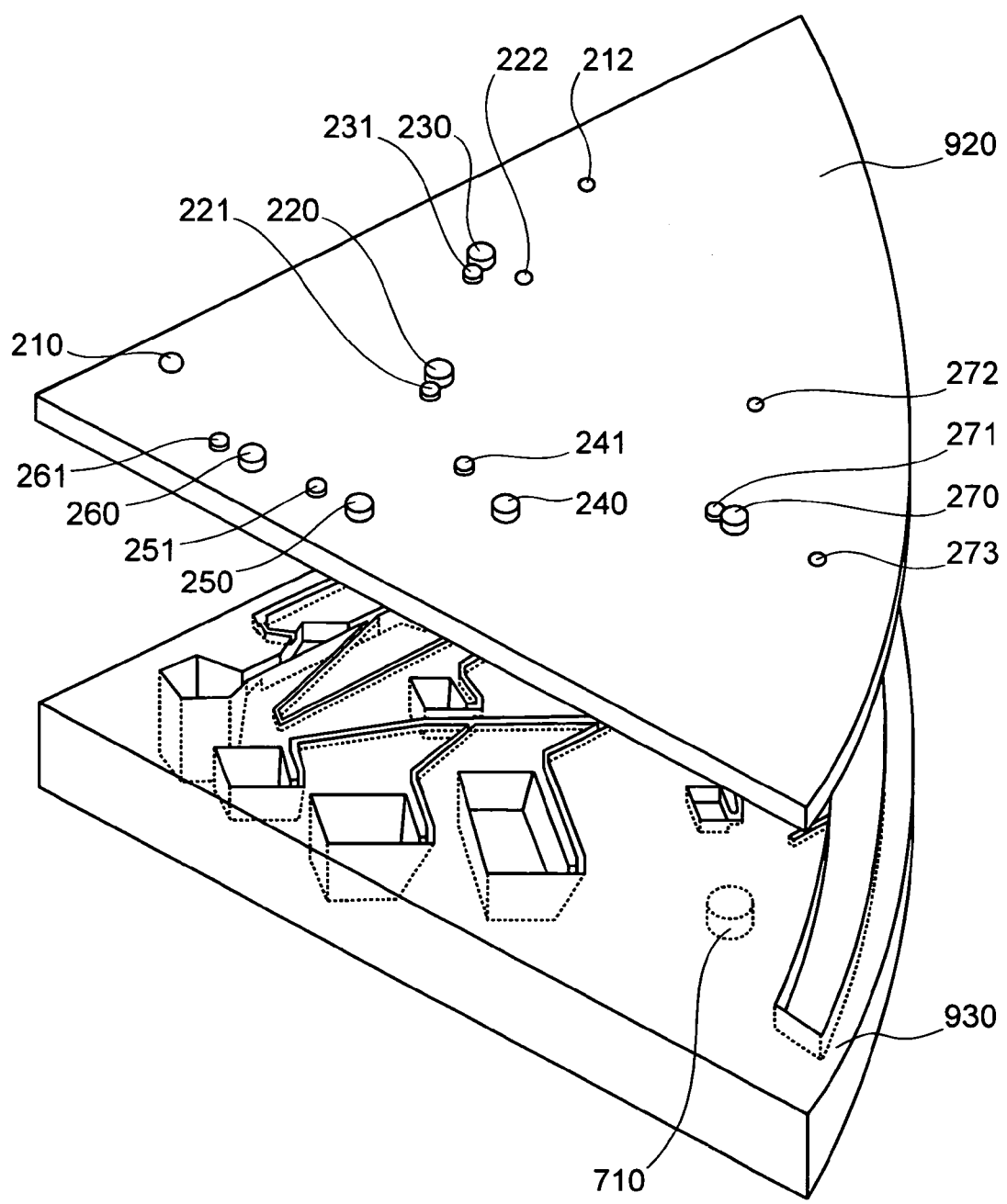
Figure 23:
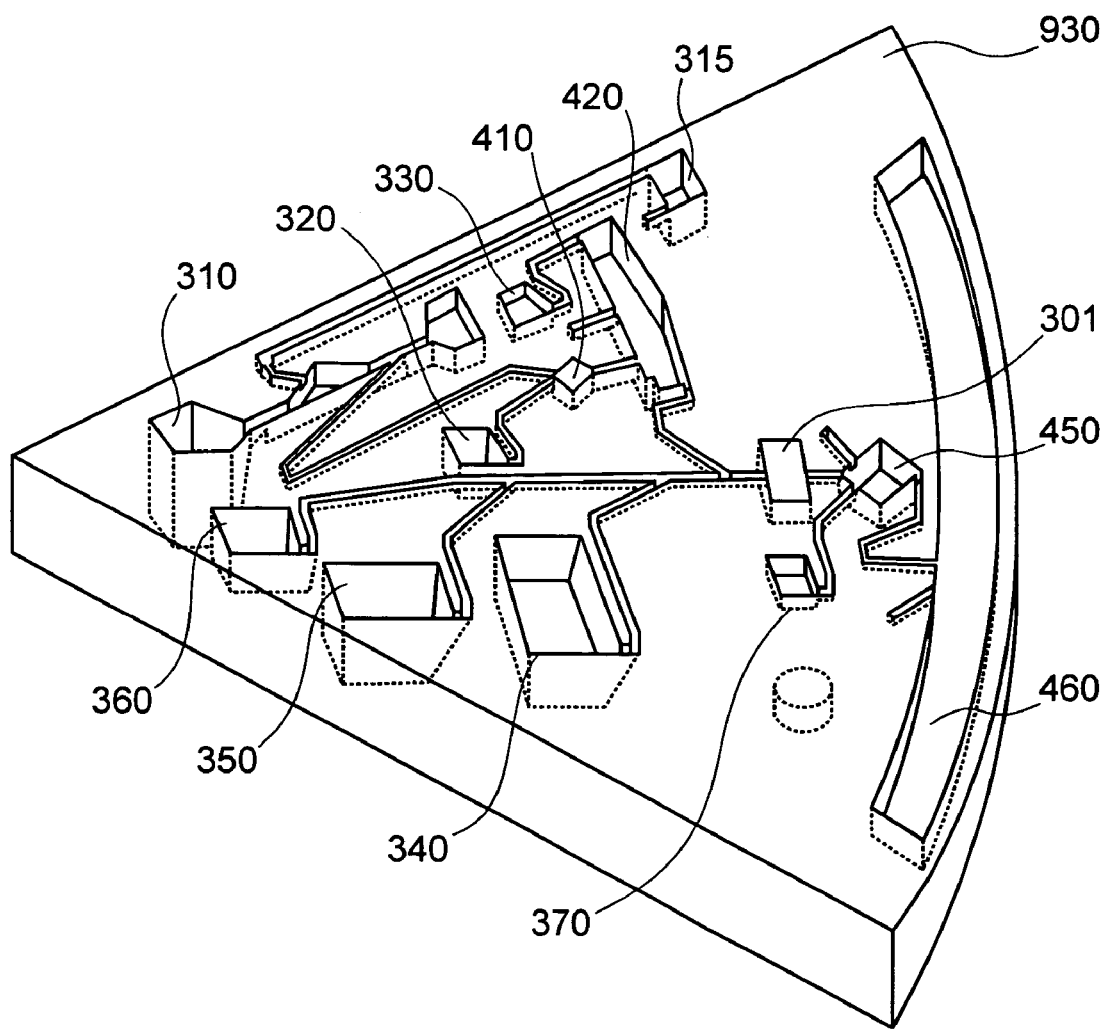
Figure 24:
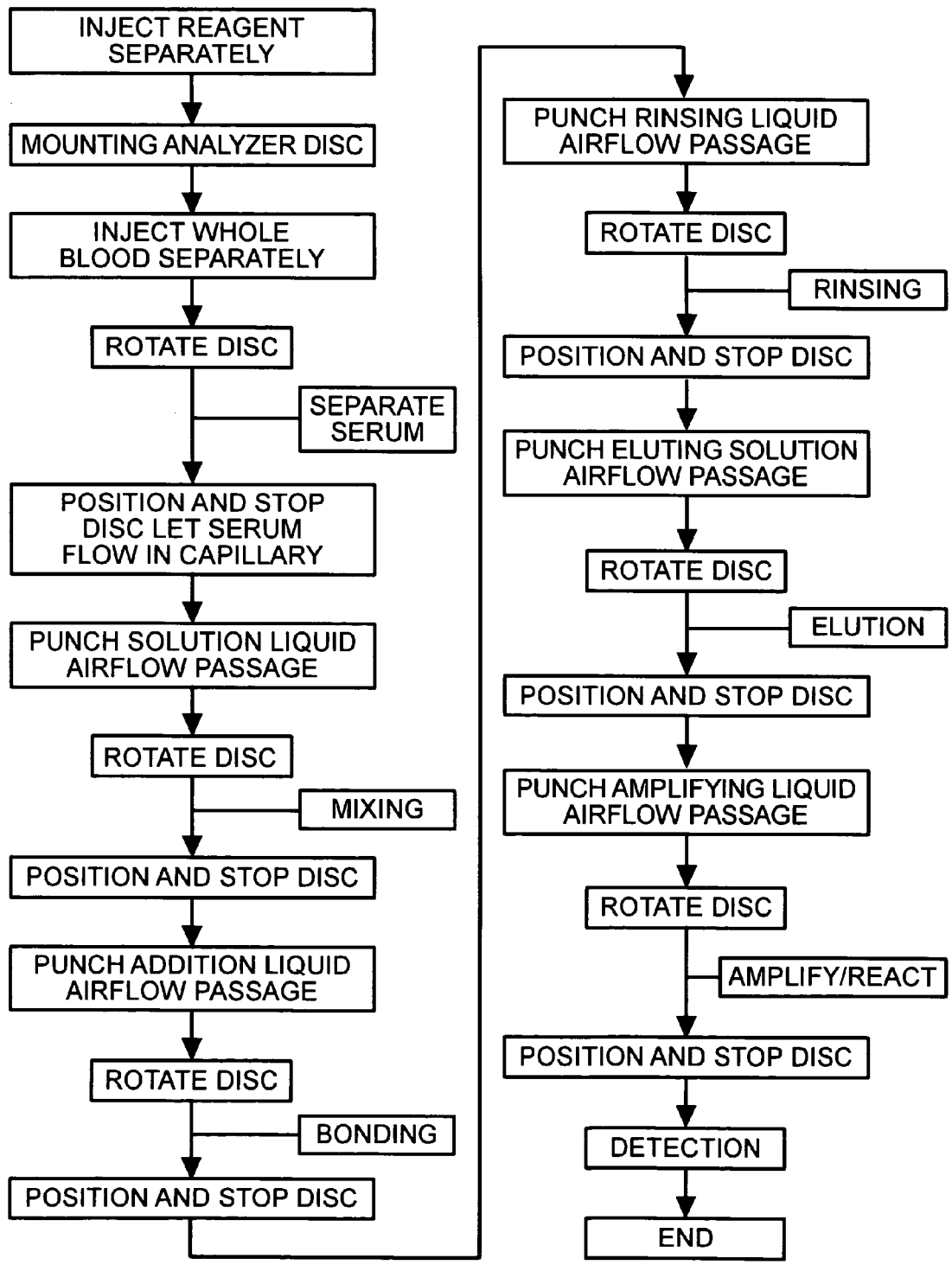
Figure 25:
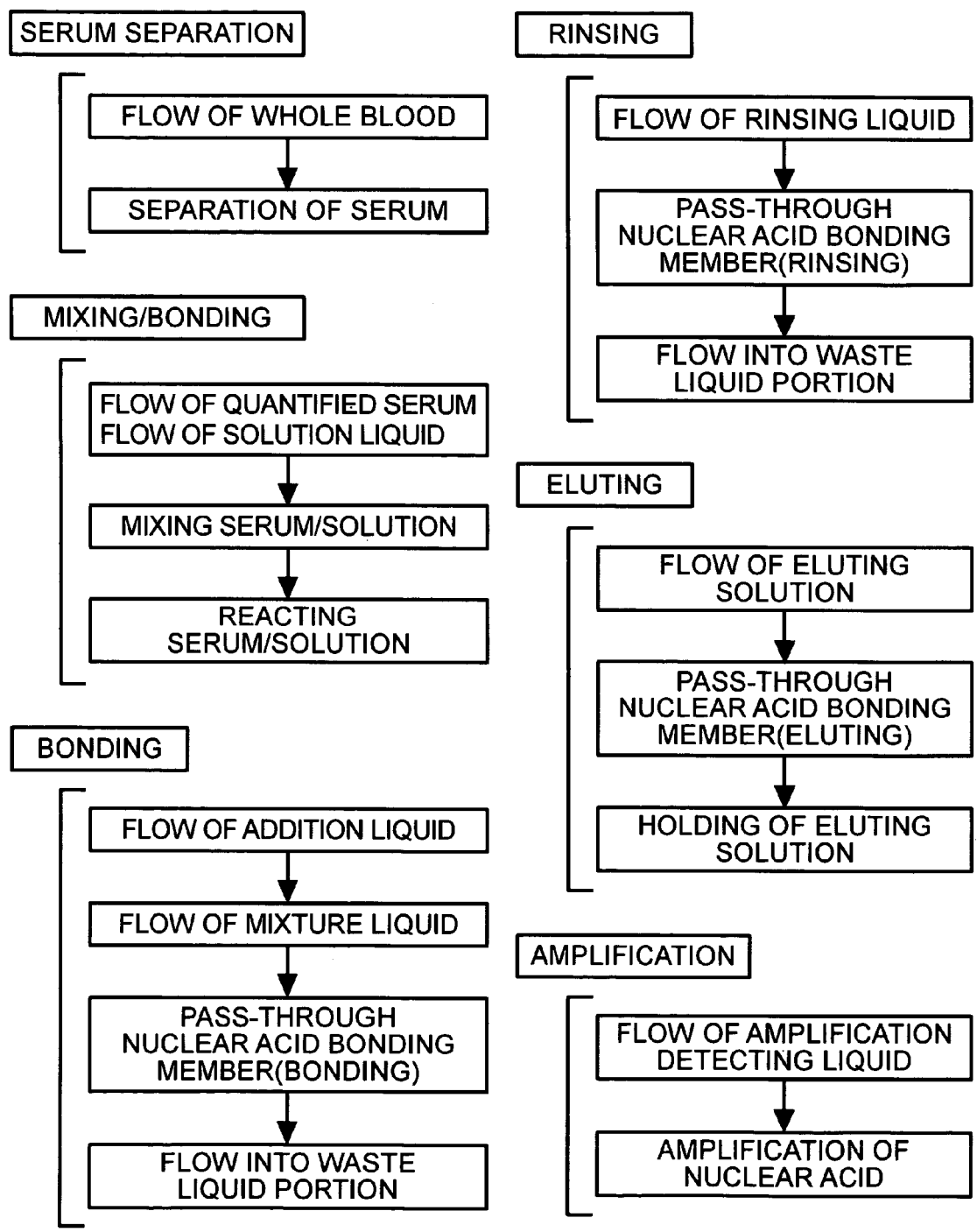
Figure 26:
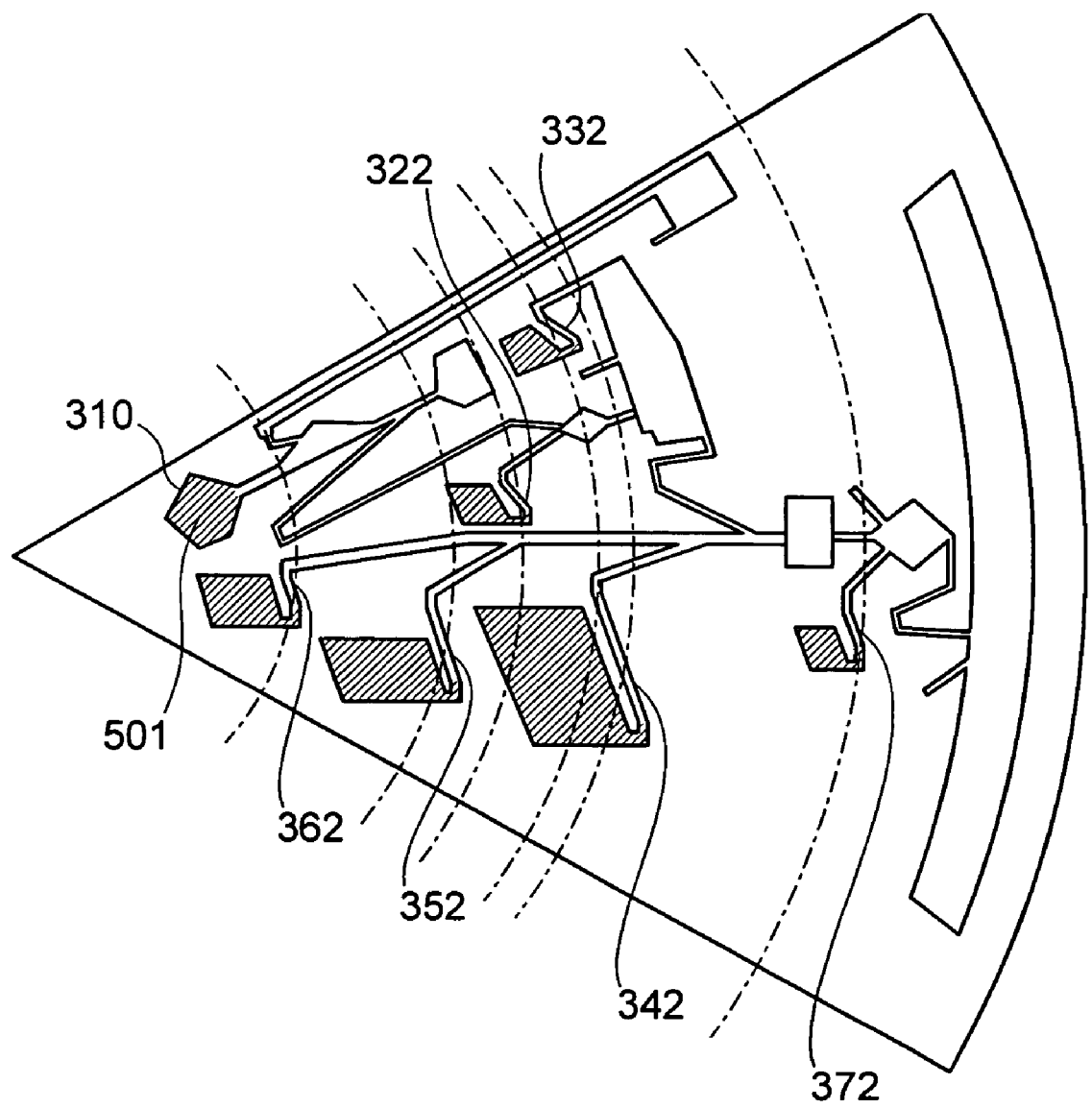
Figure 27:
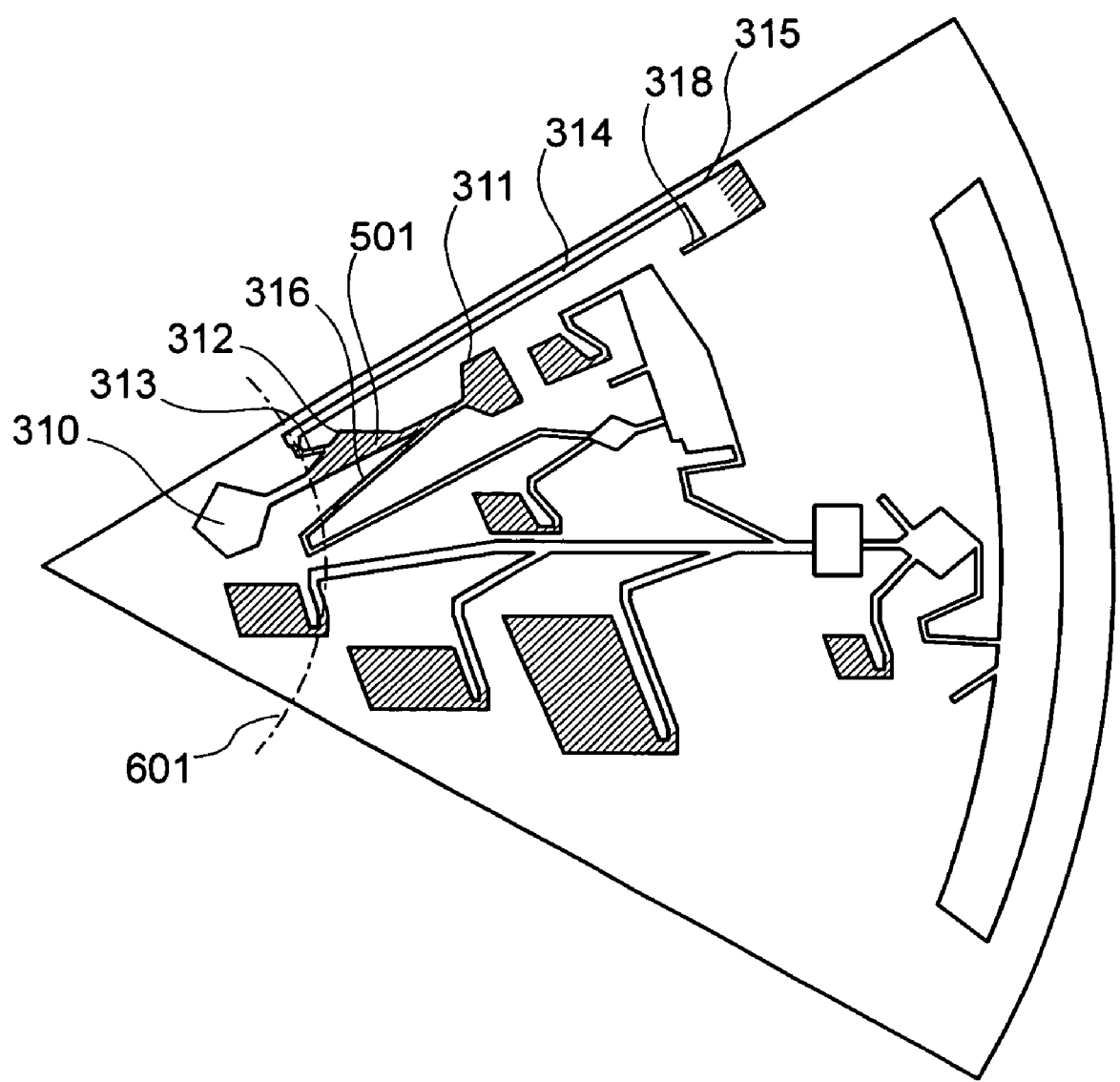
Figure 28:
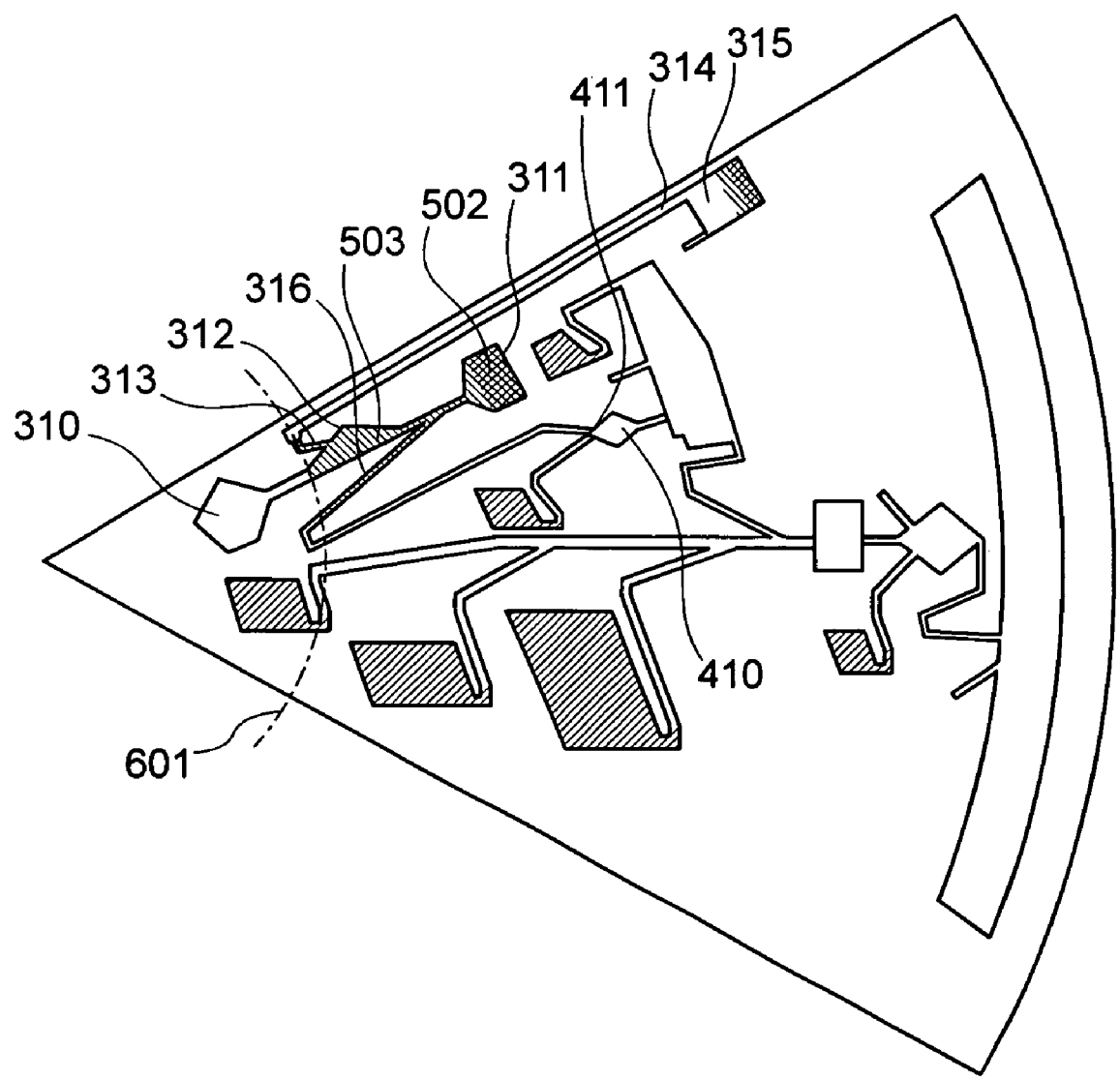
Figure 29:
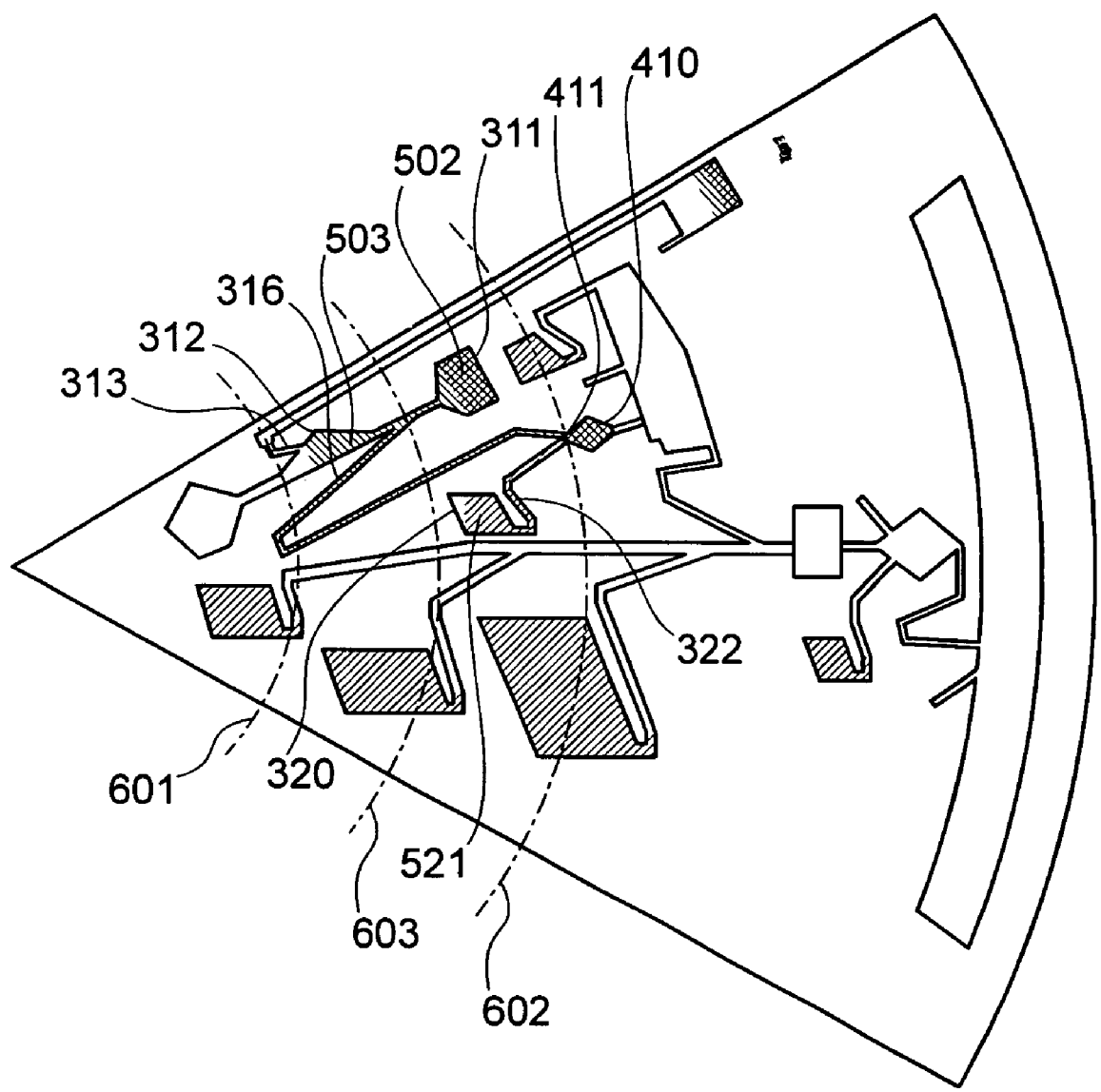
Figure 30:
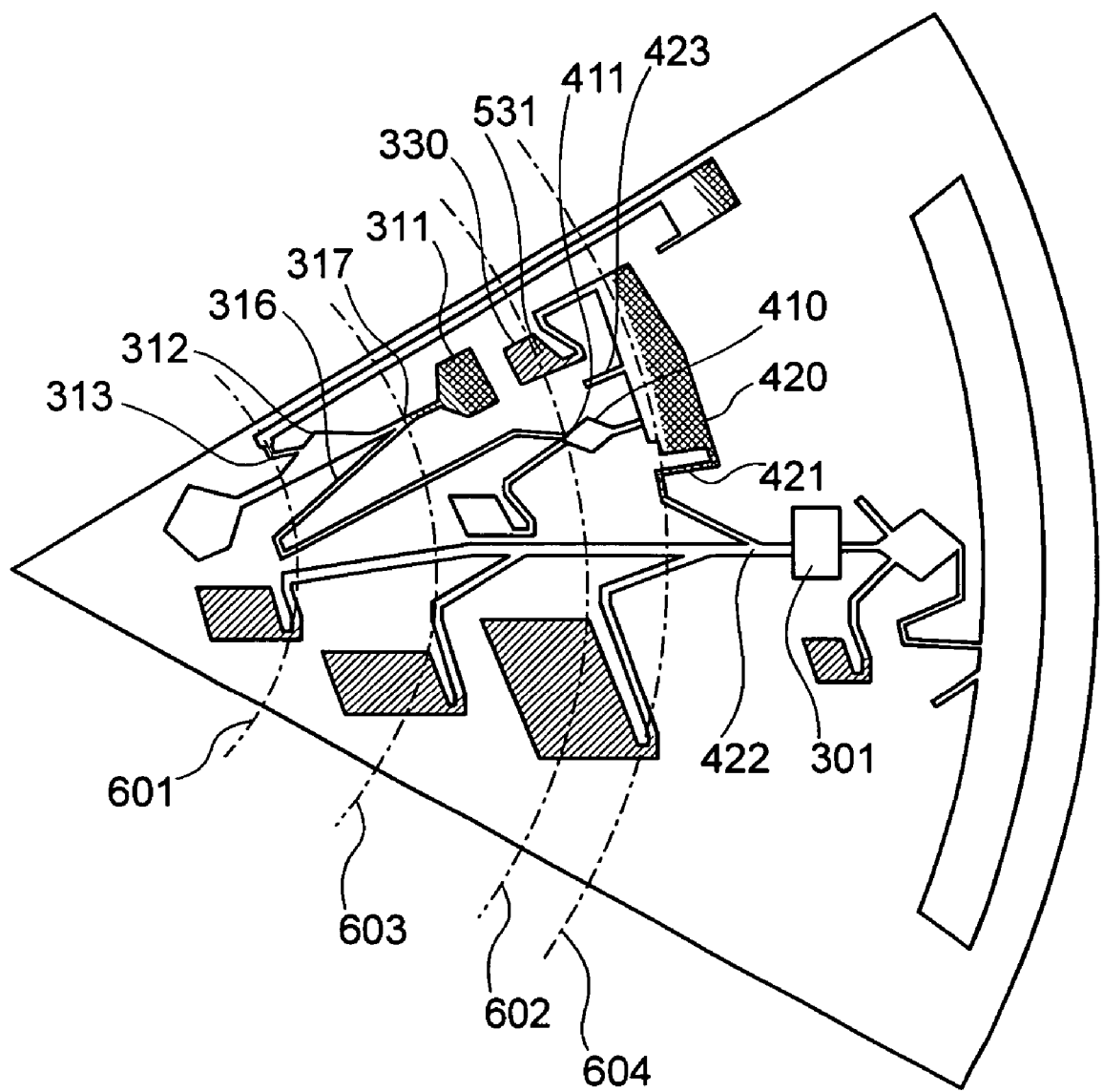
Figure 31:
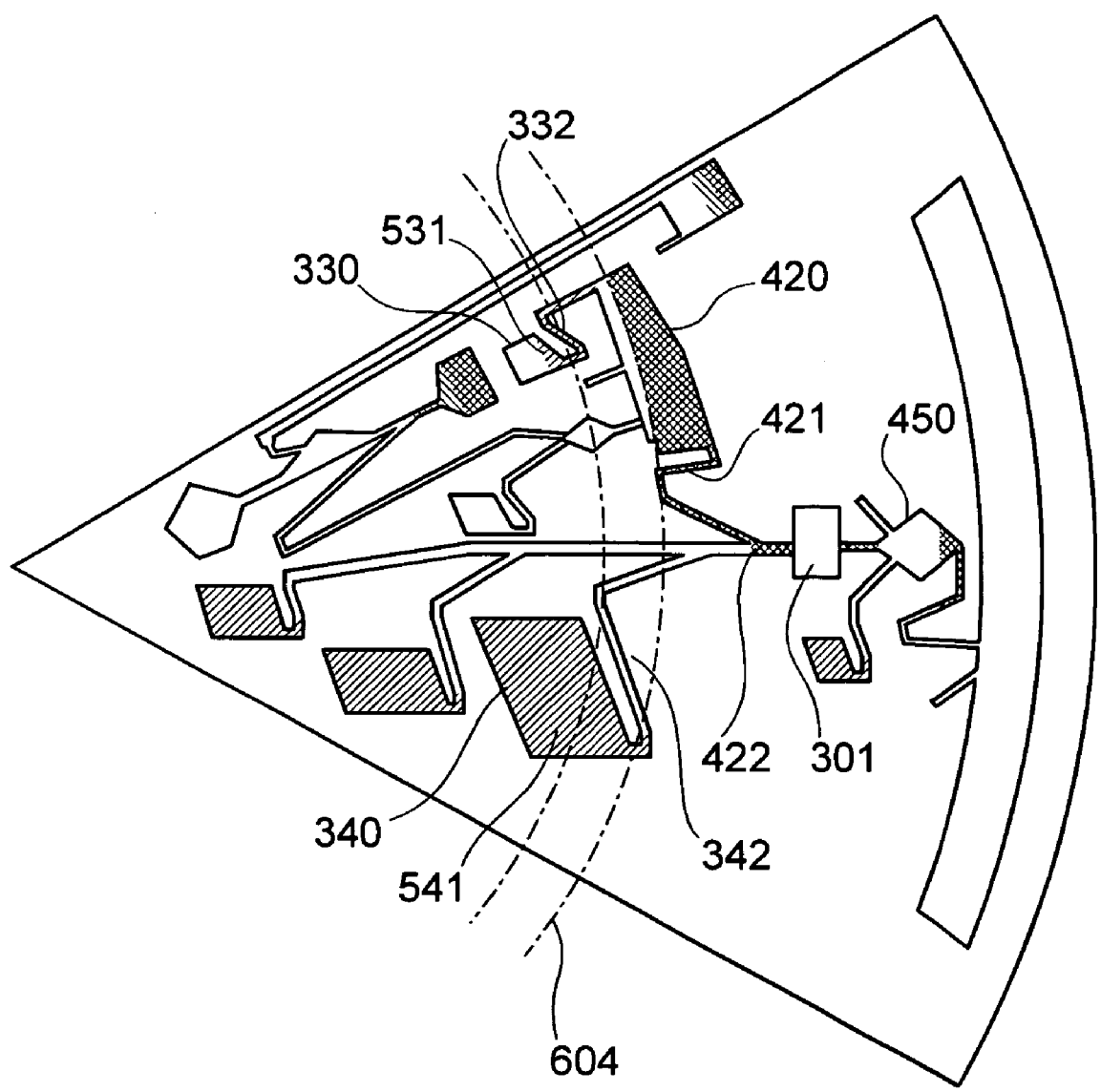
Figure 32:
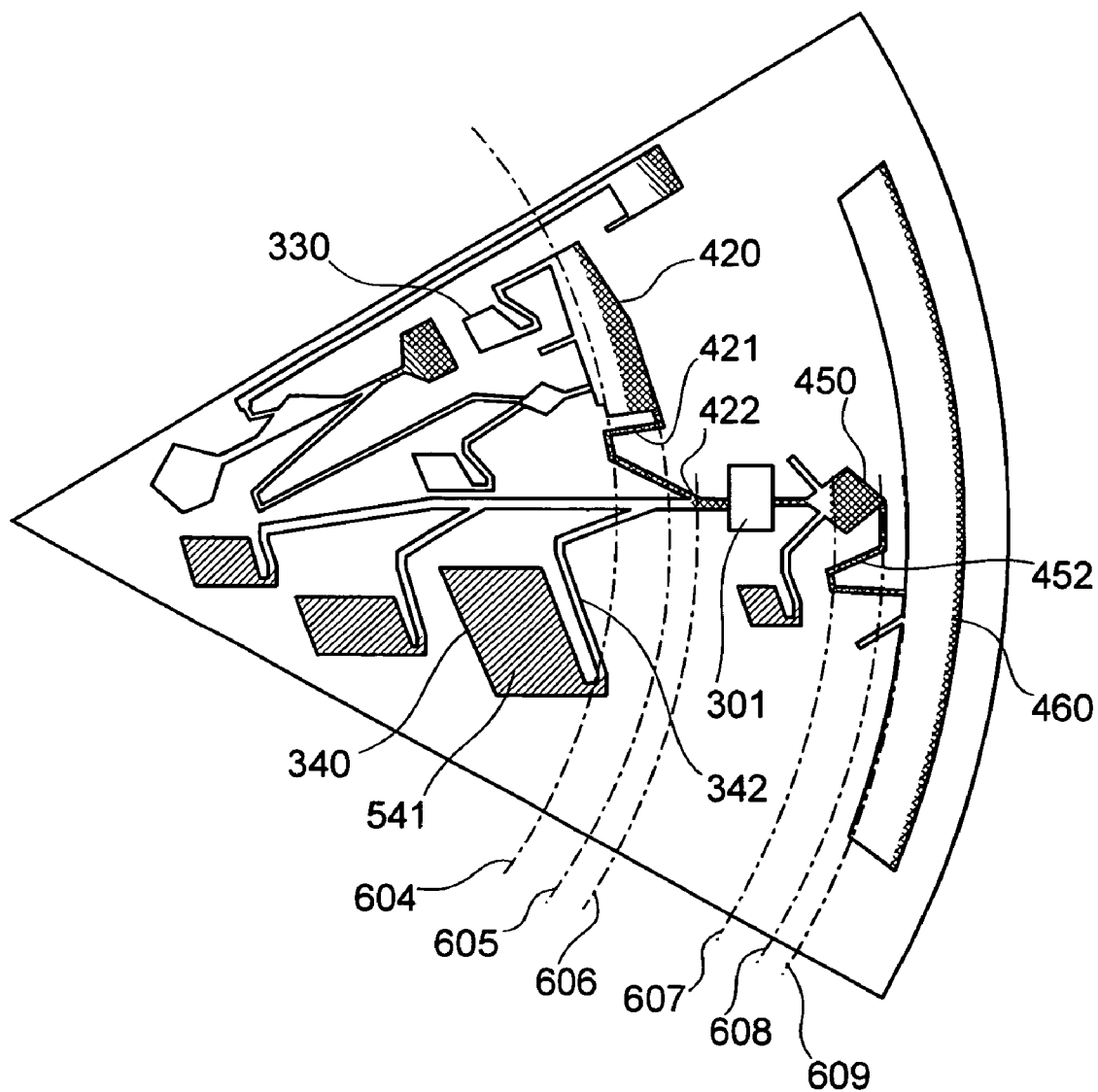
Figure 33:
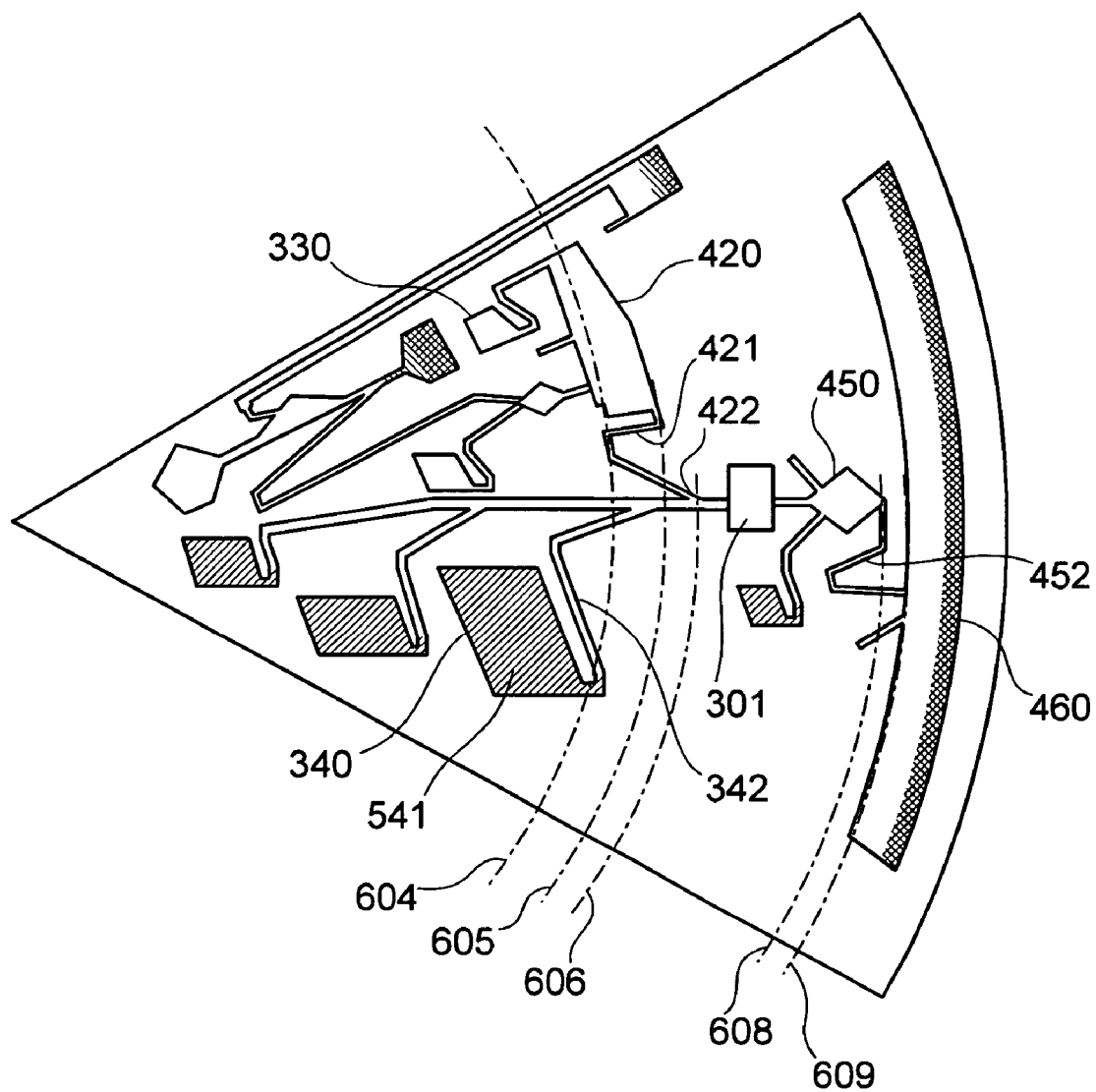
Figure 34:
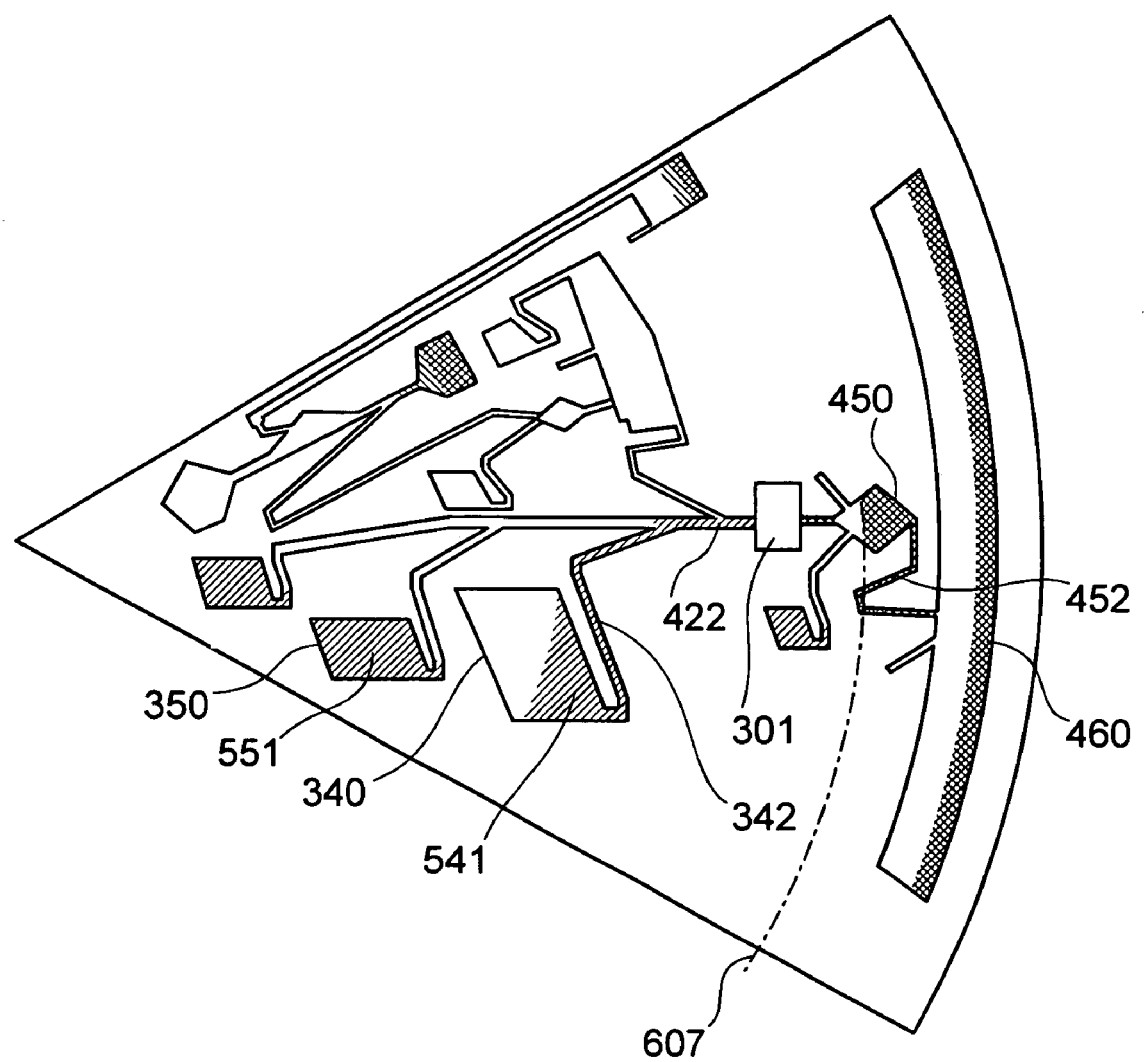
Figure 35:
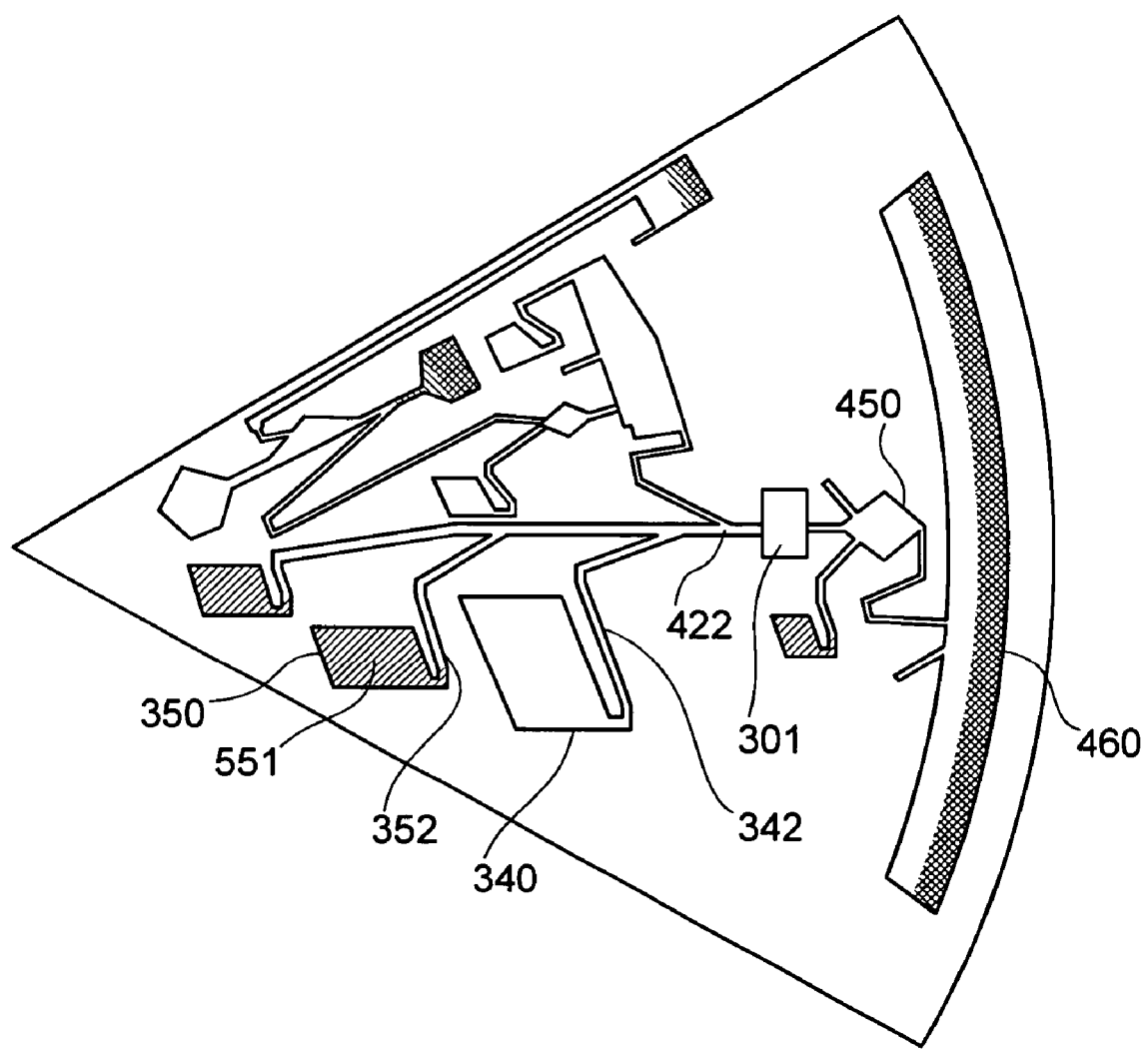
Figure 36:
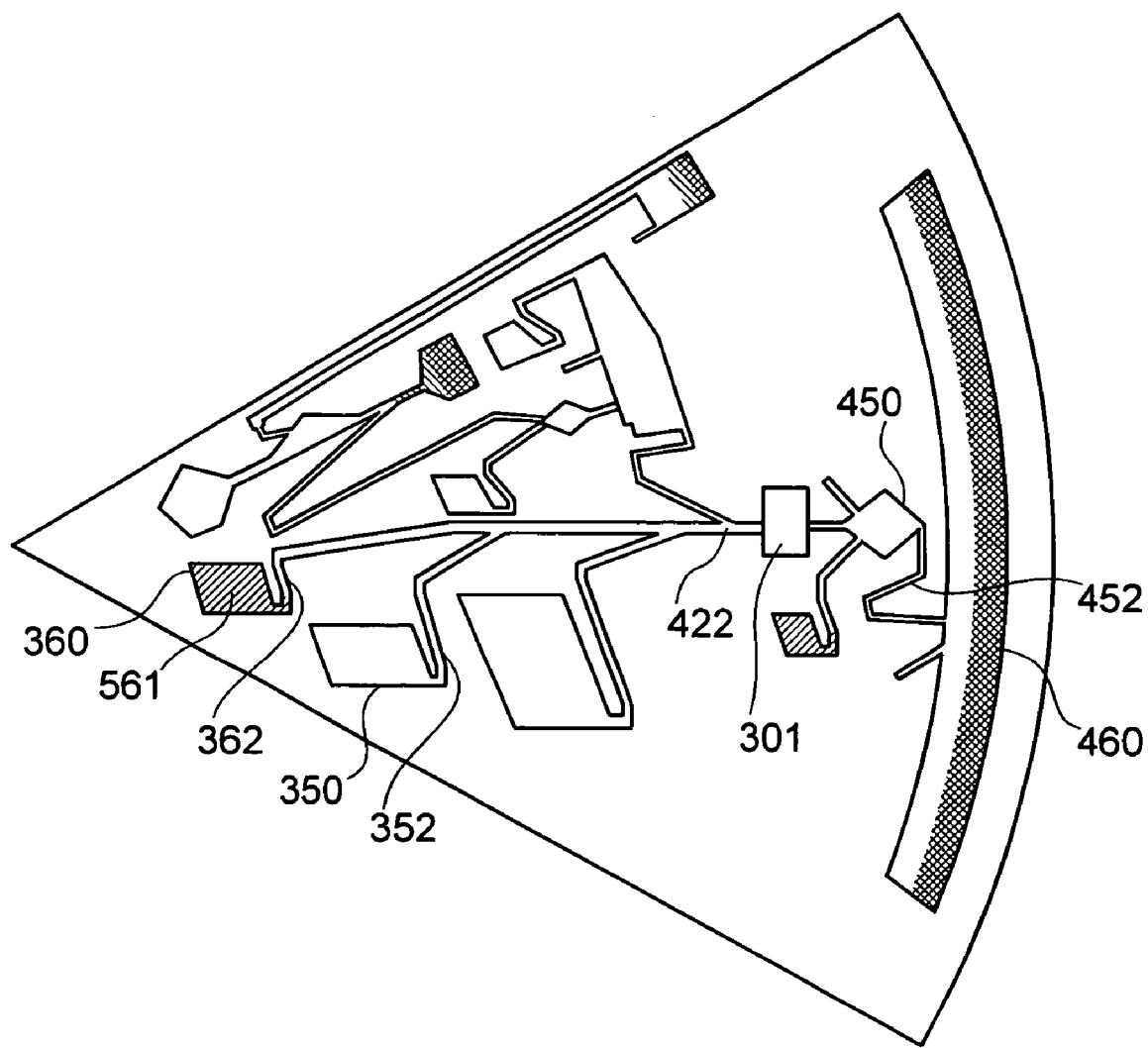
Figure 37:
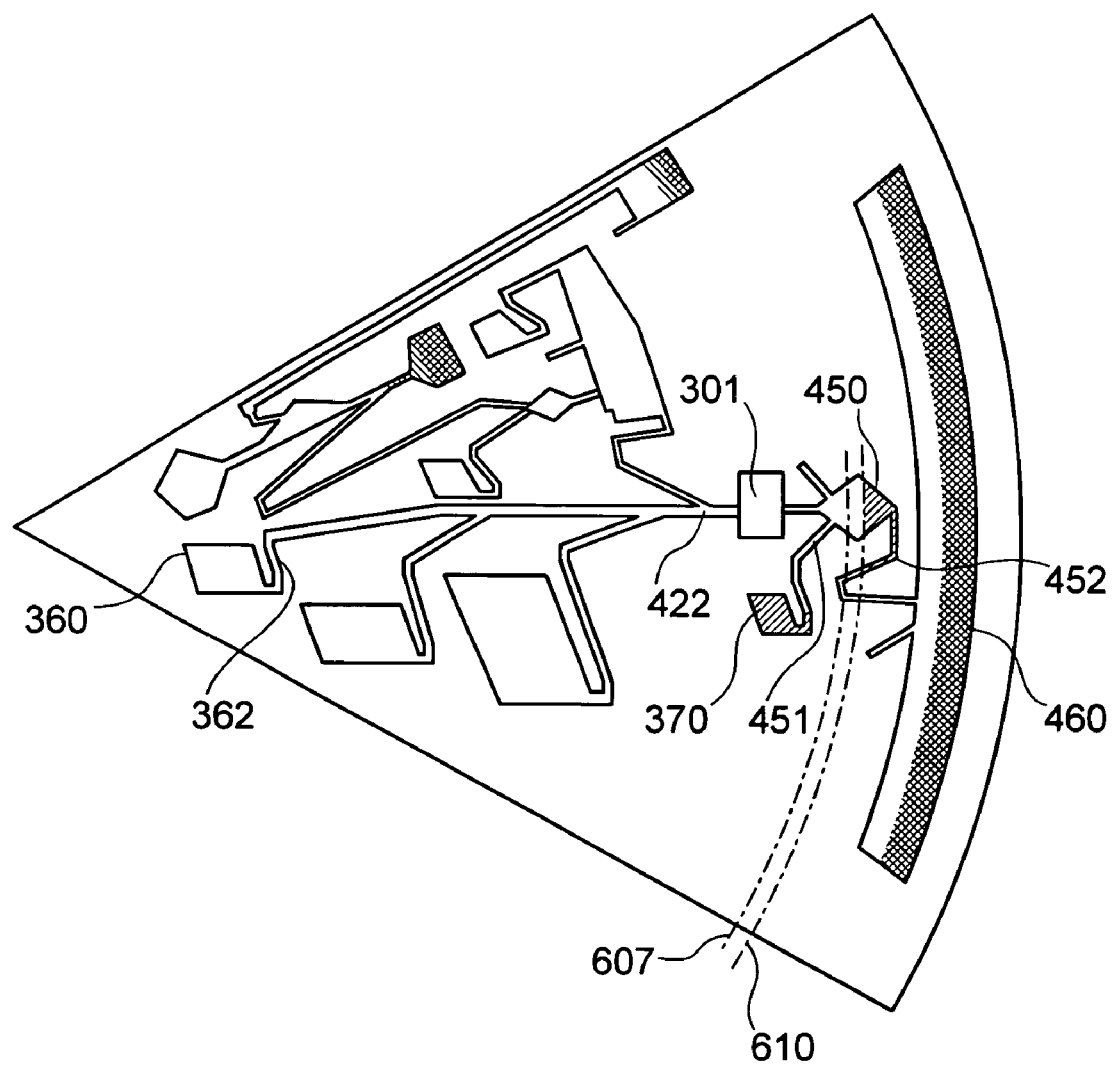
Figure 38:
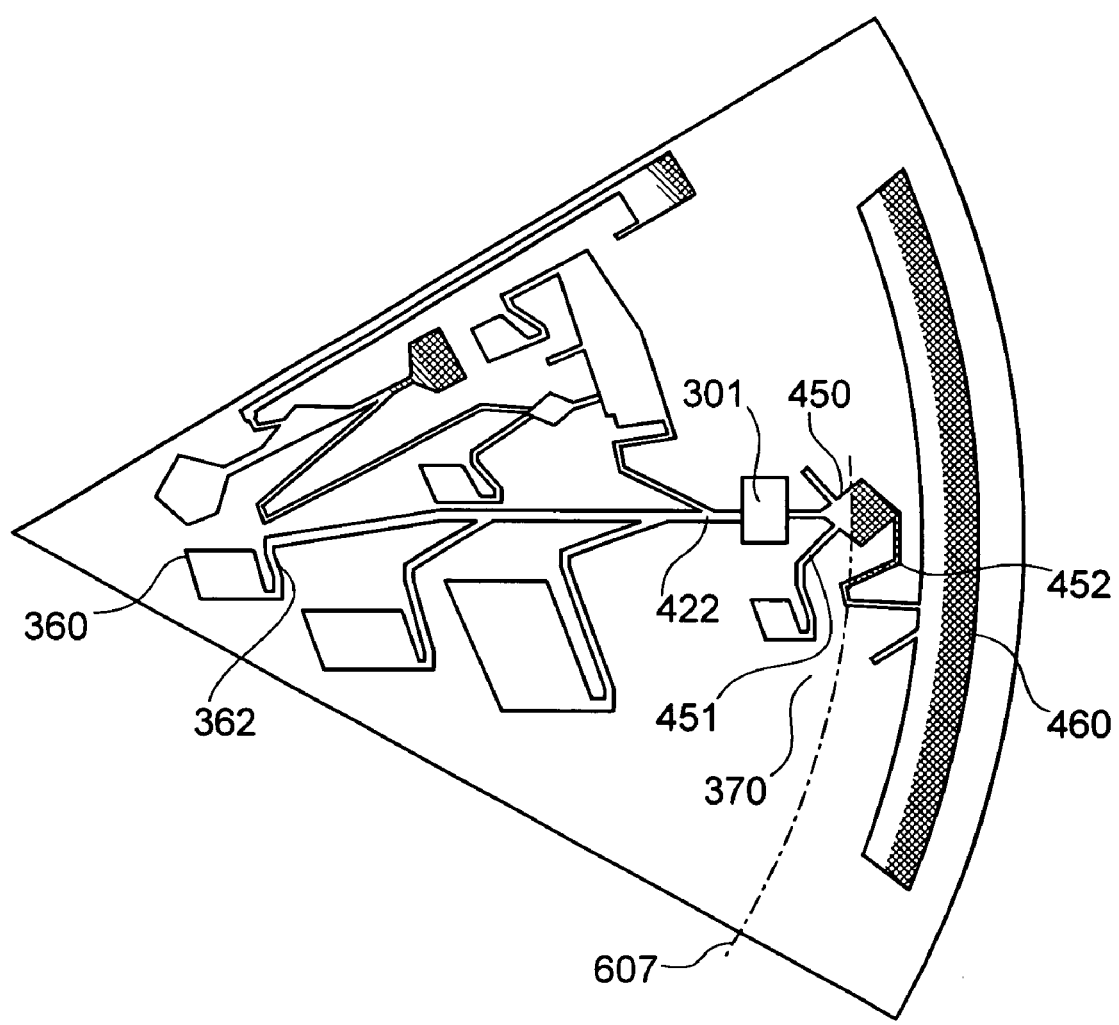
Figure 39:
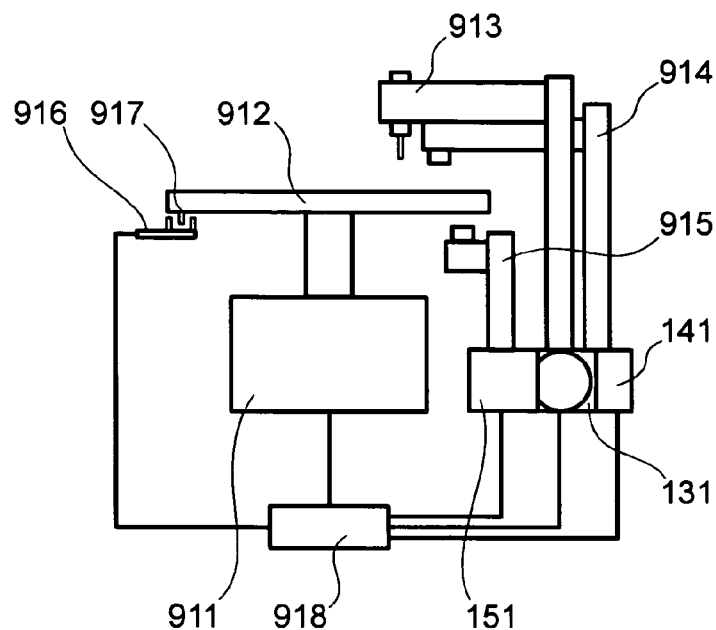

embodiment according to the present invention, in particular, corresponding to the a'-a' cross-section view shown in FIG. 1 mentioned above;

FIG. 18 is the a-a' cross-section view of the disc device, showing a step for collecting the eluting solution in the disc device according to the second embodiment;

FIG. 19 is a plane view for showing the front surface-side of the second-layer disc of the disc device, explaining about the structure of the disc device and the method for refining the nucleic acids, of further other (third; $3^{rd}$) embodiment according to the present invention;

FIG. 20 is a view for showing an outlook of the nucleic acid refining apparatus, into which is applied the disc device according to the present invention mentioned above;

FIG. 21 is a total structure view of a gene analyzing apparatus, according to an embodiment of the present invention;

FIG. 22 is a perspective and explosive view of an analyzer disc of the gene analyzing apparatus mentioned above;

FIG. 23 is a perspective view for showing flow path within the analyzer disc mentioned above;

FIG. 24 is a flowchart for showing flows of extracting and analyzing operations with the analyzer disc mentioned above;

FIG. 25 is also a flowchart for showing flows of extracting and analyzing operations with the analyzer disc mentioned above;

FIG. 26 is a view for showing the flowing condition of the liquid, which contains the sample (i.e., the blood) therein, within a flow passage of the analyzer disc mentioned above;

FIG. 27 is also a view for showing the flowing condition of the liquid, which contains the sample therein, within a flow passage of the analyzer disc mentioned above;

FIG. 28 is further also a view for showing the flowing condition of the liquid, which contains the sample therein, within a flow passage of the analyzer disc mentioned above;

FIG. 29 is further also a view for showing the flowing condition of the liquid, which contains the sample therein, within a flow passage of the analyzer disc mentioned above;

FIG. 30 is further also a view for showing the flowing condition of the liquid, which contains the sample therein, within a flow passage of the analyzer disc mentioned above;

FIG. 31 is further also a view for showing the flowing condition of the liquid, which contains the sample therein, within a flow passage of the analyzer disc mentioned above;

FIG. 32 is further also a view for showing the flowing condition of the liquid, which contains the sample therein, within a flow passage of the analyzer disc mentioned above;

FIG. 33 is further also a view for showing the flowing condition of the liquid, which contains the sample therein, within a flow passage of the analyzer disc mentioned above;

FIG. 34 is further also a view for showing the flowing condition of the liquid, which contains the sample therein, within a flow passage of the analyzer disc mentioned above;

FIG. 35 is further also a view for showing the flowing condition of the liquid, which contains the sample therein, within a flow passage of the analyzer disc mentioned above;

FIG. 36 is further also a view for showing the flowing condition of the liquid, which contains the sample therein, within a flow passage of the analyzer disc mentioned above;

FIG. 37 is further also a view for showing the flowing condition of the liquid, which contains the sample therein, within a flow passage of the analyzer disc mentioned above;

FIG. 38 is further also a view for showing the flowing condition of the liquid, which contains the sample therein, within a flow passage of the analyzer disc mentioned above;

FIG. 39 a view for showing an example of the structure for detecting the rotation position of a holder disc, according to the embodiment mentioned above; and FIG. 40 is a view for showing operational waveforms of examples of operation timings of a drilling machine.

BEST MODE FOR CARRYING OUT THE INVENTION

Hereinafter, explanation will be given on embodiments according to the present invention, by referring to drawings attached herewith.

Herein, first of all, as one embodiment according to the present invention will be explained a disc-type device, which is applied for refining a so-called ribonucleic acid (i.e., RNA), such as, the HCV virus, the HIV virus, etc., included in blood (i.e., whole blood), for example. Explanation will be given on the structure of a device according to the first embodiment, by referring to FIGS. 1 to 7, and in addition thereto, explanation will be given on a method for refining the RNA with use thereof, by referring to FIGS. 8 to 15 and 16. Also, by referring to FIGS. 17 and 18, explanation will be given on the structure of other embodiment (i.e., a second structure) according to the present invention, and a method for refining the RNA with use thereof. Furthermore, by referring to FIG. 19, explanation will be given on the structure of further other embodiment according to the present invention (i.e., a third structure) according to the present invention, and a method for refining the RNA with use thereof, and by referring to FIG. 20 will be explained an apparatus applying the disc device of the present invention therein; thus, the refining apparatus of nucleic acids.

FIG. 1 is a perspective view for showing an outlook of the disc device, constituting a central portion of the refining apparatus of nucleic acids, according to the present invention. The disc device 1 is built up with covers on a front surface side and a reverse surface side, both being in disc-like in the configuration thereof, and further a laminated structure of two (2) layers disposed therebtween. In more details, it is build up with a front surface-side cover 2, a first-layer disc 3, a second-layer disc 4, and a reverse surface-side cover 5. Also, in the front surface-side cover 2 are formed a large number of ports, including a blood inlet port 6 and an eluting solution collection port 13 for collecting the eluting liquid, within a liquid of which the nucleic acids are purified or refined, etc. Further, the disc device 1 is fixed onto a support shaft 50 for use of rotation of the disc device. Further, the support shaft 50 for use of rotation of the disc device is connected to, such as an electric motor, etc., thereby driving the disc device 1 rotationally.

Figure 2:
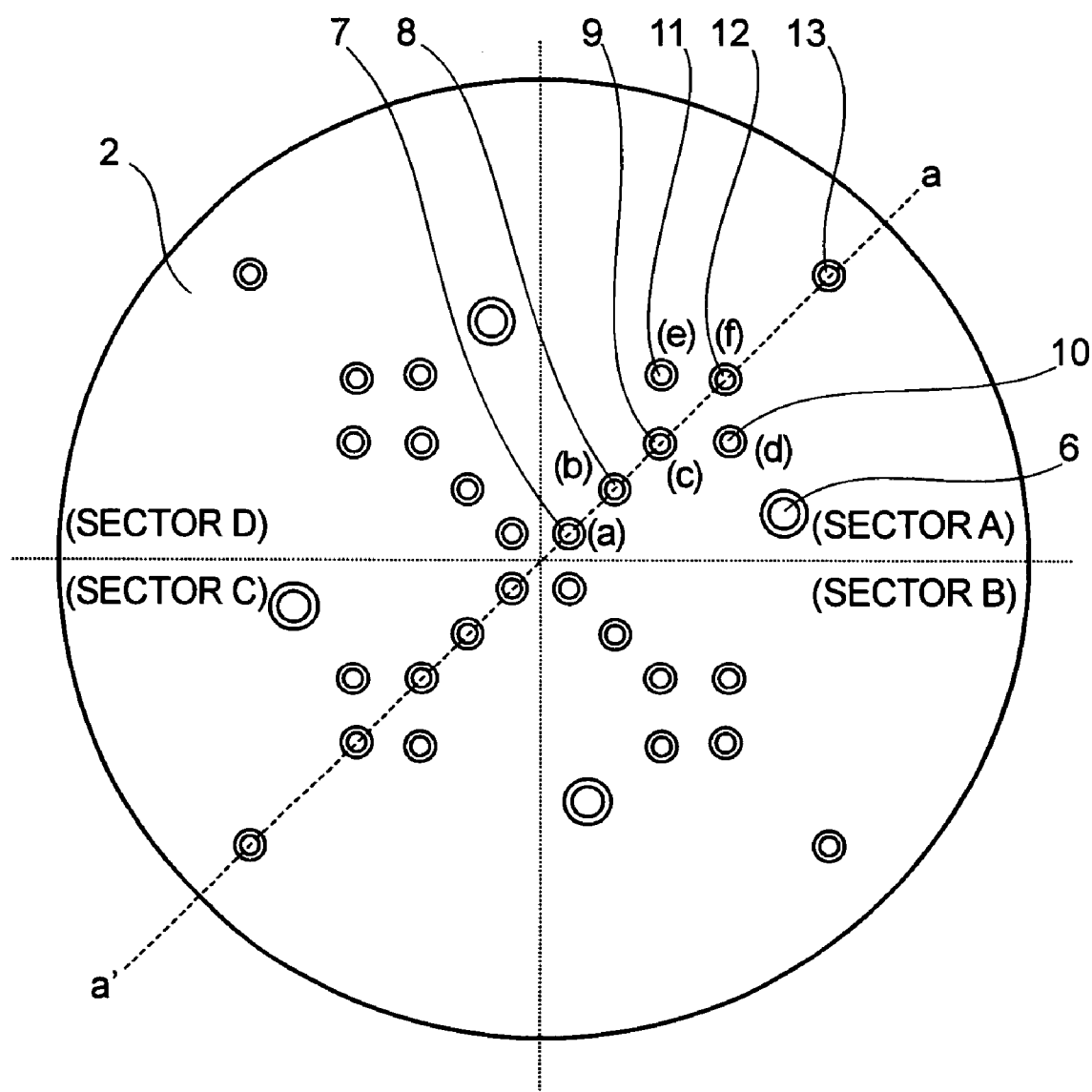
FIG. 2 is a plane view of a cover on a front surface-side thereof, in the disc device according to the present invention.

FIG. 2 shows the plane structure of the front surface-side cover 2, being a constituent part of the disc device 1 mentioned above, according to the present invention. On this front surface-side cover 2, as shown in the figure, are formed four (4) quadrants (4 sectors), being disposed symmetrically in positions, each including a blood inlet port 6, a valve (a) opening port 7, a valve (b) opening port 8, a valve (c) opening port 9, a valve (d) opening port 10, a valve (e) opening port 11, a valve (f) opening port 12, and a port 13 for use of collection of eluting solution, respectively. Further, as is shown in FIG. 2 (also, in the same manner as in FIG. 1), in each of the four (4) quadrants are formed ports a-f, respectively, but detailed explanation will be given only on the ports of the first quadrant (sector A), as a representative one thereof. However, other sectors, i.e., the (sector B), the (sector C) and the (sector D), are also same to that of the sector A, therefore the detailed explanation thereof will be omitted herein.

In FIG. 2, each of the ports, being attached with reference numerals 6-13, is built up with a film-like sheet made of a thick rubber, such as a silicon rubber, etc., for example, being stuck or firmly fixed with an adhesive or the like, thereby forming a cover through deposing it into bores formed on the front surface-side cover 2. However, a needle is stuck through the rubber onto the film-like sheet, on which that rubber is fixed, and thereafter, in a case where the needle is pull out, the opening portion formed by sticking of the needle is closed up with the self-restoring force due to elasticity, which is inherently owned by the rubber. For this reason, there is no chance that the liquid remaining within the disc device 1 during the rotation of the disc device 1 comes out from the opening portion to be scattered into an outside thereof.

Figure 3:
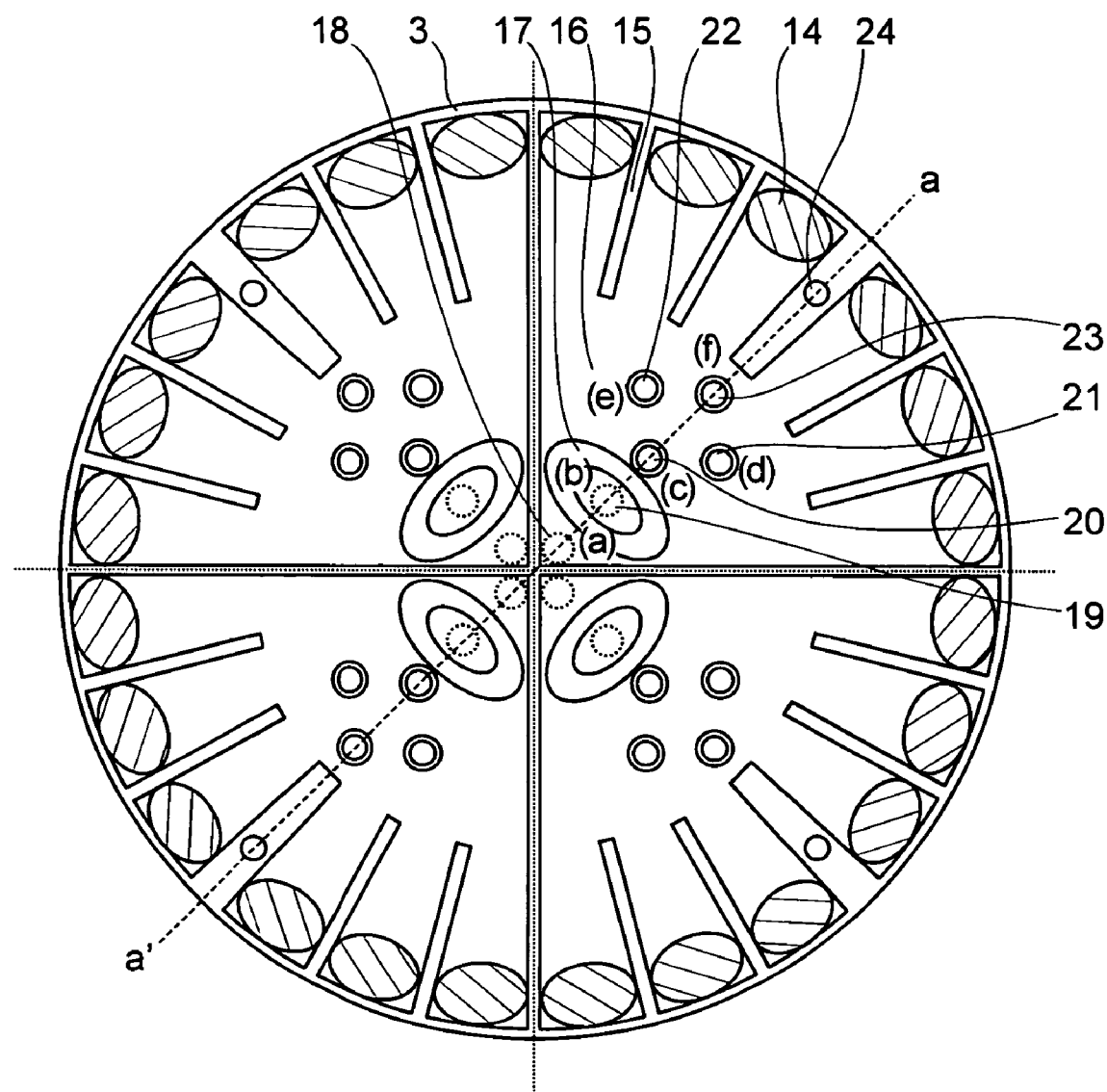
FIG. 3 is a plane view of a first ($1^{st}$) layer disc on a front surface-side thereof, in the disc device according to the present invention.

FIG. 3 shows the plane structure of the first-layer disc 3, as a constituent of the disc device 1 mentioned above, according to the present invention. This first-layer disc 3 is partitioned symmetrically, thereby to form four (4) chambers (sectors A to D), being similar in the shape thereof, as shown in the figure. In each of those chambers are provided a hollowed separation air gap 16 formed, a gutter (a recess portion) 17, being formed in one body together with the separation air gap 16 but hollowed deeper than that, and plural partition walls 15, each having the same height to that of the outer periphery portion of the disc (herein, each chamber has five (5) pieces of walls, thereby being divided into six (6) small chambers). Within each of the small chambers in about "U" shape, being defined between the partition wall 15 and the outer periphery portion mentioned above, a gel 14 is provided therein, respectively (i.e., six (6) gels in each chamber), and also a valve (a) 18 for use of transferring the serum in excess and a valve (b) 19, which are formed on the bottom of the gutter 17, for use of transferring the serum accumulated within the gutter 17 are provided in the center of the first-layer disc 3. In a middle portion thereof are formed a needle insertion bore 20 for opening the valve (c), a needle insertion bore 21 for opening the valve (d), a needle insertion bore 22 for opening the valve (e), and a needle insertion bore 23 for opening the valve (f), i.e., provided as those separated from the separation air gap 16, and also a tip insertion bore 24 for collecting the solution in a part of the partition wall 15.

As was mentioned in the above, with the disc device 1 according to the embodiment of the present invention, since four (4) chambers (an eluting chamber) are provided separately, within an inside thereof, it is possible to introduce four (4) kinds of bloods at the same time. However, the number of those eluting chambers should not be restricted only thereto, but it may be less or grater than that. Also, the valves (a) 18 and (b) 19 are those, which are normally closed in the condition thereof. Further, those valves are formed in one body together with the first-layer disc 3 and those portions are formed to be very thin in the thickness thereof, comparing to the other portions (however, explanation will be given later on the cross-sectional construction of the disc).

Figure 4:
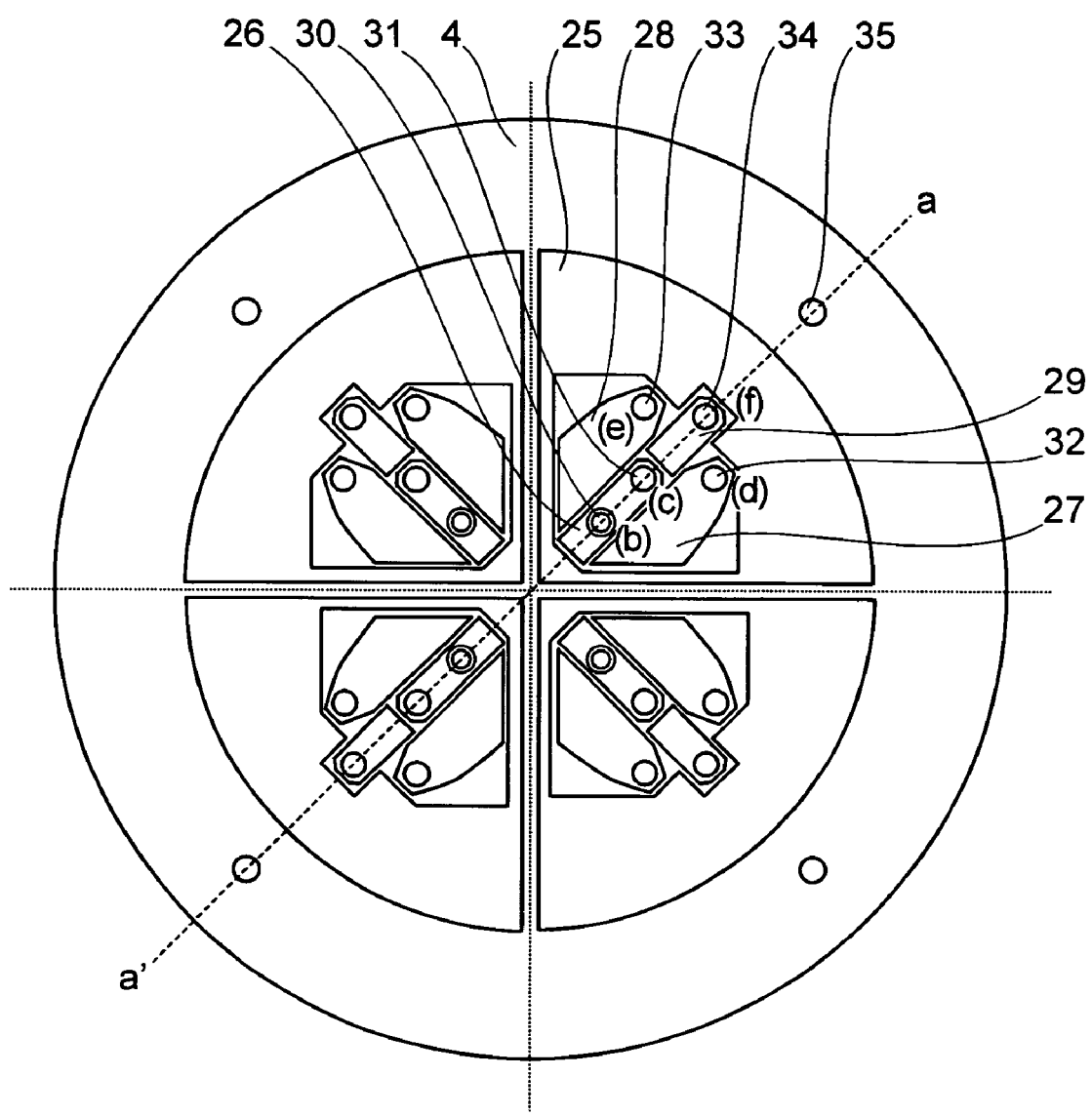
FIG. 4 is a plane view of a second ($2^{nd}$) layer disc on a front surface-side thereof, in the disc device according to the present invention.

FIG. 4 shows the structure on a front surface-side of the second-layer disc 4, being the constituent part of the disc, according to the present invention. In this second-layer disc 4, in the same manner as in the first-layer disc 3 mentioned above, the chambers (the sectors) are partitioned symmetrically, thereby forming four (4) chambers being same in the shape thereof. And, in each of the chambers (the sectors) are provided an excess serum reservoir 25 for introducing the excess serum in separating operation of blood cells, a combining liquid reservoir 26 for accumulating a combining liquid (a reagent for combining the nucleic acid contained within the blood serum with the solid phase), which is provided in a central portion of the excess serum reservoir 25, reservoir 27 for a rinsing liquid A and reservoir 28 for a rinsing liquid B for accumulating rinsing liquids (a rinsing liquid A and a rinsing liquid B: reagents for rinsing the dirty solid phase attaching components thereon, including protein components contained within the blood serum and the combining liquid, without taking out the nucleic acid combining on said the solid phase therefrom), and an eluting solution reservoir 29 for accumulating the eluding liquid (a reagent for eluting the nucleic acid combining onto the solid phase), respectively.

And, on this second-layer disc 4 are also provided a serum penetration opening 30, through which moves the blood serum obtained by means of the first-layer disc 3, in an inner peripheral direction thereof, and a valve (c) 31 for transferring the combining liquid, within the combining liquid reservoir 26 in the outer peripheral direction thereof. Further, within the reservoir 27 for rinsing liquid A, a valve (d) 32 is provided for transferring the rinsing liquid A remained within the reservoir 27 of rinsing liquid A, in the outer peripheral direction thereof, and also within the reservoir 28 for rinsing liquid B, a valve (e) 33 for transferring the rinsing liquid B remained within the reservoir 28 for rinsing liquid B, in the outer peripheral direction thereof.

Also, within the eluting solution reservoir 29, there is provided a valve (f) 34 for transferring the eluting liquid, in the outer periphery direction thereof, and in the outer periphery portion of the disc is formed a tip insertion portion 35 for use of collecting the eluting liquid, being connected with the tip insertion bore 24 for use of collection of eluting liquid, which is formed in the first-layer disc 3 mentioned above.

As mentioned above, with the disc device 1, according to the present invention, also four (4) chambers are formed in the second-layer disc 4, locating below the first-layer disc 3, corresponding to those in the first-layer disc 3. Also, the valve (c) 31, the valve (d) 32, the valve (e) 33, and the valve (f) 34 are in the closed condition, normally. Further, those valves are formed together with the second-layer disc 4 in one body, and those portions are very thin in the thickness thereof, comparing to the other portions.

Figure 5:
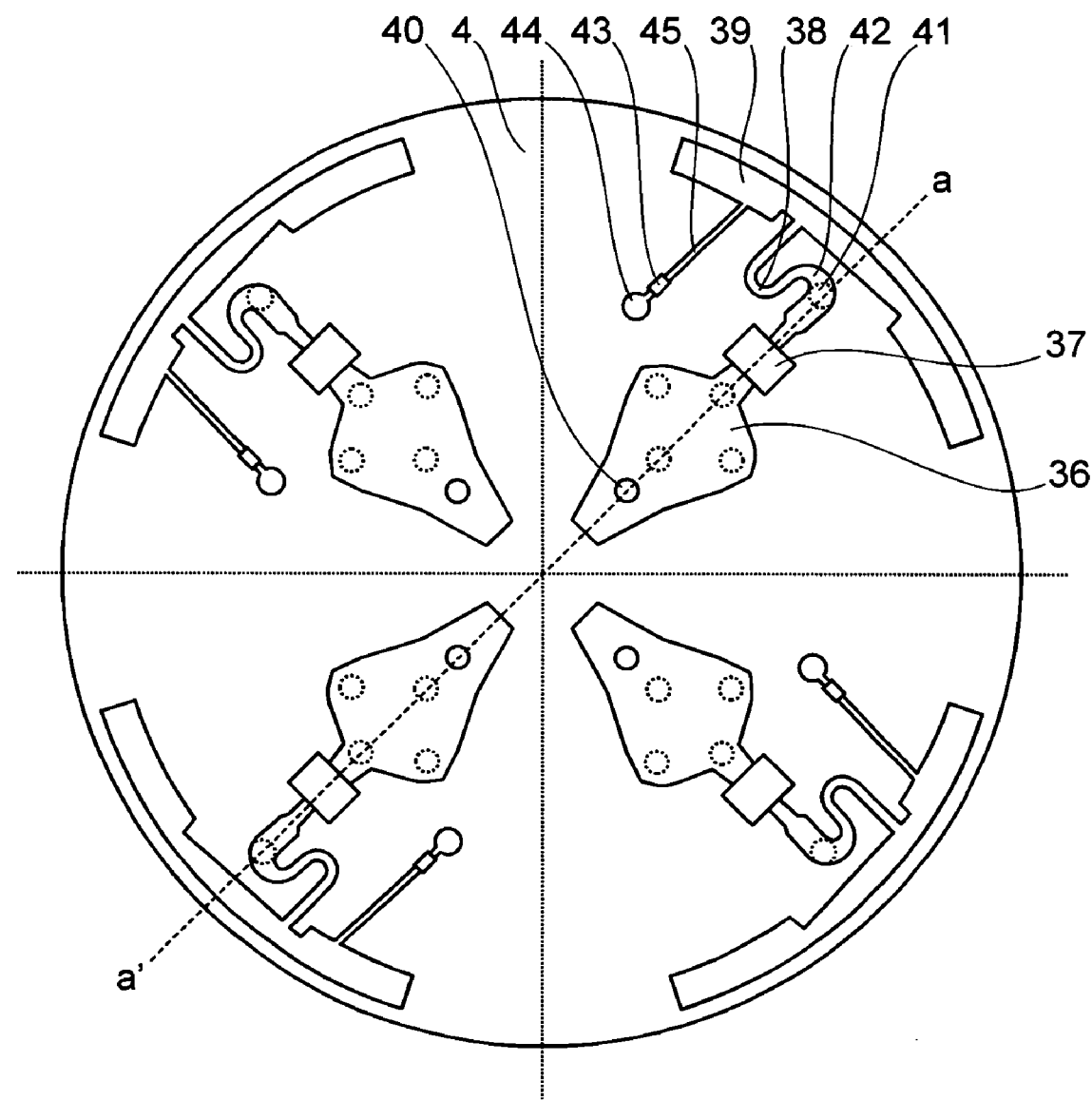
FIG. 5 is a plane view of the second ($2^{nd}$) layer disc on a reverse surface side thereof, in the disc device according to the present invention.

FIG. 5 shows the structure on the reverse side surface of the second-layer disc 4 mentioned above, as the constituent element of the disc device 1 according to the present invention. On the reverse side surface of the second-layer disc 4, as shown in the figure, there are provided a serum discharge outlet 40, through which a quantified blood serum can flows out, and flow passages 36 for achieving a role of transferring the rinsing liquid A, the rinsing liquid B and the eluting liquid, respectively. Also, on the reverse side surface of the second-layer disc 4 is provided a carrier 37 made of high-density silica, as the solid phase for combining with the nucleic acid, through which are transferred the mixture between the blood serum and the combining liquid, the rinsing liquid A and the rinsing liquid B, while a valve 41 for use of collecting the eluting liquid is provided in the reservoir of collected eluting liquid, which is formed in a part thereof, for maintaining the eluting liquid therein. Further, there are also provided a flow passage 38 formed in "U" shape, through which passes the mixture of the blood serum and the combining liquid, the rinsing liquid A and the rinsing liquid B, a waste liquid reservoir 39 for accumulating the mixture of the blood serum and the combining liquid, the rinsing liquid A and the rinsing liquid B therein, and a flow passage 45 for use of removing air, being provided for discharging the air remaining within the waste liquid reservoir 39.

Also, in each chamber (the sector) formed on the reverse side surface of the second-layer disc 4 are provided a trap, provided for prohibiting the components, such as, the serum, the combining liquid, the rinsing liquid A, the rinsing liquid B, etc., from scattering in the form of mist thereof into an outside of the disc 1, i.e., as a mist scattering prevention filter 43, formed in a part thereof, and an outer connecting hole 44 being connected to an outside of the disc device 1, respectively.

Figure 6:
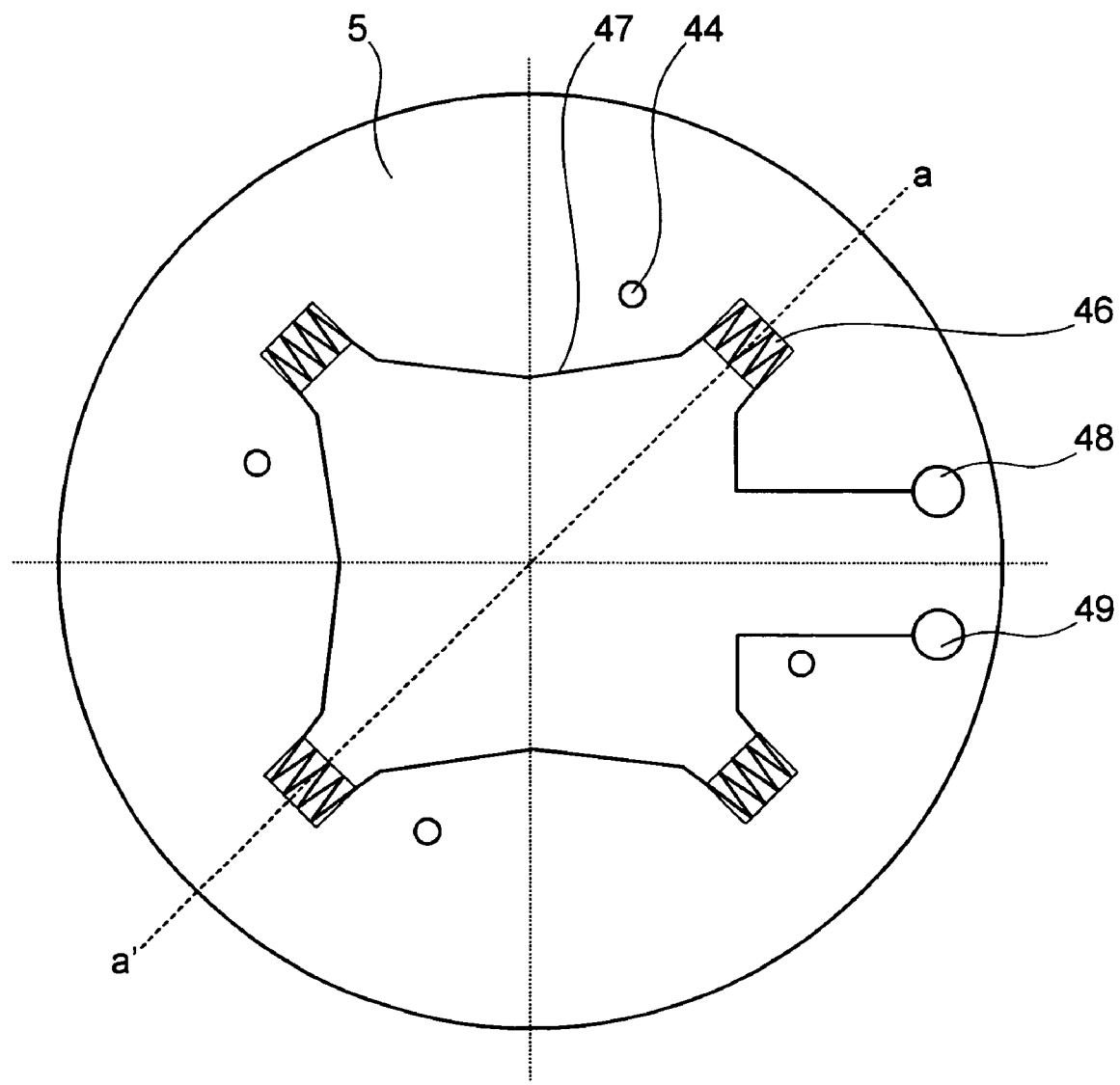
FIG. 6 is a plane view of the cover on a reverse surface side thereof, in the disc device according to the present invention.

FIG. 6 shows the structure on a front surface-side cover 5, as the constituent part of the disc device 1, according to the present invention. On the front surface-side cover 5, as shown in the figure, is formed an outer connection bore 44 at the same position to that of the second-layer disc 4. Also at the position corresponding to the carrier 37 provided on the second-layer disc 4 mentioned above, in particular below there, resistors 46 for use of heating the carrier are disposed, each of which generates heat due to conduction of current therethrough, thereby heating up the region or area of the carrier 37 up to a predetermined temperature. Further, there are provided wirings 47 for connecting those resistors for use of heating the carrier, electrically in series, and also electrode pads for connecting with outer terminals of the disc device 1, being made up with so-called a plus (+) electrode 48 and a minus (−) electrode 49, for conducting the electricity through the four (4) resistors 46 for heating the carrier.

Figure 7:
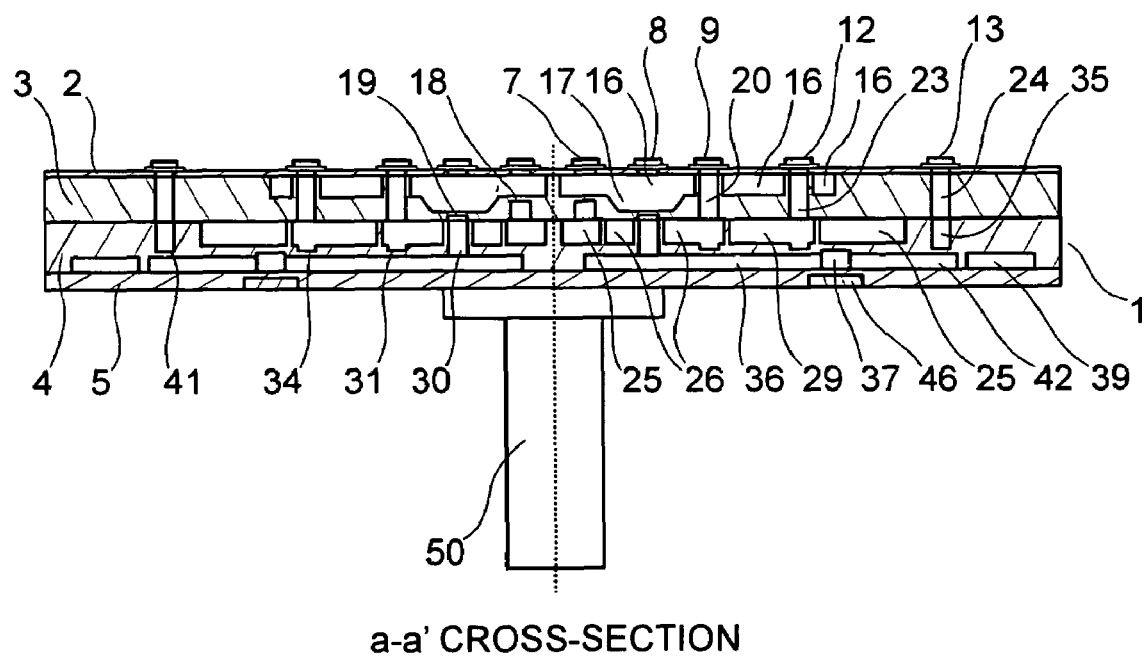
FIG. 7 is an a-a' cross-section view of the disc device shown in FIG. 1 mentioned above.

Next, the cross-section views of the disc 1 mentioned above are shown, by referring to FIGS. 7, 9, 10, 11, 12, 14, and 15. FIG. 7 shows the a-a' cross-section view of the disc device 1 shown in FIG. 1 mentioned above. Also, FIG. 7 corresponds to the a-a' cross-section views shown in FIGS. 2, 3, 4, 5, and 6 mentioned above, respectively. Namely, the disc device 1 is made up with lamination of the front surface-side cover 2, the first-layer disc 3, the second-layer disc 4, and the reverse surface-side cover 5, in that order thereof. In more details, the disc device 1 is built up by laminating those, i.e., the front surface-side cover 2 shown in FIG. 2 mentioned above, the first-layer disc 3 shown in FIG. 3 mentioned above, the second-layer disc 4 shown in FIG. 4 mentioned above, the reverse-side of the second-layer disc shown in FIG. 5 mentioned above, and the reverse surface-side cover 5 shown in FIG. 6 mentioned above, in that order, sequentially.

On the a-a' cross-section of the front surface-side cover 2 in FIG. 7 are formed an opening port 7 of the valve (a), an opening port 8 of the valve (b), an opening port 9 of the valve (c), an opening port 12 of the valve (f), and a collection port 13 for eluting liquid, respectively. Also, on the first-layer disc 3, the cross-section of which is shown in this a-a' cross-section view, are provided a separation gap 16 gutter 16 formed with a gutter 17, a valve (a) 18, and a valve (b) 19, and further are formed a needle insertion bore 20 for use of opening the valve (c), being provided with connecting to the opening port 9 of the valve (c), a needle insertion bore 23 for use of opening the valve (f), being provided with connecting to the opening port 12 of the valve (f), and a tip insertion bore 24 for use of collecting the eluting liquid, being provided with connecting to the collecting port 13 of the eluting liquid, respectively.

Also on the second-layer disc 4, shown in a-a' cross-section view, are provided and/or formed an excess serum reservoir 25, a combining liquid reservoir 26, an eluting solution reservoir 29, a serum penetration opening 30, a valve (c) 31, a valve (f) 34, a tip insertion portion 35 for collecting the eluting liquid, being provided with connecting to the tip insertion portion 24 for use of collecting the eluting liquid, a flow passage 36 for mixing, a carrier 37, a waste liquid reservoir 39, a valve 41 for use of collecting the eluting liquid, and a collected eluting liquid reservoir 42, respectively.

On the reverse side-surface cover 5 shown in a-a' cross-section view is formed the resistors 46 for heating the carrier. Further, the disc device 1, being built up by fixing the above-mentioned front surface-side cover 2, the first-layer disc 3, the second-layer disc 4, and the reverse surface-side cover 5, is fixed, connecting onto a supporting shaft 50 for rotating the disc device. In more details, this disc device 1 is fixed, connecting onto the supporting shaft 50, so that the center thereof comes to be on the central axis of rotation of the supporting shaft 50 for rotating the disc device.

The disc device 1 is built up with such structure as mentioned above. However, also herein, other structures, such as the valve (a) 18, the valve (b) 19, the serum penetration opening 30, the valve (c) 31, the valve (f) 34, and the valve 41 for collecting the eluting liquid, for example, are explained only in the portion of the sector C, for escaping from duplicate of explanation thereof. However it is needless to say that they are totally same with, at the position corresponding thereto the sector A.

Next, explanation will be given on a method for purifying or refining nucleic acids from a sample, in more details, for refining the RNA of the HCV virus, HIV virus, etc., from blood, by using the disc device 1, the structure of which was explained in the above.

Figure 8:
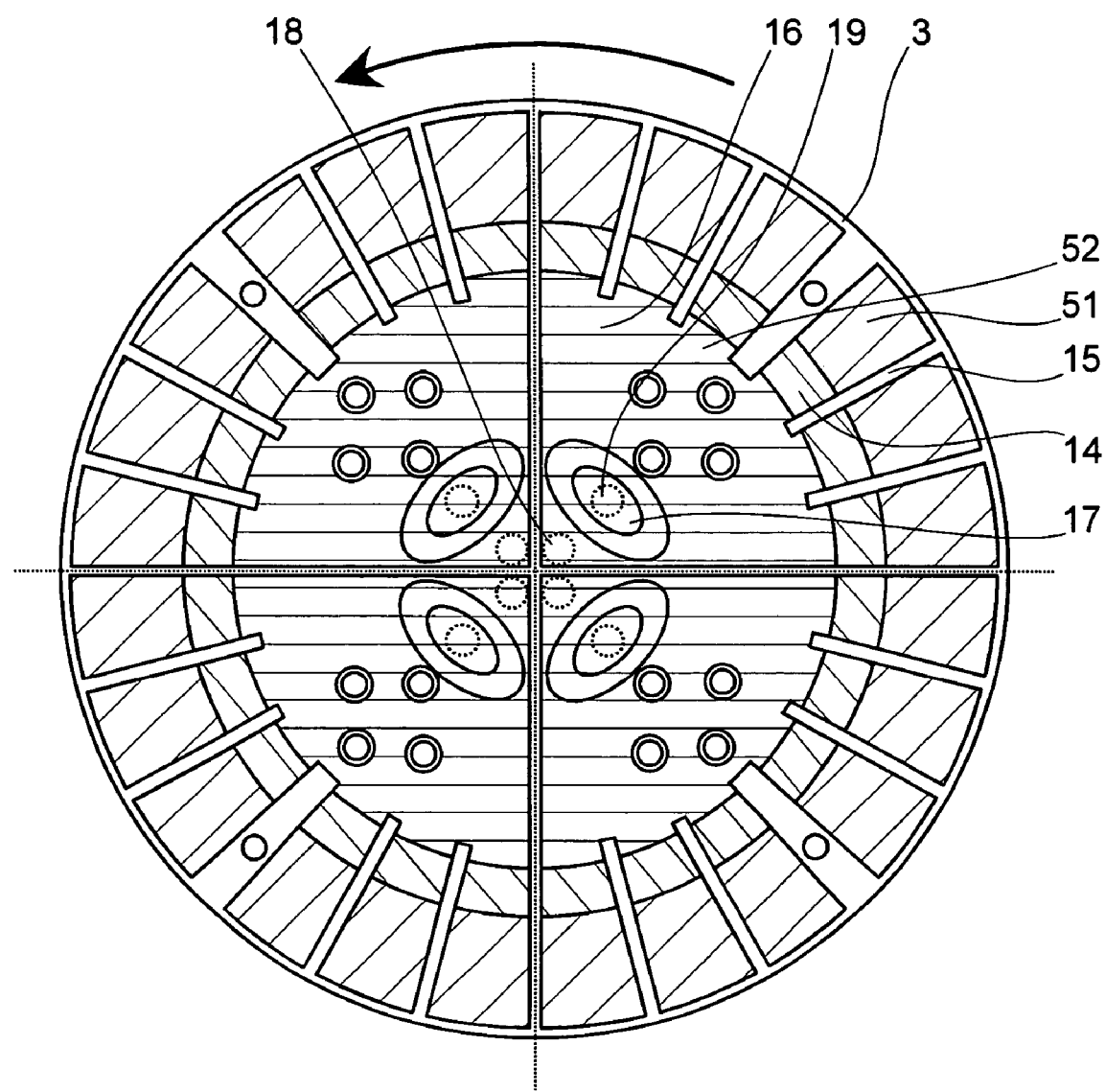
FIG. 8 is a plane view of the first-layer disc mentioned above, showing a step for separating blood serum from blood with using a gel, in the disc device according to the present invention.

First of all, explanation will be made on a step for separating the serum from the blood by using the disc device 1. FIG. 8 shows the standstill condition of the first-layer disc 3, where it is stopped in rotation, after injecting the blood containing the target virus therein into the inside of the first-layer disc 3 by sticking the needle tube into the blood insertion port 6 on the front surface-side cover 2, and rotating the disc device 1 by the motor for about five (5) minutes so as to generate the centrifugal force of around 2,000 G.

Under this condition, in each chamber, so-called a blood cells 51, including a red corpuscle, which is the highest density, and/or a white corpuscle, etc., fills up the outermost periphery portion, within the separation gap 16 thereof. On the other hand, the blood serum 52 including the virus therein fills up the gutter 17 provided within the separation gap 16 at the central portion of the disc, thereby being in a relationship of disposition where the gel 14 lies between them. This is because the blood is separated by the centrifugal force applied thereupon, due to the rotation of the disc device 1. In more details, because the density of the gel 14 is lower than that of the blood cells 51 and is higher than that of the serum components including the virus, therefore the blood cells 51, where the centrifugal force is applied, shifts or moves to the outermost periphery portion thereof, forcedly passing through an inside of the gel 14, which is provided on the outermost periphery portion of the separation gap 16 mentioned above.

Further, since no such the power is applied onto the blood cells 51 or the like, any more, corresponding to the centrifugal force applied by the rotation, when the disc device 1 is stopped in the rotation thereof, therefore none of the blood cells 51 or the like passes through within the gel 14, thereby moving to the central portion of the disc. For this reason, the blood cells 51 or the like will never be mixed up with the serum 52 containing the virus therein, even when the disc device 1 is stopped in the rotation thereof. However, it is preferable to determine the length of the said partition wall 15 in advance, so that the gel 14 will stop at a predetermined position of the partition wall 15 after completing the series of operations of rotation/stopping with respect to the disc device 1.

Figure 9:
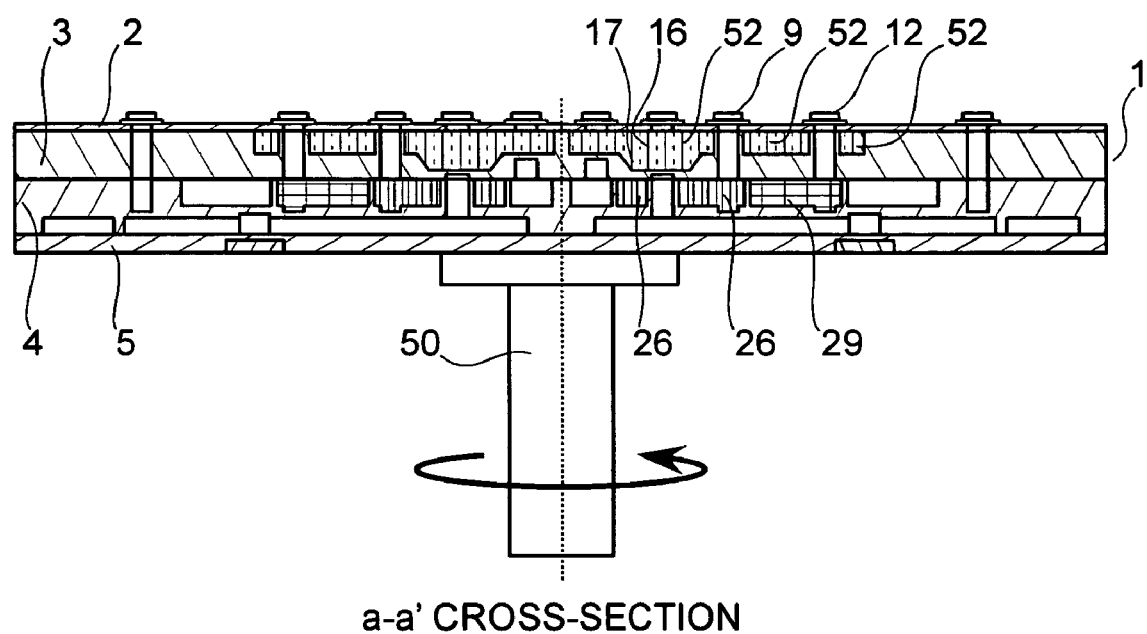
FIG. 9 is the a-a' cross-section view of the disc device shown in FIG. 1 mentioned above, showing the condition of separation of the blood serum from blood.

FIG. 9 shows the a-a' cross-section of the disc device 1, under the condition shown in FIG. 8 mentioned above. Within the separation gap 16 of the firs-layer disc 3 is filled up the serum 52 containing the target virus therein, and within the gutter 17 is also filled up the serum 52, in the same manner. Also, within the combining liquid reservoir 26 is filled up the combining liquid, and further within the eluting solution reservoir 29 is filled up the eluting solution. Further, though not shown in this FIG. 9, within the rinsing liquid A reservoir 27 is filled up the rinsing liquid A, and within the rinsing liquid B reservoir 28 is filled up the rinsing liquid B. Herein, the combining liquid, the eluting solution, the rinsing liquid A, and the rinsing liquid B are held within the second-layer disc 4 in advance, however the present invention should not be restricted onto to such the structure. For example, the combining liquid, the eluting solution, the rinsing liquid A, and the rinsing liquid B may be injected into the combining liquid reservoir 26, the eluting solution reservoir 29, the rinsing liquid A reservoir 27, and the rinsing liquid B reservoir 28 mentioned above, through an external mechanism, such as a pipette attached with a needle tube, for example, through the valve (c) opening port 9, the valve (f) opening port 12, the valve (d) opening port 10 (not shown in the figure), or the valve (e) opening port 11 (not shown in the figure), respectively and/or every time, depending upon the necessity or corresponding to the processing thereof.

Figure 10:
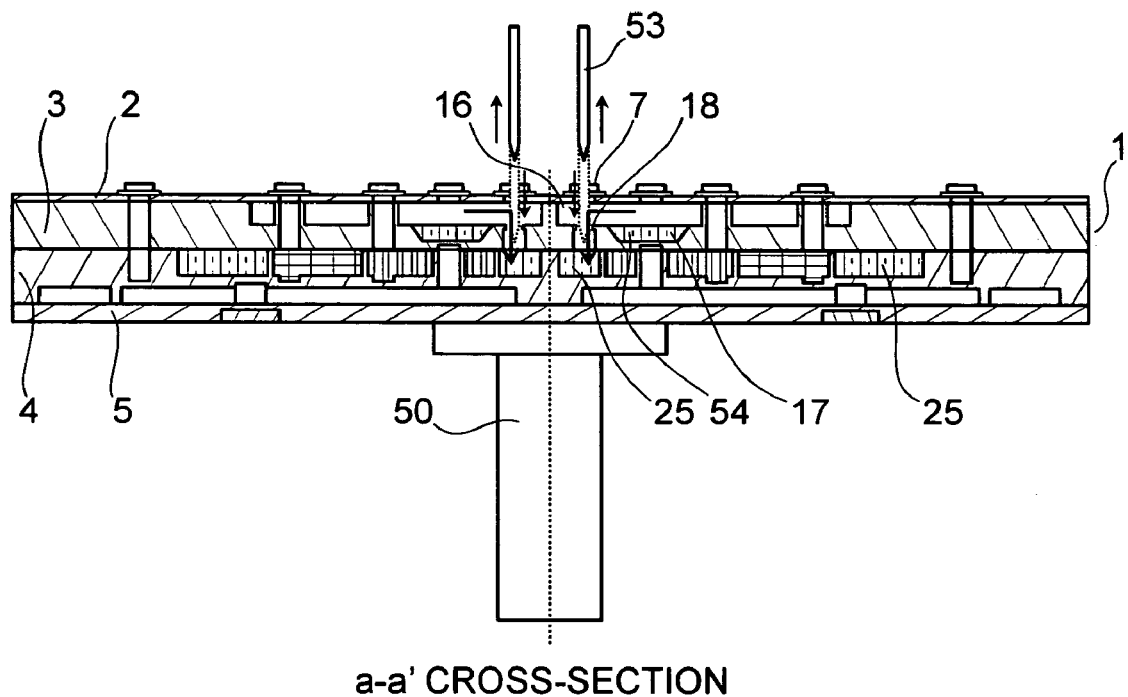
FIG. 10 is the a-a' cross-section view of the disc device shown in FIG. 1 mentioned above, showing a step for removing the blood serum in excess.

Next, FIG. 10 is a view for explaining the processing for transmitting the serum other than the necessary amount thereof into the excess serum reservoir 25 provided in the second-layer disc 4, with using a needle 53. This processing is as follows:

(1) The needle 53 is inserted into the disc 1 stopped in the rotation thereof, through the valve (a) opening port 7;

(2) The needle 53 is pulled out after breaking through the valve (a) 18 with that needle 53; and (3) The serum in excess flows into the excess serum reservoir on the second-layer disc 4.

At the same time, the serum is accumulated within the gutter 17 provided in the separation gap 16, in the necessary amount thereof.

By the process as mentioned above, the quantified serum can be obtained in the necessary amount thereof, and on the other hand, the serum in excess is discharged to an outside of the first-layer disc 3. However, the valve (a) opening port 7, which was opened once through sticking of the needle 53, will be closed up through the self-restoring force due to the elasticity of that rubber, as mentioned above. Also, the volume of the gutter 17 is determined to become the volume, where the serum can enters therein in the necessary amount in advance.

Figure 11:
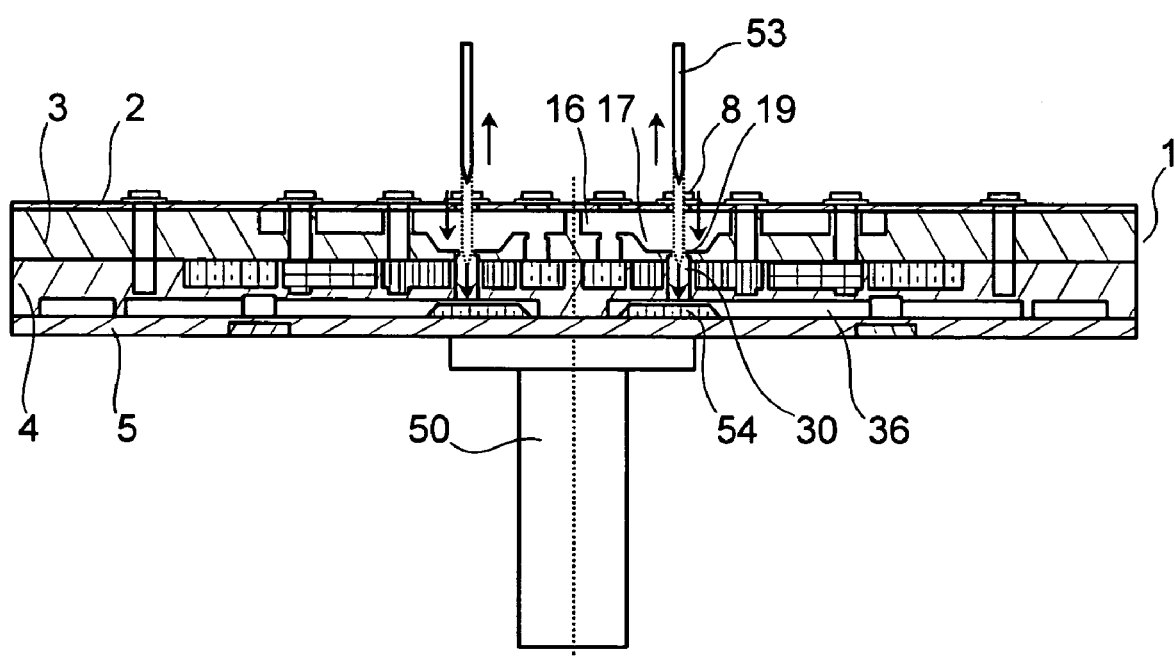
FIG. 11 is the a-a' cross-section view of the disc device shown in FIG. 1 mentioned above, showing a step for taking out the blood serum which is quantified.

Next, FIG. 11 is a view for explaining the processing for transmitting the necessary amount of serum containing the virus therein from the first-layer disc 3 to the mixture flow passage 36 provided in the second-layer disc 4, with using the needle 53. This process is as follows:

(1) The needle 53 is inserted into the disc 1 through the valve (b) opening port 8;

(2) The needle 53 is pulled out after breaking through the valve (b) 19 with that needle 53; and (3) By means of the gutter 17 provided in the separation gap 16, the quantified serum 54 containing the virus therein passes through serum penetration opening 30, and flows into the mixture flow passage 36 on the second-layer disc 4, thereby accumulating therein.

By the process mentioned above, the quantified serum 54 is transferred into the mixture flow passage 36. However, also the valve (b) opening port 8, which was opened once through sticking of the needle 53, will be closed up through the self-restoring force due to the elasticity of that rubber.

Figure 12:
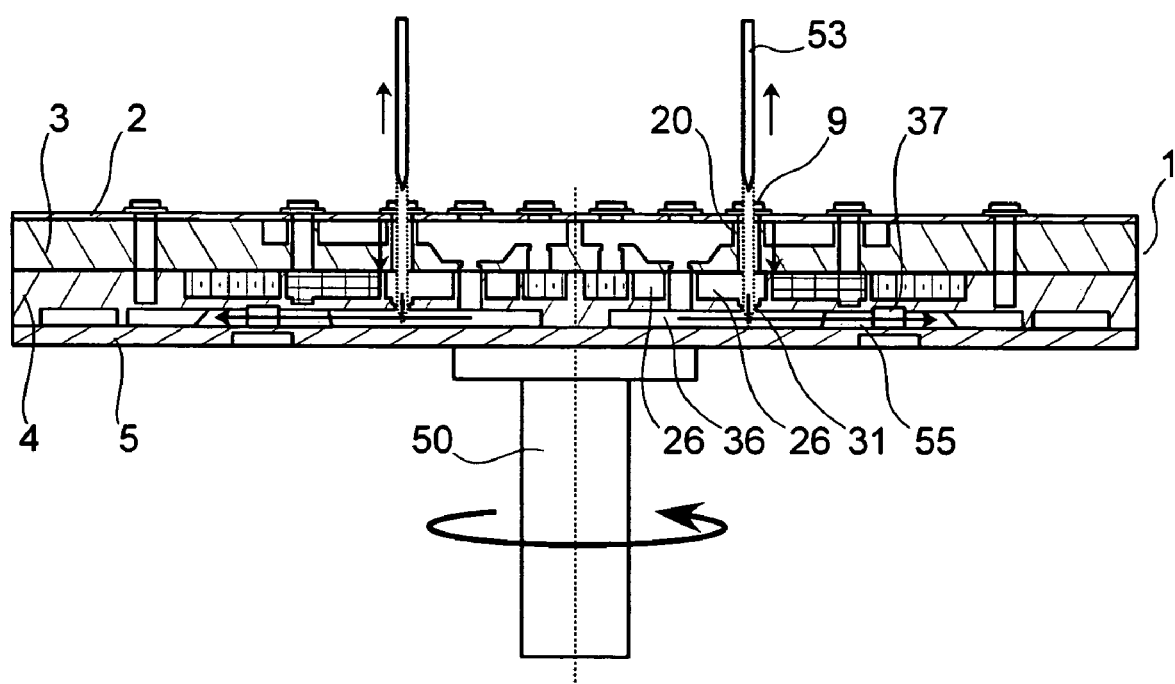
FIG. 12 is the a-a' cross-section view of the disc device shown in FIG. 1 mentioned above, showing a step for passing or penetrating a mixture, mixing up the quantified blood serum and a combining liquid therein, through a carrier.

Next, FIG. 12 is a view for explaining the process for eluting the virus into the mixture obtained by mixing the quantified serum 54 containing the virus therein (but, not shown in this FIG. 12) and the combining liquid (not shown in the figure), producing the mixture liquid 55 into which the RNA of that virus is eluted, and further penetrating that mixture liquid through the carrier 37 made of the high density silica through the centrifugal force, thereby catching or capturing the RNA of that virus eluted by combining it with the carrier 37. Further, this processing is as follows:

(1) The needle 53 is inserted into the disc device 1 through the valve (c) opening port 9;

(2) The needle 53 passes trough the valve (c) opening needle insertion bore 20, thereby breaking through the valve (c) 31. And, the needle 53 is pulled out;

(3) The combining liquid held within the combining liquid reservoir 26 flows into the mixture flow passage 36. In this instance, the disc device 1 is rotated at a low rotation speed, to generate such an amount of centrifugal force, that the mixture liquid of the quantified serum 54 containing the virus therein and the combining liquid cannot pass through the carrier 37. With this, the combining liquid within the combining liquid reservoir 26 passes through the valve (c) 31 due to this centrifugal force, and all of it flows down into the mixture flow passage 36;

(4) For mixing up the quantified serum 54 with this combining liquid, upon the disc device 1 is given a rotation in the forward/reverse direction, periodically, for a certain time period, such as several seconds, for example. With such the operation of the disc device 1 as was mentioned above, the combining liquid and the quantified serum 54 containing the virus therein are mixed up, thereby producing the mixture liquid 55 into which RNA of the virus is eluted; and (5) Upon this mixture liquid 55 is applied the centrifugal force, so that it can pass through the carrier 37 made of the high density silica, such as about 30,000 G, for example. Since this carrier 37 made of silica is high in the density, it is high in the ratio of contact, and therefore the RNA can be easily caught or captured with the carrier only if the mixture liquid 55 containing the RNA therein passes therethrough.

By the process as mentioned above, the mixture liquid 55 containing the RNA therein passes through the carrier 37 made of high density silica, thereby capturing the RNA by means of the carrier 37. Also herein, the valve (c) opening port 9, which was opened once through sticking of the needle 53, will be closed up through the self-restoring force due to the elasticity of that rubber.

Figure 13:
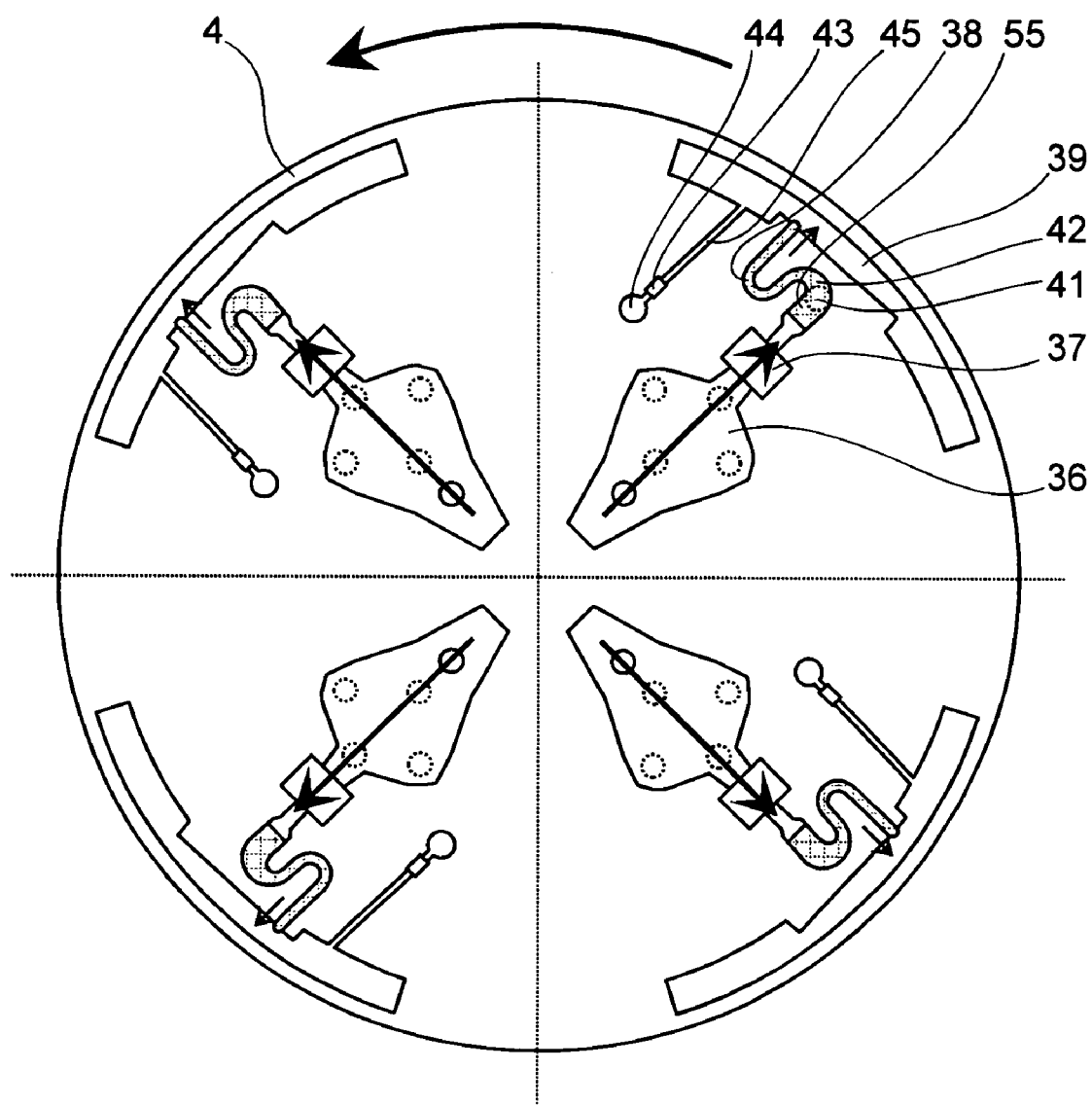
FIG. 13 is a plane view of the front side surface of the second disc, showing a step for transferring the liquid mixture and rinsing liquid into a water liquid reservoir.

Next, FIG. 13 is a view for showing the process for transferring the mixture liquid 55 indicted by hutching into the waste liquid reservoir 39 due to the principle of the centrifugal force and the siphon's law. This processing is as follows:

(1) The disc device 1 is rotated at a rotation speed, so as to generate the centrifugal force, such as about 10,000 G, for example, so that the mixture liquid 55 penetrates through the carrier 37, completely, and that no mixture liquid remains within the carrier 37. In this instance, the mixture liquid 55 remains within a portion, which is built up with the "U"-shaped flow passage 38 connected to the waste liquid reservoir 39, the collected eluting liquid reservoir 42, and the eluting liquid collecting valve 41, and filled up with therein;

(2) Penetrating through the "U"-shaped flow passage 38 by the centrifugal force of about 10,000 G mentioned above, the mixture liquid 55 is transferred into the waste liquid reservoir 39, gradually. In this instance, due to the movement of the mixture liquid 55, the air is compressed within the waste liquid reservoir 39, and this air is discharged into an outside of the disc device 1, through the air removal flow passage 45, the mist scattering prevention filter 43, through which the air can pass, and the outer connection bore 44. In this manner, the movement of the mixture liquid 55 can be achieved, smoothly; and (3) Since the mixture liquid 55 is filled up within the "U"-shaped flow passage 38 and the collected eluting liquid reservoir 42, under the condition containing no air-layer therein, all the mixture liquid 55 is transferred into the waste liquid reservoir 39 due to the siphon's law, without remaining liquid therein. In the manner as was mentioned in the above, the mixture liquid 55 is transferred into the waste liquid reservoir 39. However, the mixture liquid 55 has such an amount thereof, that it fills up within the spaces of the "U"-shaped flow passage 38 and the collected eluting liquid reservoir 42 mentioned above, under the condition of containing no air-layer therein, or alternatively the "U"-shaped flow passage 38 and the collected eluting liquid reservoir 42 are designed, so as to satisfy such the condition.

Next, though not shown in the figure, after transferring the mixture liquid 55 into the waste liquid reservoir 39, a step or process is carried out of rinsing or washing away components of the protein and the combining liquid, which adhere onto the carrier 37. This is completed, by breaking through the valve (d) 32 and the valve (e) 33 with using the needle 53, and by applying the centrifugal force to the rinsing liquids A and B, respectively, so as let the rinsing liquids A and B penetrate through the carrier 37, in the same manner as in the transfer of the combining liquid. In this instance, the protein component is removed away by means of the rinsing liquid A, while the combining liquid component by means of the rising liquid B. Further, all the rinsing liquid A and the rising liquid B are transferred into the waste liquid reservoir 39, due to the same principle or law to that, which is applied in the step or process for transferring the mixture liquid 55 into the waste liquid reservoir 39.

Figure 14:
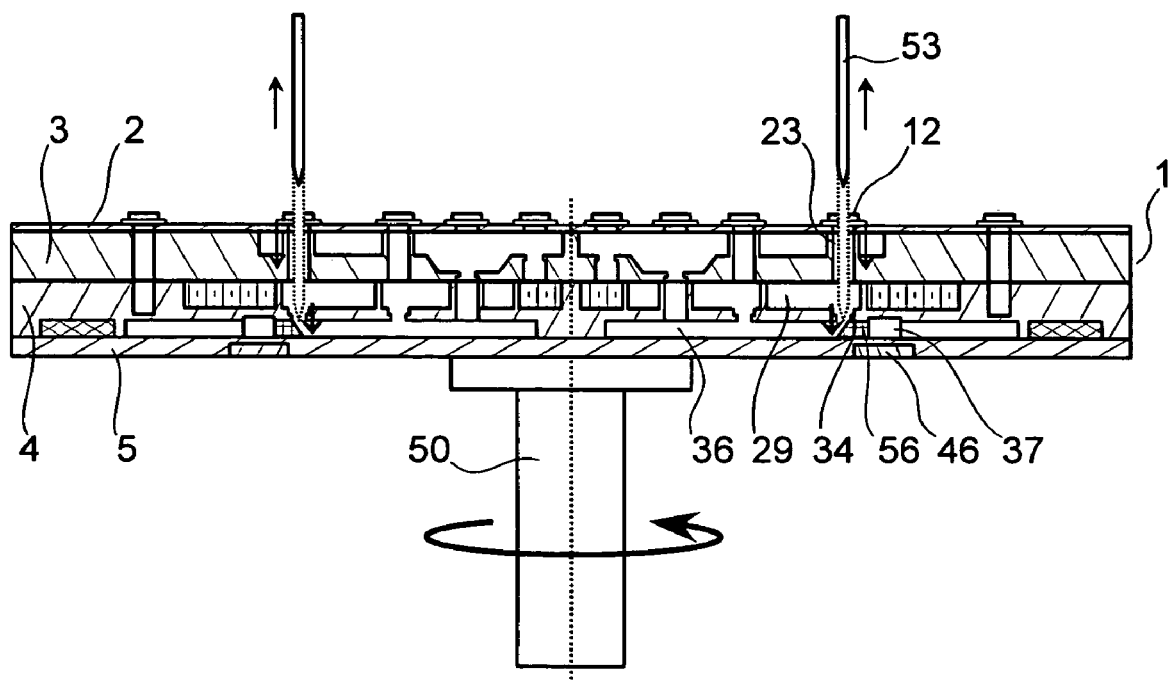
FIG. 14 is the a-a' cross-section view of the disc device shown in FIG. 1 mentioned above, showing a step for eluting nucleic acid into an eluting solution through transferring the liquid to the position of the eluting solution.

Next, FIG. 14 is a view for showing the processing for transferring the eluting solution 56 into the carrier 37 with using the needle 53, thereby eluting the RNA of virus combining with the carrier 37 into the eluting solution 56. This processing is as follows:

(1) The needle 53 is inserted into the disc device 1 through the valve (f) opening port 12;

(2) Passing through the valve (f) opening needle insertion bore 23, the needle 53 breaks through the valve (f) 34. And, thereafter, the needle 53 is pulled out;

(3) The eluting solution 56 held within the eluting solution reservoir 29 flows into the mixture flow passage 36. In this instance, the disc device 1 is rotated at a low rotation speed, so that the eluting solution 56 cannot penetrate through the carrier 37. With this, the eluting solution 59 contained within the eluting solution reservoir 29 passes through the valve (f) 34 due to the centrifugal force, and all of it flows down into the mixture flow passage 36. And, with this centrifugal force, the eluting solution 56 comes to be in contact with the carrier 37, as shown in the figure, and after the carrier 37 is immersed therein, the disc device 1 is stopped in the rotation thereof; and (4) Conducting electricity through the carrier heating resistors 46, the carrier 37 is heated up together with the eluting solution 56 held in an inside thereof, i.e., from 60° C. to 70° C. in temperature. By the process as mentioned above, the eluting solution 56 is transferred to the carrier 37, thereby eluting the RNA combining with the carrier 37 into the eluting solution 56. Further, in this instance, the valve (f) opening port 12, which was opened once through sticking of the needle 53, will be closed up through the self-restoring force due to the elasticity of that rubber.

Figure 15:
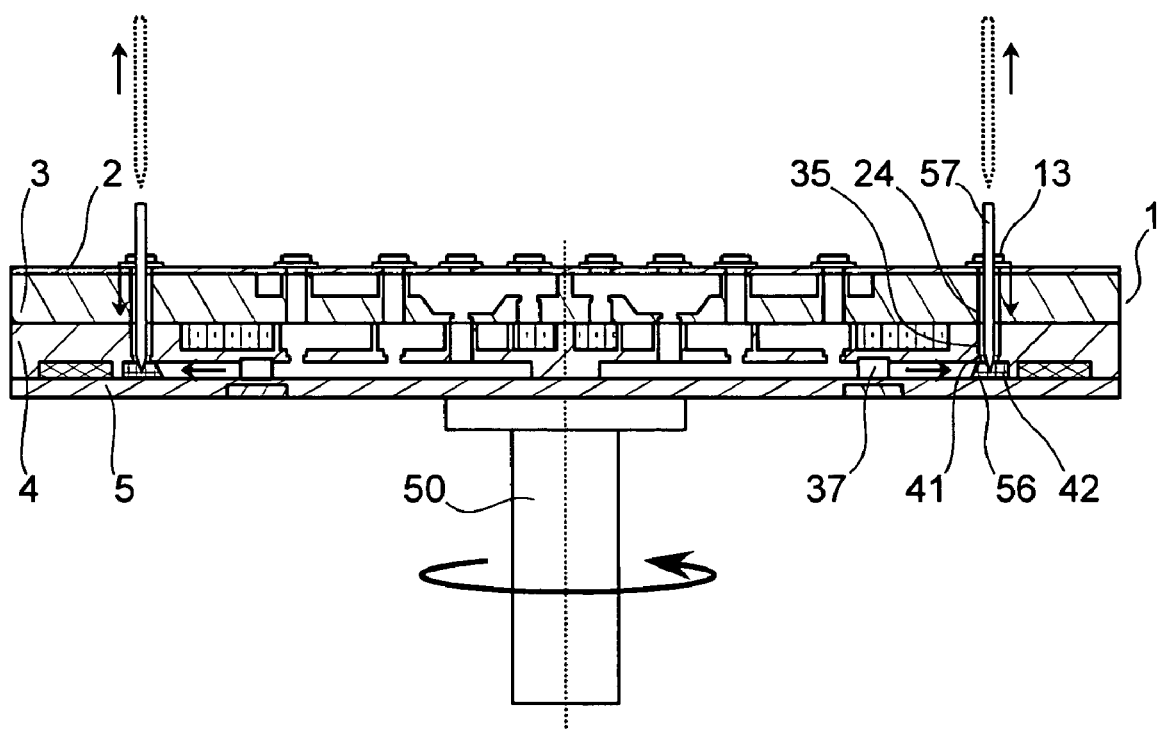
FIG. 15 is the a-a' cross-section view of the disc device shown in FIG. 1 mentioned above, showing a step for collecting the eluting solution having passed through the carrier.

Next, FIG. 15 is a view for showing the processing for holding/collecting the eluting solution 56, into which the RNA of virus is eluted, with using an eluting solution collection chip 57 attached with a needle tube. This processing is as follows:

(1) The eluting solution 56, into which is eluted the RNA held on the carrier 37 in the previous step or process, is moved into the collected eluting liquid reservoir 42 due to the centrifugal force, such as of around 3,000 G, for example, and it is held at that position;

(2) The eluting solution collection chip 57 is inserted into the disc device 1 through the eluting solution collection port 13;

(3) This eluting solution collection chip 57 passes through the eluting liquid collecting tip insertion portion 24 and the eluting liquid collecting tip insertion portion 35, and breaks through the eluting liquid collecting valve 41; and (4) The eluting solution collection chip 57 is held at the position of the collected eluting liquid reservoir 42, and the eluting solution 56 into which the RNA is eluted is absorbed into this eluting solution collection chip 57, thereby being collected therein.

By the process mentioned above, the collection of the eluting solution 56 is achieved, into which the RNA of virus is eluted. Also herein, the eluting solution collection port 13, which was opened once through sticking of the eluting solution collection chip 57, will be closed up through the self-restoring force due to the elasticity of that rubber. Also, the eluting solution 56 is determined in a liquid amount thereof, so that it is not enough for filling the "U"-shaped flow passage 38 shown in FIG. 5 mentioned above, but sufficient for filling the collected eluting liquid reservoir 42 partially. In other words, the "U"-shaped flow passage 38 and the collected eluting liquid reservoir 42 mentioned above are designed so that they are in such the condition as mentioned above. For this reason, the eluting solution 56 will not be transferred into the waste liquid reservoir 39 shown in FIG. 5, even if the centrifugal force, such as about 10,000 G mentioned above, is applied to the eluting solution 56, into which the RNA is eluted. Passing through each of the steps or processes mentioned above, from the blood, it is possible to refine the RNA of the virus contained therein.

Herein, in FIG. 16 attached are shown the refining processes of steps mentioned above, being collected together, in the form of a flow thereof. Namely, a step 1 is that for conducting the separation/quantification of serum. In this step, a blood is injected into from the blood insertion port 6, and the disc is rotated to separated the blood through the centrifugal force by rotating thereof, thereby holding the quantified serum 54 of the necessary amount in the gutter 17 (corresponding figures: FIGS. 8, 9, and 10).

A step 2 is a step for combining the nucleic acid. In this step, the quantified serum 54 within the gutter 17 mentioned above moves into the mixture flow passage 36, while the combining liquid for combining with the nucleic acid moves into the mixture flow passage 36, and then the quantified serum 54 and the combining liquid are mixed up therein. And, those mixture liquid 55 penetrates through the carrier 37, during the process of which the nucleic acid (i.e., the RNA) combine with the carrier 37. And the mixture liquid 55 flows into the waste liquid reservoir 39 (see, corresponding figures: FIGS. 11, 12, and 13).

A step 3 is a rinsing process for the carrier. In this step, the rinsing liquid A and the rinsing liquid B penetrate through the carrier 37, and move into the waste liquid reservoir 39.

And, a step 4 is a separation/collection process of the nucleic acid. In this process, the eluting solution 56 moves within the mixture flow passage 36, and this eluting solution 56 is held by means of the carrier 37. Then, the eluting solution 56 is heated through the heating of the carrier heating resistors 46. Thereafter, this eluting solution 56 moves into the collected eluting liquid reservoir 42, and is collected from the eluting solution collection port 13 (see, corresponding figures: FIGS. 14 and 15).

Next, explanation will be given on the structure of the disc device 1, according to other embodiment (i.e., the second embodiment) of the present invention, and a refining method with using thereof, hereinafter.

The structure of the disc device 1 according to the second embodiment differs from that of the first embodiment, only in the structure of the second-layer disc 4 thereof. In more details, though not shown in FIG. 17, it differs from that mentioned above, in the structure and the position a waste liquid reservoir 59 for accumulating waste liquid including the quantified serum 54 and the combining liquid, and the rinsing liquid A and the rinsing liquid B. Further, it also differs therefrom, in that a branch flow channel 58 branched is provided in the downstream flow path after the carrier 37 mentioned above.

Figure 17:
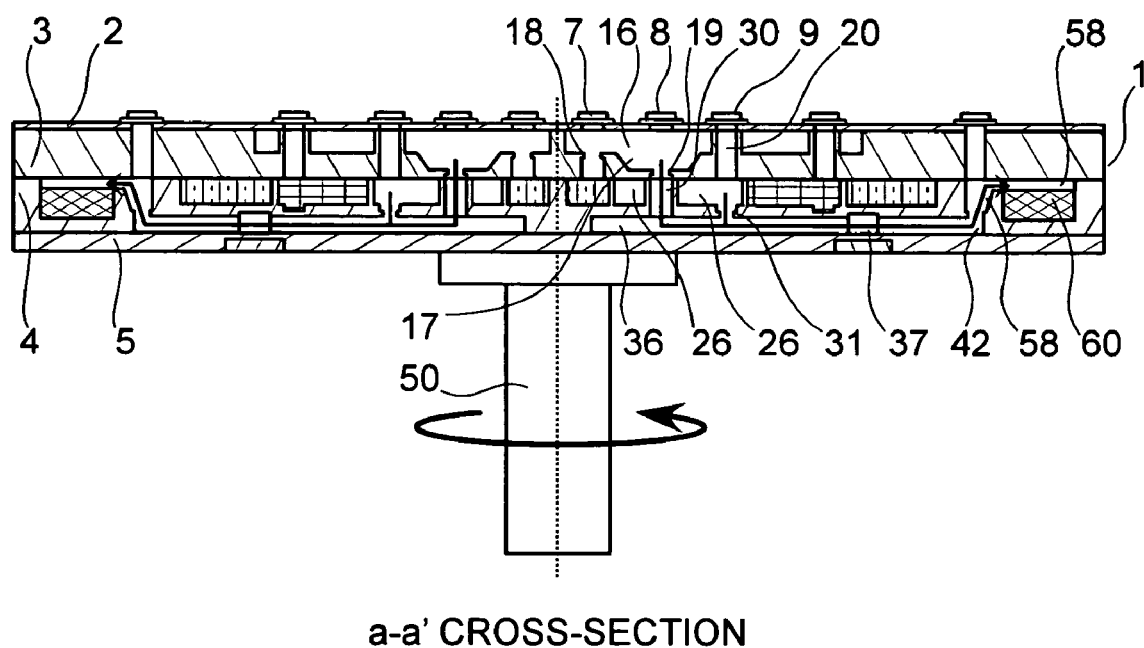
FIG. 17 is a cross-section view of a disc device, for explaining about the structure of the disc device and the method for refining the nucleic acids, of other (second; $2^{nd}$)

Next, explanation will be made on the process for refining the RNA from blood, by referring to FIGS. 17 and 18. In the same manner as in the first embodiment (i.e., the first method) mentioned above, the serum in excess is discharged with using the needle 53 (however, not shown in those FIGS. 17 and 18), and the mixture liquid 55 including the quantified serum 54 containing the virus therein and the combining liquid 55 (after mixing, into this mixture liquid 55 is eluted the RNA thereof, being dissolved from the virus), is brought to penetrate through within the carrier 37 by the centrifugal force of about 3,000 G. However, in this instance, the mixture liquid 55 penetrating through the carrier 37 is transferred up to the position of the collected eluting liquid reservoir 42, due to this centrifugal force, once.

Further, due to the centrifugal force of about 10,000 G, the mixture liquid 55 comes up through the branch flow channel 58 and it reaches to the waste liquid reservoir 59 formed on the surface side of the second-layer disc 4. However, in this instance, since the branch flow channel 58 is formed in such the shape as shown in the figure, the liquid will not turns back to the collected eluting liquid reservoir 42 (see FIG. 17), if the disc device 1 is stopped in the rotation thereof. Furthermore, regarding the rinsing liquid A and the rinsing liquid B, they are also made to penetrate through the carrier 37, and thereby are transferred into the waste liquid reservoir 59, in the same principle. Next, in the same manner to the method of the first embodiment mentioned above (i.e., the first method), the valve (f) 34 is opened by the needle 53, thereby letting the carrier 37 to hold the eluting solution 56 therein, and further thereafter, the eluting solution 56 and the carrier 37 are heated by means of the carrier heating resistors 46. Then, the eluting solution 56 comes up from 60° C. to 70° C. in the temperature thereof, and thereby allowing the carrier 37 to elute the RNA of virus combining thereon into the eluting solution 56.

Thereafter, the eluting solution 56 penetrates through within the carrier 37 due to the centrifugal force, and is transferred into the collected eluting liquid reservoir 42. In this instance, to the eluting solution 56 is applied the centrifugal force, so that the said eluting solution 56 will not move up through the branch flow channel 58 to the waste liquid reservoir 59, however the eluting solution 56 can penetrate through the carrier 37 (such as, the centrifugal force of about 3,000 G, for example). Finally, in the same manner to that of the first embodiment mentioned above (i.e., the first method), the eluting solution collection chip 57 is inserted through the eluting solution collection port 13 and the eluting liquid collecting tip insertion portion 24, thereby collecting the eluting solution 56, into which the RNA is eluted. With such the structure and the steps as mentioned above, it is possible to refine the target RNA.

Next, explanation will be given on the structure of the disc device, according to further other embodiment (i.e., the third embodiment) of the present invention, and a refining method with using thereof.

FIG. 19 shows the structure on the surface side of the second-layer disc 4 building up the disc deice 1. The structures of other parts than that are same with those in the first embodiment mentioned above, therefore the explanations thereof will be omitted herein.

Further, with the disc device 1 according to the further other embodiment (i.e., the third embodiment), it differs from the first embodiment mentioned above, in the structure that, within the flow passage connecting from the carrier 37 to the waste liquid reservoir 39 is provided a filter 61, which has the density being further higher than that of the carrier mentioned above, and that the collected eluting liquid reservoir r 42 is formed in a drum-like shape so that it can easily hold the eluting solution 56 therein (not shown in FIG. 19). With the second-layer disc 4 having such the form as mentioned above, after making the mixture liquid 55 containing the quantified serum 54 including the virus therein and the combining liquid (after mixing thereof, into the mixture liquid is eluted the RNA of virus through dissolving of the virus) penetrate through within the carrier 37, the mixture liquid 55 is further brought to penetrate through the filter 61 mentioned above due to the centrifugal force, such as of about 20,000 G, for example, thereby being transferred into the waste liquid reservoir 39. Thereafter, bringing also the rinsing liquid A and the rinsing liquid B to penetrate through the carrier 37, sequentially, on the same principle mentioned above, thereby they are transferred into the waste liquid reservoir 39. Finally, applying the centrifugal force of such the degree, that it can penetrate through the carrier 37 but cannot pass through the filter 61 (such as, the centrifugal force of about 3,000 G, for example), the eluting solution 56, into which the RNA of virus is eluted, is accumulated within the collected eluting liquid reservoir 42. And, the eluting solution 56 is collected in the same manner as in the first method mentioned above.

Namely, with such the structures and the steps mentioned above, it is possible to refine the RNA in the disc device 1 according to the third embodiment.

Finally, explanation will be made on the method for refining the nucleic acid as the target, i.e., the RNA of virus, from the blood as the sample, with using a nucleic acid refining apparatus being made up with the disc device 1, according to the present invention, the structures and the operations of which was explained above in the details thereof.

First, FIG. 20 is a diagrammatical view for showing a brief concept of the nucleic acid refining apparatus with using the disc device 1. This apparatus comprises: a motor 62 connected to the disc device 1; an arm 63 attached with an electricity conduction terminal for conducting electricity to the disc device 1; a punching machine 64 for opening the valve(s) within an inside of the disc device 1; a robot arm 65 attached with a chip for collecting the eluting solution, into which the RNA is eluted; a pump 66 for sucking out the eluting solution; piping 67; an eluting solution collection bottle 68 to be injected with the collected eluting solution; a robot arm 69 attached with a chip for blood for injecting the blood into the disc device 1; a blood bottle 70 for holding the blood to be tested therein; and a housing 71. However, for the apparatus shown herein, it is not always necessary to be structured in the above manner, nor to be structured with all the constituent elements thereof, and in the place thereof, for the person skilled in the art, various kinds of variations can be considered in many ways.

However, the steps of the method for refining the RNA are as follows, with using the apparatus, an example of the structure of which is shown in FIG. 20.

(1) The sample blood is taken out by a certain amount thereof, through the pump 66, from the blood bottle 70 for holding the blood including the virus as the target therein, by means of the robot arm 69 attached with the chip for blood, and it is injected into the inside of the disc device 1 through the blood insertion portion 6;

(2) Passing through the steps of the disc device 1 explained above, sequentially (i.e., blood-cell separation; mixture of the serum and the combining liquid; penetration of the mixture liquid through the carrier; penetration of the rinsing liquids through the carrier; elution of the RNA combining with the carrier; and holding the eluting solution, separating it from the mixture liquid and the rinsing liquids), the eluting solution 56 can be obtained, into which the RNA of virus is eluted.

However, herein, the valve (a) 18, the valve (b) 19, the valve (c) 31, the valve (d) 32, the valve (e) 33, and the valve (f) 34 are opened by means of the punching machine 64 mentioned above. Also, this disc device 1 is rotated by means of the motor 62. When conducting the electricity through the carrier heating resistors 46, the disc device 1 is stopped in the rotation thereof, and the arms 63 attached with the electricity conduction terminal are contacted with a plus (+) electrode 48 and a minus (−) electrode 49 of the disc device 1;

(3) The eluting liquid collecting valve 41 within the inside of the disc device 1 is opened by means of the robot arm 65 attached with the chip for collecting the eluting solution, thereby collecting the eluting solution 56, into which the RNA is eluted, by means of the pump 66. Further, that eluting solution 56 is moved into the eluting solution collection bottle 68, thereby obtaining the eluting solution 56 desired.

In the manner mentioned above, it is possible to refine only the eluting solution containing the RNA therein, from the blood including the RNA as the target, separating it from co-existing materials included within the blood.

The blood (i.e., the whole blood) was explained as the sample containing the nucleic acid therein, in the explanations given in the above. However as the sample containing such the nucleic acid therein, others may be included than the blood (i.e., the whole blood), for example, vital samples, such as, the blood serum and urine, etc., and also biological samples, such as, cultivated cells and/or bacteria, etc., and the present invention can be applied thereto. Also, as the target nucleic acid, the explanation was given on the HCV virus or the HIV virus as the one example thereof, however according to the present invention, it should not be restricted only to those, but it may be applied to others, such as, deoxyribonucleic acid (DNA), for example. Further, with the silica-made carrier made for catching the nucleic acid mentioned above may be made up by using silica particle, quartz wool, quartz filter paper, or fragmentation thereof, for example. Also, as the combining liquid containing the chaotropic ion therein, the solution of guanidine thiocyanate is preferable, however other than this, it may be the solution of guanidine-hydrochloric acid, the solution of sodium iodide, or the solution of potassium iodide, etc. Further, as the rising liquid A is preferable a solution mainly containing guanidine thiocyanate therein, for example, or as the rising liquid B is preferable a water solution containing 50% of ethanol therein. And, as the eluting solution, TE buffer solution (pH 8.0) is preferable.

Also, according to the present invention, it is possible to increase contact frequency between the nucleic acid within the sample and the solid phase, even in the case when concentration of the nucleic acid contained within the sample is low, such as of $10^2$ copy/ml about, and with this, it is possible to refine the nucleic acid at high collection rate. Also, since the steps mentioned above are processed within the inside of the same device, according to the present invention, the problem of contamination can be dissolved.

Further, according to the embodiment of the present invention, it is possible to make the refining operation of the nucleic acid automate, easily. Furthermore, according to the present invention, since the centrifugal force can be applied to the refining processes of the nucleic acid, it is possible to increase the density of the solid phase provided within the carrier, therefore the nucleic acid can be refined at high collection rate, even in the case of low concentration of the nucleic acid contained within the sample.

Next, explanation will be given on other embodiment of the nucleic acid refining apparatus, according to the present invention, by referring to FIGS. 21 to 38.

FIG. 21 shows the total structure of a gene analyzer with using the nucleic acid refining apparatus according to the present invention. This gene analyzer 901 comprises: a holder disc 912 being supported rotatably by a motor 911; plural analysis discs 902 of a sector form, each being positioned on the holder disc 912 by means of projections 121; a punching machine 913 for controlling the flow of liquids; and two (2) sets of optical apparatuses, i.e., an upper portion optical apparatus 914 and a lower portion optical apparatus 915. Further, the holder disc 912 comprises a holder disc optical window 122 for the lower portion optical apparatus 915.

FIG. 22 is a view for showing the refining structure of nucleic acid, i.e., the structure of an analysis disc 902. This analysis disc 902 is basically constructed by connecting between an upper cover 920 and a channel portion 930. The upper cover 920 comprises: a sample injection opening 210; a plural number of reagent injection openings 220, 230, 240, 250, 260 and 270; a plural number of air holes 212, 222, 272, 273; and a plural number of cover-attached air holes 221, 231, 241, 251, 261 and 271. The channel portion 930 comprises a positioning hole 710, and a container, which will be mentioned later, and channels, etc. Also, the analysis disc 902 is positioned by inserting the projection 121 of the holder disc 912 into the positioning hole 710.

The structure of the channel portion 930 mentioned above will be shown in FIG. 23 attached. The embodiment of the channel portion shown in this FIG. 23 comprises a channel, so as to add a detection reagent for analysis thereto, after separation of the serum from the whole blood, and after extraction of nucleic acids, which are contained in the virus within the serum.

Hereinafter, explanation will be made on an analysis operation of the viral nucleic acid in the case of using the whole blood as the sample. However, flows of the extraction and the analysis operation will be shown, by referring to FIGS. 24 and 25, and the flow conditions within the channel portion 930 will be shown, by referring to FIGS. 26 to 38.

An operator of this apparatus, first of all, injects the reagents into the respective reagent containers 320, 330, 340, 350, 360 and 370, from the upper cover 920 of the analysis disc 902 through the injection openings 220, 230, 240, 250, 260 and 270, separately, and thereafter keeps them covered. The operator mounts the analysis discs 902 onto the holding disc 912 in a necessary number thereof, after injecting the reagents therein, depending upon that necessary number of analysis.

Next, the whole blood, being collected by means of a vacuum blood collection tube, etc., is injected into the sample container 310 from the sample injection opening 210 (see FIG. 26).

After injection of the whole blood 501, the holder disc 912 is rotated by means of the motor 911. The whole blood injected into the sample container 310 flows into an outer peripheral side thereof due to the function of the centrifugal force, which is generated accompanying with the rotation of the holder disc 912, thereby filling up within insides of a blood cell storage container 311 and a serum quantification container 312, on the other hand the whole blood in excess flows into a whole blood disposal container 315 from an overflow fine tube channel 313 through an overflow thick tube channel 314 (see FIG. 27). This whole blood disposal container 315 has an air channel 318 for use of disposal of whole blood, and further there is an air hole 212 for use of disposal of whole blood at the position corresponding to the most-interior portion of the whole blood disposal air channel 318 on the upper cover 920. For this reason, the air can freely go in and out therethrough. The connection portion is expanded abruptly, covering from the overflow fine tube channel 313 to the overflow thick tube channel 314, and it lies within the most-interior side of the overflow fine tube channel 313 (at the radius position 601), therefore the whole blood is cut out at the connection portion under the condition where it fills up within the overflow fine tube channel 313. Accordingly, in an inner side from the radius portion 601 in the figure, the liquid cannot lie therein, for this reason, also a liquid surface in the serum quantification container 312 comes up to this radius position 601. Further, the whole blood flows also into a serum capillary tube 316, which is divided from the serum quantification container 312, and also herein the most inner potion of the whole blood lies at the radius position 601.

Further when the holder disc continues the rotation thereof, the whole blood 501 is separated into the blood cells and the serum (i.e., the centrifugal separation), and thereby the blood cell 502 moves into the blood cell storage container 311 at the outer peripheral side, while the serum quantification container 312 being filled up with only the serum 503 therein (see FIG. 28).

However, in the series of operations for separating the serum mentioned above, the air holes 221, 231, 241, 251, 261 and 271 of the respective reagent containers are under the condition that they are closed up with the covers thereof, so that the air cannot come in therefrom.

On the other hand, though each of the reagents tries to flow out from the outer-peripheral side thereof due to the centrifugal force applied, however it cannot flow outside, because within the reagent container, into which no air can enter therein, the pressure being lowered maintains the balance with the centrifugal force. However, in accordance with rise-up in the centrifugal force with an increase of the rotation speed, the pressure within this reagent container is lowered gradually, and when it comes to be equal or less than the saturation vapor pressure of the reagent, bubbles are generated in an inside thereof. Then, forming such a channel structure for turning the reagent flowing out from the outer peripheral side of each the reagent container into the inside thereof, once, as shown in FIG. 26 attached (i.e., return channels 322, 332, 342, 352, 362 and 372), enables to suppress the lowering of the pressure within the reagent container, and thereby to prohibit the bubbles from generating in the inside thereof. In this manner, each the reagent will not flow, while being held within the reagent container, during the time-period of the separation operation of serum.

When completing the separation operation of serum through rotating thereof for a predetermined time, the analysis disc 902 is stopped, and a part of the serum 503 within the serum quantification container 312 moves into an inside of the serum capillary tube 316 due to the surface tension (i.e., the capillary movement). Thus, it enters up to a mixing portion inlet, i.e., the connecting portion between a mixing portion 410 and the serum capillary tube 316, thereby filling up the inside of the serum capillary tube 316 therewith.

Hereinafter, the punching machine 913 opens a hole one by one, on the cover of the air holes, being provided on an upper portion of each of the reagent containers, and thereafter the motor 11 is rotated, thereby letting the each agent to flow due to the centrifugal force. As is shown on the cross-section view of the analysis disc, the reagent injection openings (i.e., 240, 250, and 260) and the air holes (i.e., 241, 251, and 261) are provided on the upper cover 920, corresponding to the upper portion of each of the reagent containers, and those air holes are closed up with the cover. Then, the punching machine 913 opens the holes on this cover, thereby bringing it under the condition that the air can come into the inside of the said reagent container.

Hereinafter, operations will be shown, after the completion of the separation of serum.

Into the eluting solution container 320 is injected an eluting solution 521 for lysing protein of the virus within the serum therein, separately. Namely, when the motor 911 is rotated after the punching machine 913 opens the hole on the cover of the lysis solution air hole 221, the lysis solution 521 flows from the lysis solution container 320 through the return channel 322 into the mixing portion 410 due to the function of the centrifugal force. Also, since the most-inner side of the serum within the serum quantification container 312 (i.e., it lies on the radius position 601 when completing the separation of serum) lies within an inner periphery side than an inlet 411 of the mixing portion (on the radius position 602), because of the head difference due to the centrifugal force, the serum within the serum quantification container 312 and the serum capillary tube 316 flows from the mixing portion inlet 411 into the mixing portion 410 (see FIG. 29). Further, this mixing portion 410 is made up with a material, within which the serum and the lysis solution can be mixed up, such as a porous filter or fiber of resin, glass or paper, etc., or projections of silicon or metal, etc., which is manufactured through etching or mechanical machining, for example.

Then, the serum and the lysis solution, being mixed within the mixing portion 410 mentioned above, flows into a reactor container 420 (see FIG. 30). In this reactor container 420, there is provided an airflow passage 423 for the reactor container, and further is provided an airflow passage 222 for the reactor container at the position corresponding to the most-inner peripheral portion of the reactor container airflow passage 423 on the upper cover 920, therefore the air can comes in and out, freely within the inside and the outside thereof. And, the branch portion 317 from the serum quantification container 312 to the serum capillary tube 316 (at the radius portion 603) lies within the inner periphery side than the mixing portion inlet 411 (at the radius position 602) mentioned above, therefore due to the effect of so-called the siphon, all the serum within the serum capillary tube 316 flows out into the mixing portion 410. On the other hand, since the serum within the serum quantification container 312 flows into the serum capillary tube 316 due to the centrifugal force, the serum continues to flow out into the mixing portion 410 until when the liquid surface of the serum reaches to the branch portion 317 (at the radius position 603). And, at a time point when the liquid surface of the serum reaches to the branch portion 317, the air is mixed into the serum capillary tube 316, so as to bring the inside thereof empty, thereby the serum stops flowing thereof. Namely, all the serum lying from the radius portion 601 to the radius position 603 at the time of completion of separation thereof, i.e., the serum within the serum quantification container 312, the overflow fine tube channel 313, and the serum capillary tube channel 316, flows into the mixing portion 410, thereby being mixed up with the lysis solution.

In the reactor container 420 react the mixed serum and the lysis solution with each other. Since the liquid surface lies within an outer periphery side than the most-inner periphery portion (i.e., the radius position 604) of a flow passage 421 of reacting liquid in the reactor container 420 after the mixture of the serum and the lysis solution flows to move into the reactor container 420, the mixture cannot cross over the most-inner periphery portion of the reacting liquid flow passage, therefore the mixture is held within the reactor container 420 during the rotation thereof.

The lysis solution functions to dissolve the membrane of the virus and/or the bacteria within the serum, thereby elute the nucleic acid therefrom, and it accelerate absorption of the nucleic acid on a nucleic acid combining material 301. As such the reagent as was mentioned may be used guanidine-hydrochloric acid, in particular for elution and absorption of the DNA, on the other hand guanidine thiocyanate for the RNA, and as such the combining material of the nucleic acid may be used a porous material, such as quartz or glass, etc., or a fiber filter or the like, for example.

Next, after the serum and the lysis solution are held within the reactor container 420, the motor 911 is stopped, holes are opened on the cover of the addition liquid air hole 231 by means of the punching machine 913, for supplying the air into the addition liquid container 330, and then the motor 911 is rotated again. Then, due to the function of the centrifugal force, an addition liquid 531 flows from the addition liquid container 330 through the addition liquid return passage 332 into the reactor container 420, thereby bringing the liquid surface of the mixture liquid within the reactor container 420 into the inner periphery side thereof (see FIG. 31). Thereafter, when this liquid surface reaches up to the most-inner periphery portion of the reacting liquid passage 421 (i.e., the radius position 604), the mixture liquid flows out, exceeding the most-inner periphery portion of the reacting liquid flow passage, through a combined flow passage 422, into the nucleic acid combining material 310. As such the addition liquid as was mentioned may be used the lysis solution mentioned above, for example.

Further, depending upon the sample, it sometimes happens that the mixture liquid flows to move within the reacting liquid flow passage 421 due to the phenomenon of capillary tube, even if the mixture liquid is superior in wetability on a wall surface and/or under the condition of stopping thereof, and in such the instance, the addition liquid is not needed.

When the lysis solution and the serum pass or penetrate through the nucleic acid combining material 301 in this manner, the nucleic acid is absorbed onto the nucleic acid combining material 301, while the liquid (i.e., the mixture liquid) flows into a detector container 450. This mixture liquid is sufficiently larger than the volume of the detector container 450, into which it flows into, in a liquid amount thereof, and therefore it flows out, exceeding the most-inner periphery portion of a waste liquid flow passage 452 (i.e., the radius position 607) into a waste liquid container 460 (see FIG. 32).

On the other hand, the mixture liquid within the reactor container 420 flows out gradually, from the combined flow passage 422 through reacting liquid flow passage 421. However, since the branch portion (i.e., at the radius position 605) from the reactor container 420 to the reacting liquid flow passage 421 is located within an inner periphery side than the combined flow passage 422 (i.e., at the radius position 606), all the mixture liquid within the reactor container 420 flows into the combined flow passage 422 due to the siphon phenomenon (see FIG. 33). The liquid flowing into the detector container 450, passing through the nucleic acid combining material 310, is also in the same manner as was mentioned, i.e., all the liquid within the detector container 450 flows out into the waste liquid container 460 through the waste liquid flow passage 452, due to the siphon phenomenon, too, since the branch portion from the detector container 450 to the waste liquid flow passage 452 (i.e., at the radius position 608) is located within the inner periphery side than an exit to the waste liquid flow passage 452 into the waste liquid container 460.

Next, the motor 911 is stopped, and holes are opened by means of the punching machine 913, on the cover of the first washing liquid air hole 241, for supplying the air into the first washing liquid container 340. Thereafter, when the motor 911 is rotated again, due to the function of the centrifugal force, the first washing liquid 541 flows from the first washing liquid container 340 through the first washing liquid return flow passage 342 into the nucleic acid combining material 301, thereby flowing out unnecessary components, such as the protein, etc., attaching onto the nucleic acid combining material 301, for example (see FIG. 34). Further, as the first washing liquid may be used, for example, the lysis solution mentioned above, or a liquid being lowered in the concentration of salt of the said lysis solution. Also, a liquid amount of the first washing liquid 541 is sufficient larger than the volume of the detector container 450, and therefore it flows out into the waste liquid container 460, exceeding the most-inner periphery portion of the water liquid flow passage 452 (i.e., at the radius position 607), (see FIG. 34).

Furthermore, all the liquid within the detector container 450 flows out into the waste liquid container 460 through the waste liquid flow passage 452, due to the siphon phenomenon too, (see FIG. 35).

Hereinafter, the same washing operations are repeated in a plural number thereof. For example, following those for the first washing liquid, a hole is opened on the cover of the second rinsing liquid air hole 241 by means of the punching machine 913 for supplying the air into the second washing liquid container 350, and thereafter the motor 911 is rotated, again. With this, the unnecessary components, such as salt, etc, attaching onto the nucleic acid boding material 301, is flowed out (see FIG. 36). Further, such the washing liquid as was mentioned may be used ethanol, or a water solution of ethanol, for example. Also, this washing may be repeated further, in the same manner, depending upon the necessity thereof.

As was mentioned in the above, after following of washing out the nucleic acid combining material 301, thereby bringing it under the condition of absorbing only the nucleic acid in the nucleic acid combining material 301, the process is shifted into an eluting process of the nucleic acid.

Namely, in this eluting process of the nucleic acid, under the condition that the motor is stopped, a hole is opened by means of the punching machine 913, on the cover of the eluting solution air hole 261 for supplying the air into the eluting solution container 360, and further a hole is opened on the cover of the air hole for use of wasting the eluting solution, for communicating an eluting solution waste container 470 with an outside thereof. And, the motor 911 is rotated, again, thereby flowing the eluting solution into the nucleic acid combining material 301 (see FIG. 36). This eluting solution is a liquid used for eluting the nucleic acid from the nucleic acid combining material 301, and it may a water or a water solution, which is adjusted from 7 to 9 in pH, for example. In particular, for the purpose of bringing the nucleic acid to elute easily therein, it is preferable to be heated it up to be equal or higher than 40° C. For this heating, a light may be irradiated upon from the above of the eluting solution container 360, with using the upper optical apparatus 914 shown in FIG. 21 mentioned above.

After passing or penetrating through the nucleic acid combining material 301, the eluting solution 561 flows into the detector container 450 (see FIG. 37). A liquid amount of this eluting solution is smaller than the volume of the detector container 450, and therefore the liquid within the detector container 450 (i.e., at the radius position 610 of the liquid surface) cannot cross over the most-inner periphery portion of the waste liquid flow passage 452 (i.e., at the radius position 607), thereby being held within the detector container 450.

Next, under the condition that the motor is stopped, a hole is opened by means of the punching machine 913, on the cover of the detection liquid air hole 271 for supplying the air into the detection liquid reservoir container 370, and thereafter the motor 911 is rotated, again, thereby letting the detection liquid 571 to flow into the detector container 450 (see FIG. 38). This detection liquid may be a reagent for amplifying the nucleic acid to be detected, such as deoxy nucleoside triphosphate or DNA synthetic enzyme, for example, and it may include fluorescence reagent therein. Further, depending upon the amplifying method, it may be possible to heat it up, with using the upper portion optical apparatus 914 shown in FIG. 21 mentioned above, thereby irradiating the light thereupon from the above of the detector container 450.

Continuously, also moving the lower portion optical apparatus 915 also shown in FIG. 21 mentioned above below the detector container 450, thereby an amount of emission of fluorescence is detected, for example.

By the way, at the time of punching, the heating, and the detecting, it is necessary to stop the holder disc 912 at the predetermined position. Then, according to the present embodiment, as shown in FIG. 39, a projection 917 is provided on the holder disc 912 for positioning thereof, and it is detected by means of a position detector 916, thereby detecting the rotation position of the holder disc. Also, the controller 918 controls the rotation of the motor 911, the rotation and the vertical movement of the punching machine 913, and the rotation, the irradiation and the detection of the upper portion optical apparatus 914 and the lower portion optical apparatus 915.

Figure 40:
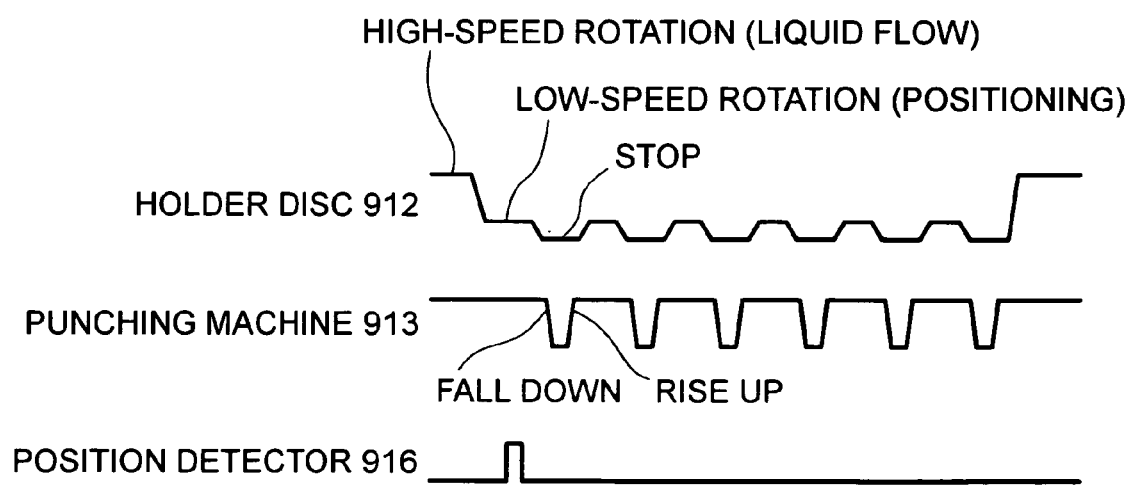

FIG. 40 shows the operation timing of the punching machine 913, for example. Namely, after completion of flowing of the whole blood and the respective reagents, the holder disc 912 is lowered in the rotation speed, and is maintained at a low rotation for positioning. When the position detector 916 detects the positioning projection 917, the holder disc 912 is stopped, and then the punching machine 913, after coming down to open the holes on the covers of the air holes for the respective reagent reservoir containers, goes up again. After this punching, the holder disc 912 is rotated at a low speed, so that no reagent flows out from the reagent reservoir containers after the punching, and it is stopped at the position of the next analysis disc, i.e., after rotating by sixty (60) degree when the analysis discs are mounted in six (6) pieces, and it repeats the same punching operation as was mentioned above. Further, the mounting positions of the analysis discs may be searched through a reflection light, which can be obtained by irradiation of the light from an optical window of the holder disc onto the channel portions 930 by means of the lower portion optical apparatus 915, for example. And, after completion of punching of all the analysis discs, the holder disc is rotated at a high speed, thereby bringing the reagents to flow to move.

As was mentioned in the above, according to the present invention, there is no necessity of provision of such the valves on the way of the flow passages, for controlling the flow of the respective reagents, as in the conventional art, nor no liquid remains within the valve portion on the way of the flow passages, therefore it is possible prevent from the contamination by the reagent in the pre-processing, thereby enabling extraction of a specific component, such as the nucleic acid or the like within the liquid sample, for example, at a high purity, so as to analyze the specific component, such as the nucleic acid or the like at high accuracy.

Further, as was mentioned previously, it is preferable to apply the present invention, in particular, into the analysis apparatus for refining the nucleic acid and/or for analyzing the extracted nucleic acid, i.e., the genes, and/or the analysis method therefore, however it may be applied into the apparatus and the method for refining chemical materials other than that. Namely, in more details, according to the present invention, it is possible to construct the analysis apparatus and the method thereof for analyzing the chemical materials, such as proteins and/or amino acids, etc., for example.

INDUSTRIAL APPLICABILITY

The present invention can be applied into the apparatus for refining the nucleic acid from a sample containing the nucleic acid therein. In particular, it can be also applied into, such as an automatic refining apparatus and the refining method thereof, being suitable for separating the nucleic acid from the materials coexisting with the nucleic acid, by utilizing the centrifugal force, and further can be applied into the refining apparatus of the chemical materials, etc. Also, it can be applied into a gene analysis apparatus comprising such the apparatus therein.

The invention claimed is:

1. A nucleic acid refining structure, being formed to be rotatable, comprising:
   a supply portion, through which is supplied a liquid including nucleic acid therein;
   a nucleic acid capture portion, onto which is captured the nucleic acid within said supplied liquid;
   a washing liquid supply portion, through which a washing liquid is supplied to said nucleic acid capture portion;
   a waste portion, into which is wasted said washing liquid flowing through said nucleic acid capture portion;
   an eluting solution supply portion, through which an eluting solution is supplied into said nucleic acid capture portion;
   an eluting solution holder portion for holding the eluting solution including the nucleic acid therein, being captured on said nucleic acid capture portion once and separated therefrom, after flowing through said nucleic acid capture portion, wherein
   said eluting solution hold portion is formed within a flow passage communicating between said nucleic acid capture portion and said waste portion;
   a cover for covering said supply portion, said nucleic acid capture portion, said washing liquid supply portion, said waste portion, said eluting solution supply portion and said eluting solution holder portion, said cover having a plurality of air holes sealed by a sealing material; and
   a punching machine for selectively punching a hole in the sealing material in at least one of the holes to control flow of at least the eluting solution.

2. A nucleic acid refining structure, being formed to be rotatable, comprising:
   a supply portion, through which is supplied a liquid including nucleic acid therein;
   a nucleic acid capture portion, onto which is captured the nucleic acid within said supplied liquid;
   a washing liquid supply portion, through which a washing liquid is supplied to said nucleic acid capture portion;
   a waste portion, into which is wasted said washing liquid flowing through said nucleic acid capture portion;
   an eluting solution supply portion, through which an eluting solution is supplied into said nucleic acid capture portion;
   an eluting solution holder portion for holding the eluting solution including the nucleic acid therein, being captured on said nucleic acid capture portion once and separated therefrom, after flowing through said nucleic acid capture portion, wherein
   said eluting solution holder portion is formed downstream of said nucleic acid capture portion, while said waste portion is formed downstream of said eluting solution holder portion;
   a cover for covering said supply portion, said nucleic acid capture portion, said washing liquid supply portion, said waste portion, said eluting solution supply portion and said eluting solution holder portion, said cover having a plurality of air holes sealed by a sealing material; and
   a punching machine for selectively punching a hole in the sealing material in at least one of the holes to control flow of at least the eluting solution.

3. A nucleic acid refining structure, being formed to be rotatable, comprising:
   a supply portion, through which is supplied a liquid including nucleic acid therein;
   a nucleic acid capture portion, onto which is captured the nucleic acid within said supplied liquid;
   a washing liquid supply portion, through which a washing liquid is supplied to said nucleic acid capture portion;
   a waste portion, into which is wasted said washing liquid flowing through said nucleic acid capture portion;
   an eluting solution supply portion, through which an eluting solution is supplied into said nucleic acid capture portion; and
   an eluting solution holder portion for holding the eluting solution including the nucleic acid therein, being captured on said nucleic acid capture portion once and separated therefrom, after flowing through said nucleic acid capture portion, wherein
   said eluting solution holder portion is formed on an outer periphery side of said nucleic acid capture portion, while said waste portion is formed on an outer periphery side of said eluting solution holder portion;
   a cover for covering said supply portion, said nucleic acid capture portion, said washing liquid supply portion, said waste portion, said eluting solution supply portion and said eluting solution holder portion, said cover having a plurality of air holes sealed by a sealing material; and
   a punching machine for selectively punching a hole in the sealing material in at least one of the holes to control flow of at least the eluting solution.

4. A nucleic acid refining structure, being formed to be rotatable, comprising:
   a supply portion, through which is supplied a liquid including nucleic acid therein;
   a nucleic acid capture portion, onto which is captured the nucleic acid within said supplied liquid;
   a washing liquid supply portion, through which a washing liquid is supplied to said nucleic acid capture portion;
   a waste portion, into which is wasted said washing liquid flowing through said nucleic acid capture portion;
   an eluting solution supply portion, through which an eluting solution is supplied into said nucleic acid capture portion;
   an eluting solution holder portion for holding the eluting solution including the nucleic acid therein, being captured on said nucleic acid capture portion once and separated therefrom, after flowing through said nucleic acid capture portion;
   a waste liquid flow passage communicating between said eluting solution holder portion and said waste portion, wherein said waste liquid flow passage comprises:
     a communication portion communicated with said eluting solution holder portion at an outer periphery side of said eluting solution holder portion,
     an inner periphery side area portion located downstream of said communication portion and on an inner periphery side of said communication portion and between an inner periphery side and an outer periphery side of said eluting solution holder portion, and a waste portion communication portion located downstream of said inner periphery side area portion, said waste portion communication portion communicating with said waste portion, and being located on an outer periphery side of said inner periphery side area portion;

a cover for covering said supply portion, said nucleic acid capture portion, said washing liquid supply portion, said waste portion, said eluting solution supply portion said eluting solution holder portion and said waste liquid flow passage, said cover having a plurality of air holes sealed by a sealing material; and a punching machine for selectively punching a hole in the sealing material in at least one of the holes to control flow of at least the eluting solution.

5. A nucleic acid refining structure, being formed to be rotatable, comprising:

a supply portion, through which is supplied a liquid including nucleic acid therein;

a nucleic acid capture portion, onto which is captured the nucleic acid within said supplied liquid;

a washing liquid supply portion, through which a washing liquid is supplied to said nucleic acid capture portion;

a waste portion, into which is wasted said washing liquid flowing through said nucleic acid capture portion;

an eluting solution supply portion, through which an eluting solution is supplied into said nucleic acid capture portion;

an eluting solution holder portion for holding the eluting solution including the nucleic acid therein, being captured on said nucleic acid capture portion once and separated therefrom, after flowing through said nucleic acid capture portion;

a waste liquid flow passage communicating between said eluting solution holder portion and said waste portion, wherein a connection portion between said eluting solution holder portion and said waste liquid flow passage is formed between an outer periphery side and an inner periphery side of said waste liquid flow passage;

a cover for covering said supply portion, said nucleic acid capture portion, said washing liquid supply portion, said waste portion, said eluting solution supply portion said eluting solution holder portion and said waste liquid flow passage, said cover having a plurality of air holes sealed by a sealing material; and a punching machine for selectively punching a hole in the sealing material in at least one of the holes to control flow of at least the eluting solution.

6. A nucleic acid refining structure, being formed to be rotatable, comprising:

a supply portion, through which is supplied a liquid including nucleic acid therein;

a nucleic acid capture portion, onto which is captured the nucleic acid within said supplied liquid;

a first reagent supply portion, through which a first reagent is supplied to said nucleic acid capture portion;

a waste portion, into which is wasted said first reagent flowing through said nucleic acid capture portion;

a second reagent supply portion, through which a second reagent is supplied to said nucleic acid capture portion, having a function of releasing said nucleic acid captured on said nucleic acid capture portion therefrom;

a second reagent holder portion for separating the nucleic acid captured on said nucleic acid capture portion therefrom, thereby to hold said second reagent contained within an inside thereof;

a waste liquid flow passage communicating between said second reagent holder portion and said waste portion, wherein a first area located on said waste flow passage between a most-inner periphery portion and a connection portion with said second reagent holder portion, and a second area located an outer periphery side than said most-inner periphery portion of said second reagent holder portion are formed, so that the total volume of the first and second areas is smaller than that of said first reagent to be supplied, while being larger than that of said second reagent to be supplied;

a cover for covering said supply portion, said nucleic acid capture portion, said first reagent supply portion, said waste portion, said second reagent supply portion said second reagent holder portion and said waste liquid flow passage, said cover having a plurality of air holes sealed by a sealing material; and a punching machine for selectively punching a hole in the sealing material in at least one of the holes to control flow of at least the eluting solution.

7. A nucleic acid refining structure, being formed to be rotatable, comprising:

a supply portion, through which is supplied a liquid including nucleic acid therein;

a nucleic acid capture portion, onto which is captured the nucleic acid within said supplied liquid;

a washing liquid supply portion, through which a washing liquid is supplied to said nucleic acid capture portion;

a waste portion, into which is wasted said washing liquid flowing through said nucleic acid capture portion;

an eluting solution supply portion, through which an eluting solution is supplied into said nucleic acid capture portion;

an eluting solution holder portion for holding the eluting solution including the nucleic acid therein, being captured on said nucleic acid capture portion once and separated therefrom, after flowing through said nucleic acid capture portion;

a waste liquid flow passage communicating between said eluting solution holder portion and said waste portion, wherein a first area located on said waste flow passage between a most-inner periphery portion and a connection portion with said eluting solution holder portion and a second area located on an outer periphery side than said most-inner periphery portion of said eluting solution holder portion are formed, so that the total volume of the first and second areas is smaller than that of said washing liquid to be supplied, while being larger than that of said eluting solution to be supplied;

a cover for covering said supply portion, said nucleic acid capture portion, said washing liquid supply portion, said waste portion, said eluting solution supply portion, said eluting solution holder portion and said waste liquid flow passage, said cover having a plurality of air holes sealed by a sealing material; and a punching machine for selectively punching a hole in the sealing material in at least one of the holes to control flow of at least the eluting solution.

8. A chemical material refining structure comprising:

a supply portion, through which is supplied a liquid including a first chemical material therein;

a first chemical material capture portion, onto which is captured said chemical material within said supplied liquid;

a first reagent supply portion, through which a first reagent is supplied to said first chemical material capture portion;

a waste portion, into which is wasted said first reagent flowing through said first chemical material capture portion;

a second reagent supply portion, through which a second reagent is supplied to said first chemical material capture portion, having a function of releasing said chemical material from said first chemical material capture portion;

a second reagent holder portion for holding said second reagent including said first chemical material therein, being captured on said first chemical material capture portion once and then separated therefrom after flowing through said first chemical material capture portion, wherein said second reagent holder portion is formed within a flow passage communicating between said first chemical material holder portion and said waste portion;

a cover for covering said supply portion, said first chemical material capture portion, said first reagent supply portion, said waste portion, said second reagent supply portion and said second reagent holder portion, said cover having a plurality of air holes sealed by a sealing material; and a punching machine for selectively punching a hole in the sealing material in at least one of the holes to control flow of at least the eluting solution.

* * * * *